US007906116B2

(12) United States Patent
Gill et al.

(10) Patent No.: US 7,906,116 B2
(45) Date of Patent: Mar. 15, 2011

(54) METHODS FOR USING AND IDENTIFYING MODULATORS OF DELTA-LIKE 4

(76) Inventors: Parkash Gill, Agoura Hills, CA (US); Ren Liu, Azusa, CA (US); Valery Krasnoperov, South Pasadena, CA (US)

( * ) Notice: Subject to any disclaimer, the term of this patent is extended or adjusted under 35 U.S.C. 154(b) by 199 days.

(21) Appl. No.: 12/005,054

(22) Filed: Dec. 20, 2007

(65) Prior Publication Data
US 2009/0035308 A1 Feb. 5, 2009

Related U.S. Application Data

(63) Continuation-in-part of application No. 11/514,773, filed on Sep. 1, 2006, now abandoned.

(60) Provisional application No. 60/713,637, filed on Sep. 1, 2005, provisional application No. 60/876,444, filed on Dec. 20, 2006, provisional application No. 60/901,754, filed on Feb. 16, 2007.

(51) Int. Cl.
*A61K 39/395* (2006.01)
*C07K 16/18* (2006.01)

(52) U.S. Cl. ............ 424/133.1; 424/130.1; 424/141.1; 424/178.1; 514/12; 530/388.1

(58) Field of Classification Search ............ 424/130.1, 424/133.1, 141.1, 178.1; 514/12; 530/388.1
See application file for complete search history.

(56) References Cited

U.S. PATENT DOCUMENTS

| | | | |
|---|---|---|---|
| 6,121,045 | A | 9/2000 | McCarthy et al. |
| 6,262,025 | B1 | 7/2001 | Ish-Horowicz et al. |
| 6,664,098 | B1 | 12/2003 | Sakano et al. |
| 6,689,744 | B2 | 2/2004 | Gao et al. |
| 6,737,507 | B2 | 5/2004 | Moses et al. |
| 6,783,956 | B2 | 8/2004 | Ish-Horowicz et al. |
| 7,022,499 | B2 | 4/2006 | Sakano et al. |
| 7,118,890 | B2 | 10/2006 | Ish-Horowicz et al. |
| 2005/0208027 | A1* | 9/2005 | Conboy et al. ............ 424/93.7 |
| 2006/0205823 | A1* | 9/2006 | Bodmer et al. ............ 514/686 |
| 2007/0213266 | A1 | 9/2007 | Gill et al. |
| 2008/0299088 | A1* | 12/2008 | Egan et al. ............ 424/93.7 |

FOREIGN PATENT DOCUMENTS

| | | |
|---|---|---|
| EP | 1 004 669 | 5/2000 |
| WO | WO-96/01839 | 1/1996 |
| WO | WO-97/01571 | 1/1997 |
| WO | WO-98/45434 | 10/1998 |
| WO | WO-00/06726 | 2/2000 |
| WO | WO-02/00690 | 1/2002 |
| WO | WO-02/08284 | 1/2002 |
| WO | WO-02/24221 | 3/2002 |
| WO | WO-03/018799 | 3/2003 |
| WO | WO-03/041735 | 5/2003 |
| WO | WO-03/087159 | 10/2003 |
| WO | 2004/083372 | * 9/2004 |
| WO | WO-2007/028110 A | 3/2007 |
| WO | WO-2007/070671 | 6/2007 |
| WO | WO-2008/079326 A | 7/2008 |

OTHER PUBLICATIONS

Adams et al., *Genes Dev.*, 13:295-306 (1999).
Artavanis-Tsakonas et al., *Science*, 284:770-776 (1999).
Benedito R., et al., "Expression of Dll4 during mouse embryogenesis suggests multiple developmental roles," Gene Expression Patters, Elsevier, vol. 5, No. 6, Aug. 2005.
Bray, S.J., "Notch signalling: a simple pathway become complex," Nat. Rev. Mol. Cell. Biol., 7:678-689 (2006).
Carmeliet, P., "Antiogenesis in life, disease and medicine," Nature, 438:932-936 (2005).
Carmeliet, P., et al., "Abnormal blood vessel development and lethality in embryos lacking a single VEGF allelle," Nature, 380:435-439 (1996).
Claxton et al., "Periodic Delta-like 4 expression in developing retinal arteries," Gene Expression Patterns, Elsevier, vol. 5, No. 1, Nov. 2004.
Duarte et al., *Genes Dev.*, 18:2474-2478 (2004).
Ferrara, N., et al., "Heterozygous embryonic lethality induced by targeted inactivation of the VEGF gene," Nature, 380:439-442 (1996).
Fischer et al., *Genes Dev.*, 18:901-911 (2004).
Diez, H., et al., "Hypoxia-mediated activation of Dll4-Notch-Hey2 signaling in endothelial progenitor cells and adoption of arterial cell fate," Exp Cell Res., 313:1-9 (2007).
Folkman, J., "Fundamental Concepts of the Angiogenic Process," Current Molecular Medicine, 3:643-651 (2003).
Gale et al., "Haploinsufficiency of delta-like 4 ligand results in embryonic lethality due to major defects in arterial and vascular development." Proceedings of the National Academy of Sciences of the USA, Nov. 2004, vol. 101, No. 45.
Gale et al., *Dev. Biol.*, 230:151-160 (2001).
Gerety, S.S., et al., "Symmetrical Mutant Phenotypes of the Receptor EphB4 and its Specific Transmembrane Ligand *ephrin-B2* in Cardiovascular Development," Molecular Cell, 4:403-414 (1999).
Hainaud, P., et al., "The Role of the Vascular Endothelial Growth Factor-Delta-like 4 Ligand/Notch4-Ephrin B2 Cascade in Tumor Vessel Remodeling and Endothelial Cell Functions," Cancer Research, 66(17):8501-8510 (2006).
Iso et al., *Arterioscler Thromb Vasc Biol.*, 23:543-553 (2003).
Kertesz, N., et al., "The Soluble Extracellular Domain of EphB4 (sEphB4) Antagonizes EphB4-EphrinB2 Interaction, Modulates Angiogenesis and Inhibits Tumor Growth," Blood, 107:2330-2338 (2006).
Krebs et al., *Genes Dev.*, 14:1343-1352 (2000).
Krebs, L.T., et al., "Haploinsufficient lethality and formation of arteriovenous malformations in Notch pathway mutants," Genes & Development, 18:2469-2473 (2004).
Lawson et al., *Dev. Cell*, 3:127-136 (2002).
Li et al., *Genomics*, 51(1):45-58 (1998).
Liu Zhao-Jun et al., "Regulation of Notch1 and Dll4 by vascular endothelial growth factor in arterial endothelial cells: implications for modulating arteriogenesis and angiogenesis." Database medline [online] U.S. National Library of Medicine, Bethesda, MD Jan. 2003, database accession No. NLM12482957.
Lobe et al., *Dev. Biol.*, 208(2):281-292 (1999).

(Continued)

*Primary Examiner* — Lynn Bristol
(74) *Attorney, Agent, or Firm* — Ropes & Gray LLP

(57) ABSTRACT

In certain embodiments, this present invention provides methods of identifying and using antibodies that act as either agonists or antagonists of Delta-like 4 (Dll4) signaling.

6 Claims, 29 Drawing Sheets

OTHER PUBLICATIONS

Lowell et al., "Stimulation of human epidermal differentiation by Delta-Notch signalling at the boundaries of stem-cell clusters," Current Biology, Current Science, GB, vol. 10, No. 9, May 2000.

Mailhos, C., et al., "Delta4, an endothelial specific notch ligand expressed at sites of physiological and tumor angiogenesis," Differentiation, 69:135-144 (2001).

Mumm and Kopan, *Dev. Biol.*, 228:151-165 (2000).

Nagy and Rossant, Gene Targeting: A Practical Approach, 177-206 (2000).

Noguera, et al., "Expression of Delta-like 4 (Dll4) ligand in mouse tumor models." Proceedings of the American Association for Cancer Research Annual Meeting, vol. 46, No. Suppl. S. Apr. 2005.

Risau, W., "Mechanisms of angiogenesis," Nature, 386:671-674 (1997).

Rossant, J., et al., "Vascular development and patterning: making the right choices," Curr. Opin. Genet. Dev., 13:408-412 (2003).

Sakai and Miyazaki, *Biochem. Biophys. Res. Commun.*, 237:318-324 (1997).

Scehnet et al., "Inhibition of Dll4-mediated signaling induces proliferation of immature vessels and results in poor tissue perfusion" Blood, 109(11):4753-60. 2007.

Shutter et al., *Genes Dev.*, 14:1313-1318 (2000).

Shweiki, D., et al., "Vascular endothelial growth factor induced by hypoxia may mediate hypoxia-initiated angiogenesis," Nature, 359:843-845 (1992).

Uyttendaele et al., *Development*, 122:2251-2259 (1996).

Wang, H.U., et al., "Molecular distinction and angiogenic interaction between embryonic arteries and veins revealed by ephrin-B2 and its receptor Eph-B4," Cell, 93:741-753 (1998).

Xia, G., et al., "Expression and significance of vascular endothelial growth factor receptor 2 in bladder cancer," J. Urol., 175:1245-1252 (2006).

Yoneya et al., *J. Biochem.*, 129:27-34 (2001).

Li, Ji-Liang et al, "Delta-like 4 notch ligand regulates tumor angiogenesis, improves tumor vascular function, and promotes tumor growth in vivo", Cancer Research, vol. 67(23); pp. 11244-11253 (2007).

Noguera-Troise, I., et al., "Blockade of Dll4 inhibits tumour growth by promoting non-productive angiogenesis," Nature, 444(7122):1032-1037 (2006).

Ridgway, J., et al., "Inhibition of Dll4 signalling inhibits tumour growth by deregulating angiogenesis," Nature, 444(7122):1083-1087 (2006).

* cited by examiner

Figure 1: Amino acid sequence of the human Delta-like 4 protein (SEQ ID NO:1; GenBank NP_061947).

```
  1 MAAASRSASG WALLLLVALW QQRAAGSGVF QLQLQEFINE RGVLASGRPC EPGCRTFFRV
 61 CLKHFQAVVS PGPCTFGTVS TPVLGTNSFA VRDDSSGGGR NPLQLPFNFT WPGTFSLIIE
121 AWHAPGDDLR PEALPPDALI SKIAIQGSLA VGQNWLLDEQ TSTLTRLRYS YRVICSDNYY
181 GDNCSRLCKK RNDHFGHYVC QPDGNLSCLP GWTGEYCQQP ICLSGCHEQN GYCSKPAECL
241 CRPGWQGRLC NECIPHNGCR HGTCSTPWQC TCDEGWGGLF CDQDLNYCTH HSPCKNGATC
301 SNSGQRSYTC TCRPGYTGVD CELELSECDS NPCRNGGSCK DQEDGYHCLC PPGYYGLHCE
361 HSTLSCADSP CFNGGSCRER NQGANYACEC PPNFTGSNCE KKVDRCTSNP CANGGQCLNR
421 GPSRMCRCRP GFTGTYCELH VSDCARNPCA HGGTCHDLEN GLMCTCPAGF SGRRCEVRTS
481 IDACASSPCF NRATCYTDLS TDTFVCNCPY GFVGSRCEFP VGLPPSFPWV AVSLGVGLAV
541 LLVLLGMVAV AVRQLRLRRP DDGSREAMNN LSDFQKDNLI PAAQLKNTNQ KKELEVDCGL
601 DKSNCGKQQN HTLDYNLAPG PLGRGTMPGK FPHSDKSLGE KAPLRLHSEK PECRISAICS
661 PRDSMYQSVC LISEERNECV IATEV
```

Figure 2: Nucleic acid sequence (cDNA) encoding the human Delta-like 4 protein (SEQ ID NO:2; GenBank NM_019074).

```
   1 gctgcgcgca ggccgggaac acgaggccaa gagccgcagc cccagccgcc ttggtgcagc
  61 gtacaccggc actagcccgc ttgcagcccc aggattagac agaagacgcg tcctcggcgc
 121 ggtcgccgcc cagccgtagt cacctggatt acctacagcg gcagctgcag cggagccagc
 181 gagaaggcca aggggagca gcgtcccgag aggagcgcct cttttcaggg accccgccgg
 241 ctggcggacg cgcgggaaag cggcgtcgcg aacagagcca gattgagggc ccgcgggtgg
 301 agagagcgac gcccgagggg atggcggcag cgtcccggag cgcctctggc tgggcgctac
 361 tgctgctggt ggcactttgg cagcagcgcg cggccggctc cggcgtcttc cagctgcagc
 421 tgcaggagtt catcaacgag cgcggcgtac tggccagtgg gcggccttgc gagcccggct
 481 gccggacttt cttccgcgtc tgccttaagc acttccaggc ggtcgtctcg cccggaccct
 541 gcaccttcgg gaccgtctcc acgccggtat tgggcaccaa ctccttcgct gtccgggacg
 601 acagtagcgg cggggggcgc aaccctctcc aactgccctt caatttcacc tggccgggta
 661 ccttctcgct catcatcgaa gcttggcacg cgccaggaga cgacctgcgg ccagaggcct
 721 tgccaccaga tgcactcatc agcaagatcg ccatccaggg ctccctagct gtgggtcaga
 781 actggttatt ggatgagcaa accagcaccc tcacaaggct gcgctactct taccgggtca
 841 tctgcagtga caactactat ggagacaact gctcccgcct gtgcaagaag cgcaatgacc
 901 acttcggcca ctatgtgtgc cagccagatg caacttgtc ctgcctgccc ggttggactg
 961 gggaatattg ccaacagcct atctgtcttt cgggctgtca tgaacagaat ggctactgca
1021 gcaagccagc agagtgcctc tgccgcccag gctggcaggg ccggctgtgt aacgaatgca
1081 tcccccacaa tggctgtcgc cacggcacct gcagcactcc ctggcaatgt acttgtgatg
1141 agggctgggg aggcctgttt tgtgaccaag atctcaacta ctgcacccac cactccccat
1201 gcaagaatgg ggcaacgtgc tccaacagtg ggcagcgaag ctacacctgc acctgtcgcc
1261 caggctacac tggtgtggac tgtgagctgg agctcagcga gtgtgacagc aaccctgtc
1321 gcaatggagg cagctgtaag gaccaggagg atggctacca ctgcctgtgt cctccgggct
1381 actatggcct gcattgtgaa cacagcacct tgagctgcgc cgactccccc tgcttcaatg
1441 ggggctcctg ccgggagcgc aaccaggggg ccaactatgc ttgtgaatgt ccccccaact
1501 tcaccggctc caactgcgag aagaaagtgg acaggtgcac cagcaacccc tgtgccaacg
1561 ggggacagtg cctgaaccga ggtccaagcc gcatgtgccg ctgccgtcct ggattcacgg
1621 gcacctactg tgaactccac gtcagcgact gtgcccgtaa ccttgcgcc cacggtggca
1681 cttgccatga cctggagaat gggctcatgt gcacctgccc tgccggcttc tctggccgac
1741 gctgtgaggt gcggacatcc atcgatgcct gtgcctcgag tccctgcttc aacagggca
1801 cctgctacac cgacctctcc acagacacct tgtgtgcaa ctgcccttat ggctttgtgg
1861 gcagccgctg cgagttcccc gtgggcttgc cgccagctt ccctgggtg gccgtctcgc
1921 tgggtgtggg gctggcagtg ctgctggtac tgctgggcat ggtggcagtg gctgtgcggc
1981 agctgcggct tcgacggccg gacgacggca gcagggaagc catgaacaac ttgtcggact
2041 tccagaagga caacctgatt cctgccgccc agcttaaaaa cacaaaccag aagaaggagc
```

```
2101 tggaagtgga ctgtggcctg gacaagtcca actgtggcaa acagcaaaac cacacattgg
2161 actataatct ggccccaggg ccctgggggc gggggaccat gccaggaaag tttccccaca
2221 gtgacaagag cttaggagag aaggcgccac tgcggttaca cagtgaaaag ccagagtgtc
2281 ggatatcagc gatatgctcc cccagggact ccatgtacca gtctgtgtgt ttgatatcag
2341 aggagaggaa tgaatgtgtc attgccacgg aggtataagg caggagccta cctggacatc
2401 cctgctcagc ccgcggctg gaccttcctt ctgcattgtt tacattgcat cctggatggg
2461 acgttttca tatgcaacgt gctgctctca ggaggaggag ggaatggcag gaaccggaca
2521 gactgtgaac ttgccaagag atgcaatacc cttccacacc tttgggtgtc tgtctggcat
2581 cagattggca gctgcaccaa ccagaggaac agaagagaag agagatgcca ctgggcactg
2641 ccctgccagt agtggccttc aggggctcc ttccgggct ccggcctgtt ttccagagag
2701 agtggcagta gccccatggg gcccggagct gctgtggcct ccactggcat ccgtgtttcc
2761 aaaagtgcct ttggcccagg ctccacggcg acagttgggc ccaaatcaga aaggagagag
2821 ggggccaatg agggcagggc ctcctgtggg ctggaaaacc actgggtgcg tctcttgctg
2881 gggtttgccc tggaggtgag gtgagtgctc gagggagggg agtgctttct gccccatgcc
2941 tccaactact gtatgcaggc ctggctctct ggtctaggcc ctttgggcaa gaatgtccgt
3001 ctaccggct tccaccaccc tctggccctg ggcttctgta agcagacagg cagagggcct
3061 gcccctccca ccagccaagg gtgccaggcc taactggggc actcagggca gtgtgttgga
3121 aattccactg aggggggaaat caggtgctgc ggccgcctgg gcctttcct ccctcaagcc
3181 catctccaca acctcgagcc tgggctctgg tccactactg ccccagacca ccctcaaagc
3241 tggtcttcag aaatcaataa tatgagtttt tattttgttt ttttttttt ttttgtagtt
3301 tattttggag tctagtattt caataattta agaatcagaa gcactgacct ttctacattt
3361 tataacatta ttttgtatat aat
```

Figure 2 (cont.)

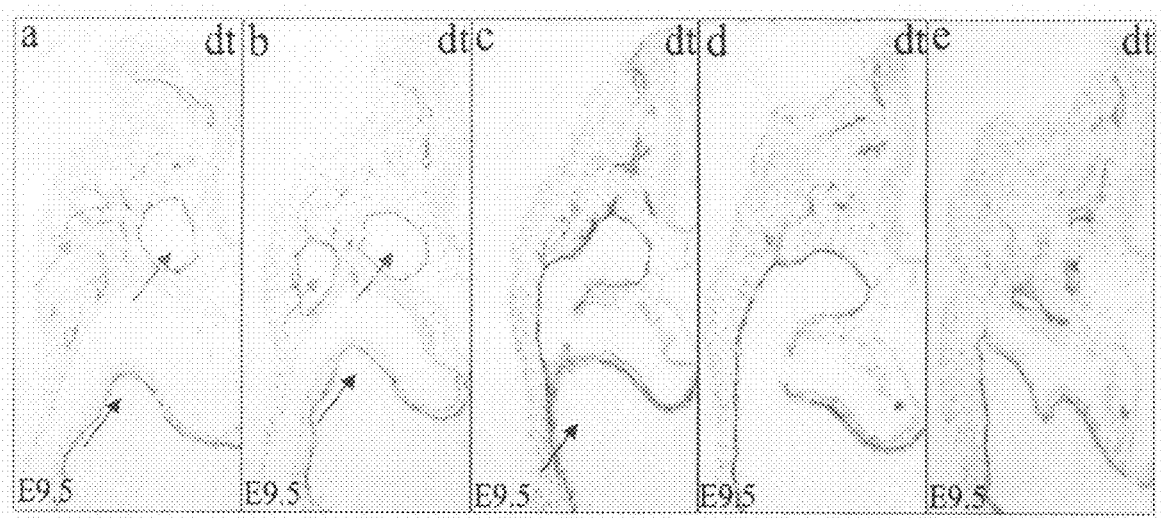
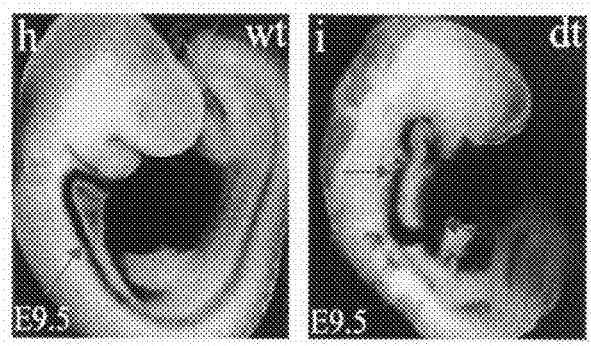
Figure 6

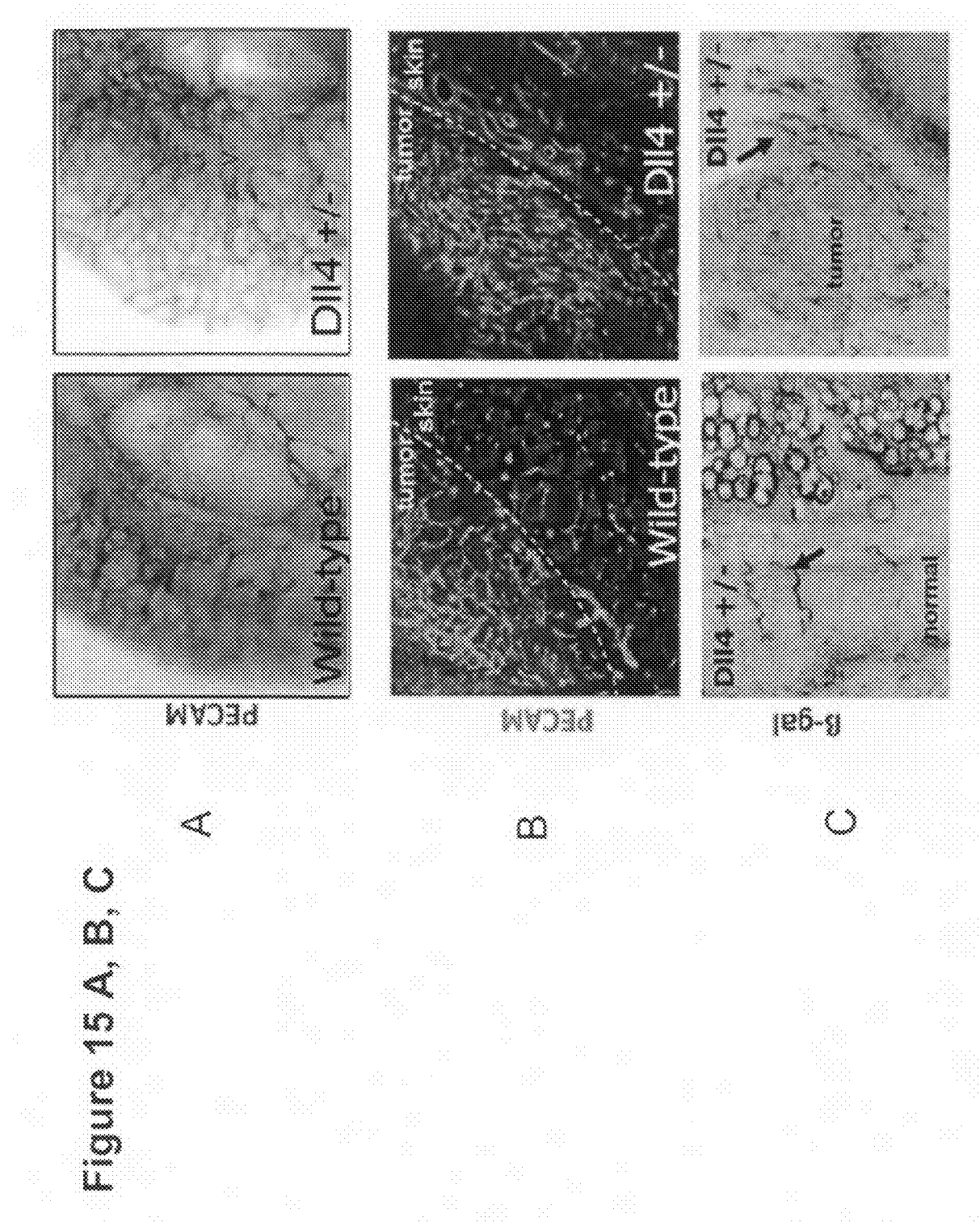
Figure 15 A, B, C

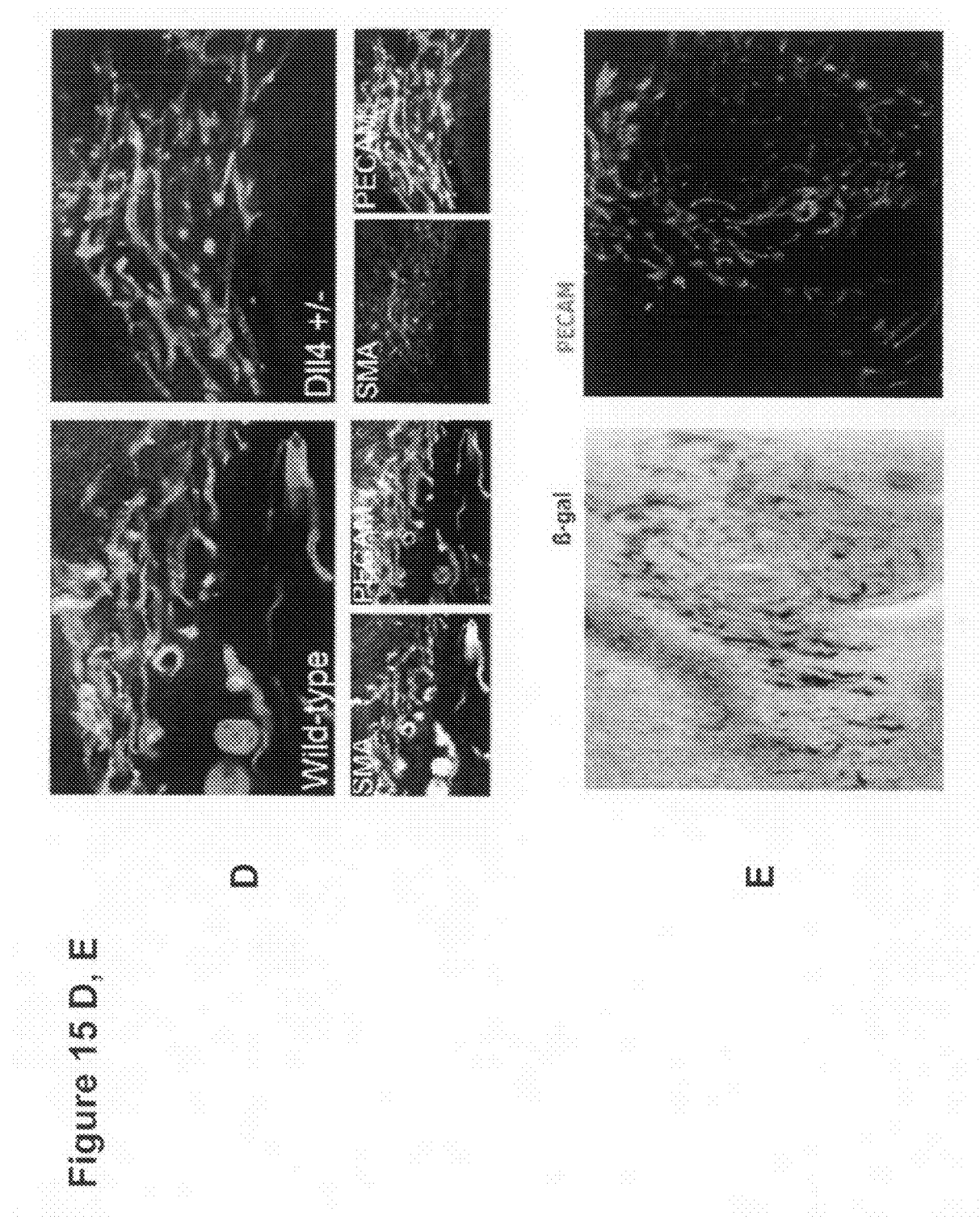
Figure 15 D, E

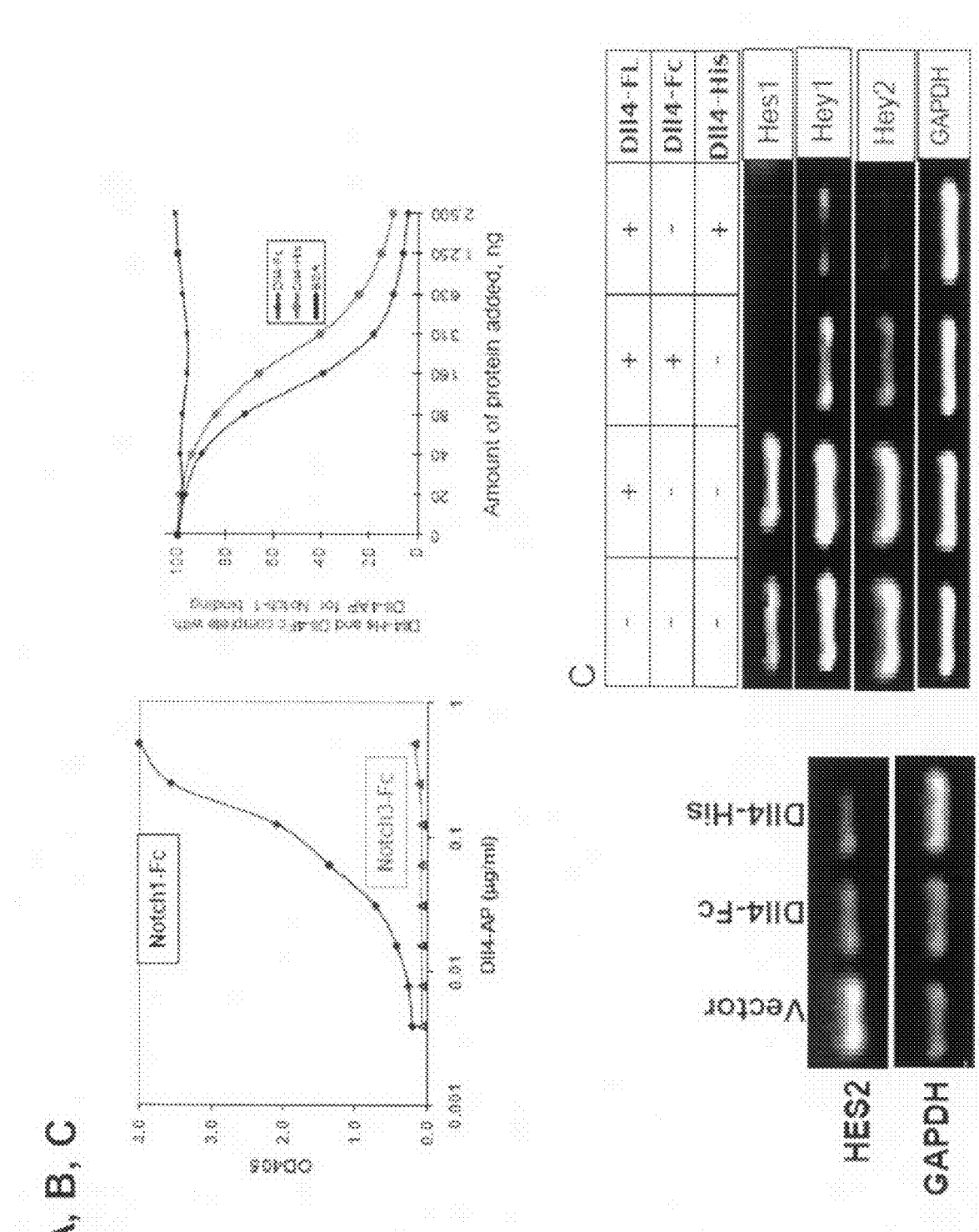
Figure 16 A, B, C

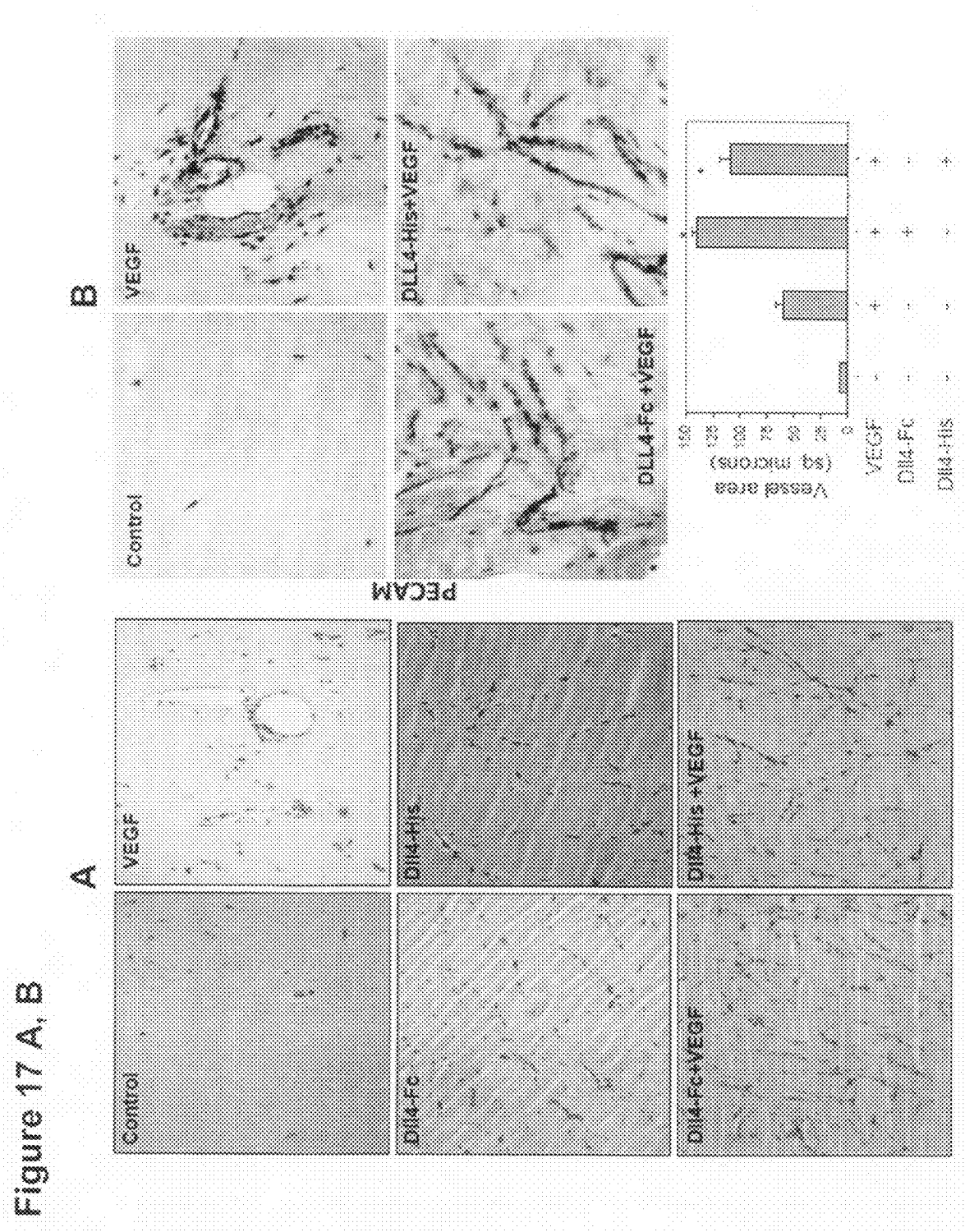
Figure 17 A, B

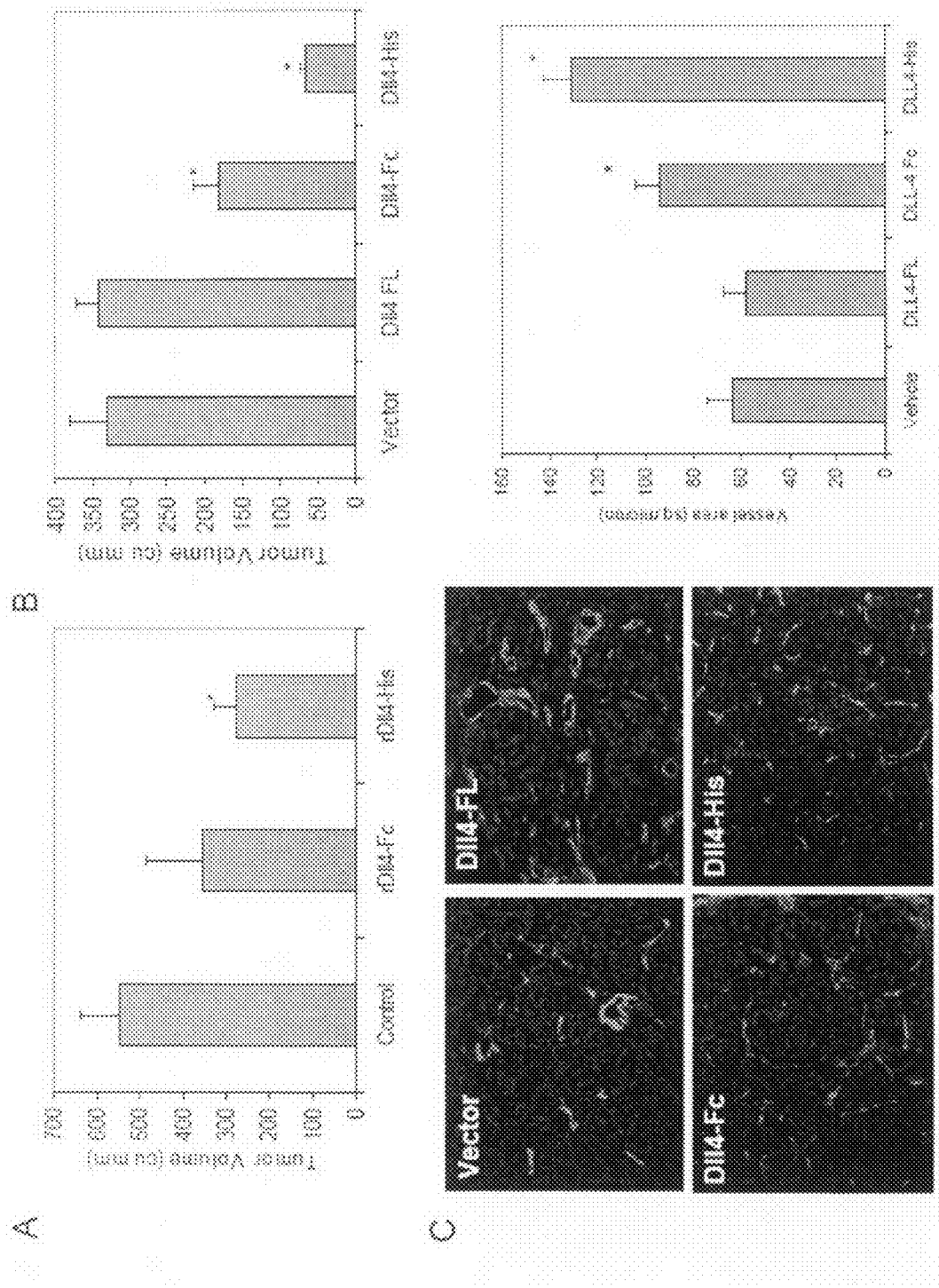
Figure 18 A, B, C

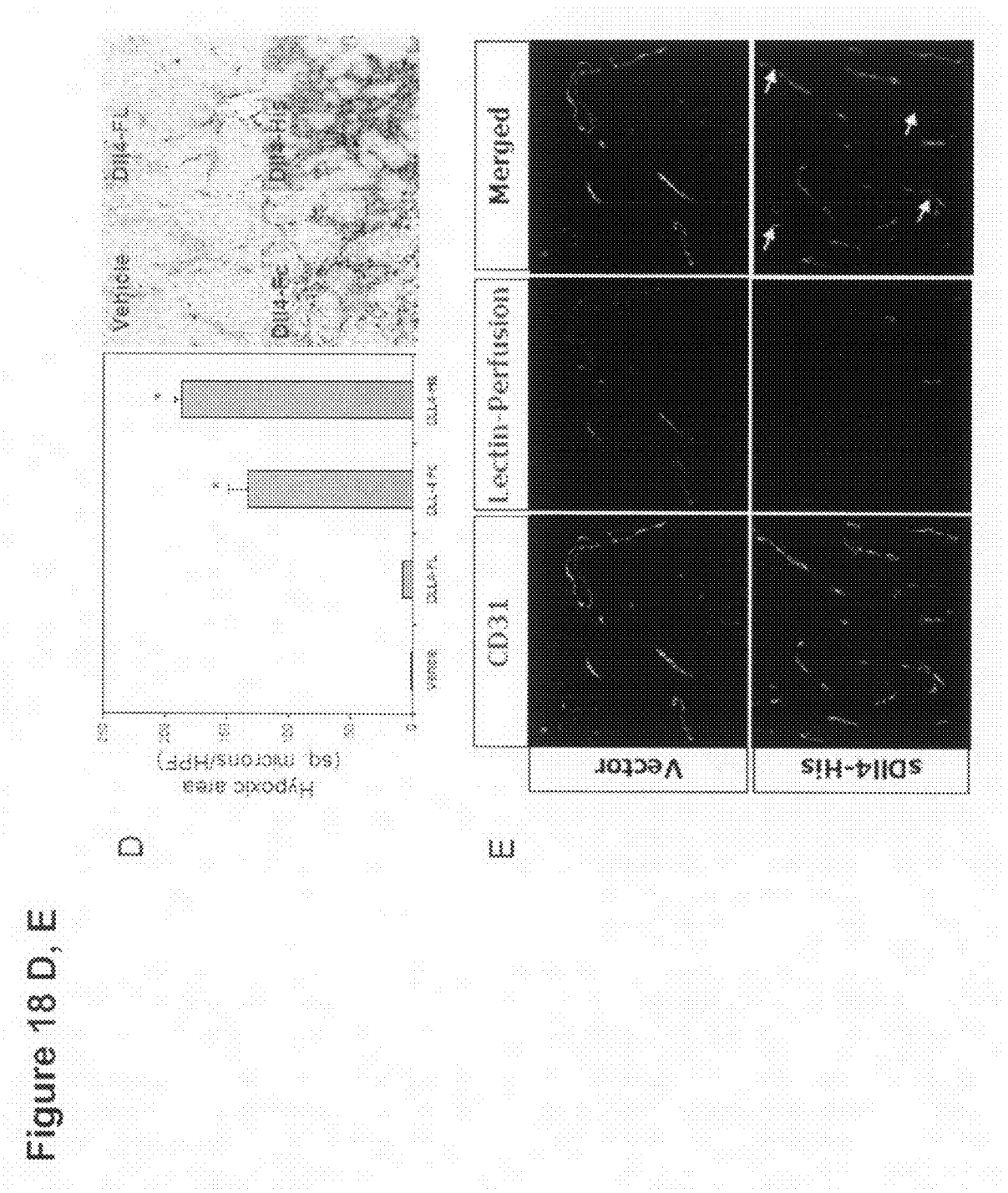
Figure 18 D, E

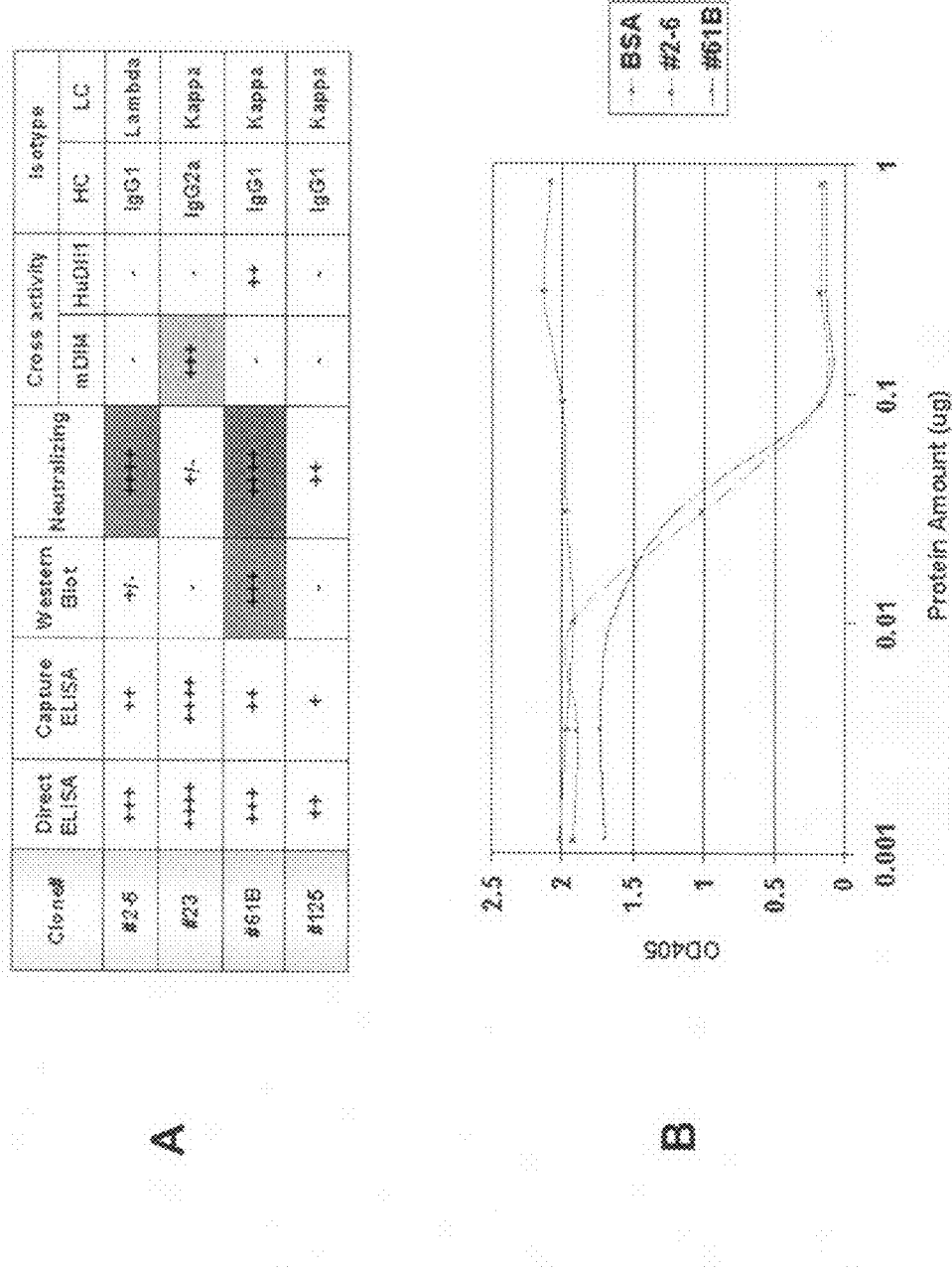
Figure 22 A, B

Figure 23

SEQ ID NO: 4

61B VH
GCTACGCGTGTCCACTCCGAGGTCCAGCTGCAGCAGTCTGGGACCTGAGCTGCAGAAGCCTGGGGCTTCAGTGAAGATGTCCTGCAAGGC
TTCTGGATACACATTCACTAGCTATGTTATAAACTGGGTGAAGCAGAAGCCTGGGCAGGGCCTTGAGTGGATTGGATATAATCCTT
ACAATGATGGTACTAAGTACAATGAGAAGTTCAAAGTCAAGGCCACACTGACTTCAGACAAATCCTCCAGCACAGCCTACATGGAGCTC
AGCAGCCTGACCTCTGAGGACTCTGCGGTCTATTACTGTGCATCTTATTACTACGGTAGTAGTACTACTTTGACTACTACTGGGGCCAAGG
CACCACTCTCACAGTCTCCTCAGGTAAGCTT

SEQ ID NO: 5

61B VL
GCGGCGATGTGACATCCAGATGACACAATCTTCATCCTACTTGTCTCTGTATCTCTAGGAGGCAGAGTCACCATTACTTGCAAGGCAAGT
GACCACATTAATAATTGGTTAGCCTGGTATCAGCAGAAACCAGGAAATGCTCCTAGGCTCTTAATATCTGGTGCAACCAGTTTGGAAAC
TGGGGTCTTCCTTCAAGATTCAGTGGCAGTGGATCTGGAAAGGATTACACTCTTCAGCATTACCAGTCTTCAGACTGAAGATGTTGCTACTT
ATTACTGTCAACAGTATTCCGCTCACGTTCGGTGCTGGGACCAAGCTGGAGCTGAAACGTGAGTAGAATTAAACTTTGCT
TCCTCAGTTGGATCC

Figure 24

SEQ ID NO: 6

2-6 VH
ATGGGATGGAGCGGGGTCTTTATCTTAATCCTGTCAGTAACTACAGGTGTCCACTCTGAGGTCCAGCTGCAGCAGTCTGGACCTGAGCT
GGAGAAGCCTGGCGCTTCAGTGAAGATATCCTGGAAGACTTCACTGGTTACTCATTCATTACTAACTACACCAGAAGTTCAAGGCAAGGCCACATTG
ATGGAAAGAGACCTTGAGTGGATTGGAAATATTGATCCTTACTTTGGTGGTACTAACTACAACCAGAAGTTCAAGGGCAAGGCCACATTG
ACTGTAGACACAAATCCTCCAGACACAGCCTACATGCAGCTCAAGAGCCTGACAGCCTGAGGACTCTGCAGTCTATTACTGTGCAAGAAACTA
TGATTACGACGAGGATGCTTTGACTACTGGGGCCAAGGCACCACTCTCACAGTCTCCTCAG

SEQ ID NO: 7

2-6 VL
ATGGCCTGGATTCCTCTCTATATTCTCTCCCTGGCTCTCAGCTCTGTTGTGACTCAGGAATCTGCACTCAC
CACATCCTGTGGTGAAACAGTCACTCACTGTCGCTCAAGTACTGGGCTGTTACAACTATGCCAACTGGGTCCAAGAAA
AACCAGATCATTATTCACTGGTCTAATAGGTGGTACCAACAACCGAGCTCCAGGTGTTCTCAGGCTCCCTGATTGGA
GACAAGGCTGCCCTCACCATCACAGGGCACAGAGACTGAGGATGAGGCAATATATTTCTGTGCTCTATGGTACAGCAACAACATTGGGTGTT
CGGTGGAGGAACCAAACTGACTGTCCTAGGCCCAAG

```
                          SEQUENCE LISTING

<160> NUMBER OF SEQ ID NOS: 15

<210> SEQ ID NO 1
<211> LENGTH: 685
<212> TYPE: PRT
<213> ORGANISM: Homo sapiens

<400> SEQUENCE: 1

Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
```

```
                    325                 330                 335
Gly Ser Cys Lys Asp Gln Glu Asp Gly Tyr His Cys Leu Cys Pro Pro
                340                 345                 350
Gly Tyr Tyr Gly Leu His Cys Glu His Ser Thr Leu Ser Cys Ala Asp
                355                 360                 365
Ser Pro Cys Phe Asn Gly Gly Ser Cys Arg Glu Arg Asn Gln Gly Ala
            370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
                435                 440                 445
Cys Ala His Gly Gly Thr Cys His Asp Leu Glu Asn Gly Leu Met Cys
            450                 455                 460
Thr Cys Pro Ala Gly Phe Ser Gly Arg Arg Cys Glu Val Arg Thr Ser
465                 470                 475                 480
Ile Asp Ala Cys Ala Ser Ser Pro Cys Phe Asn Arg Ala Thr Cys Tyr
                485                 490                 495
Thr Asp Leu Ser Thr Asp Thr Phe Val Cys Asn Cys Pro Tyr Gly Phe
                500                 505                 510
Val Gly Ser Arg Cys Glu Phe Pro Val Gly Leu Pro Pro Ser Phe Pro
            515                 520                 525
Trp Val Ala Val Ser Leu Gly Val Gly Leu Ala Val Leu Leu Val Leu
        530                 535                 540
Leu Gly Met Val Ala Val Ala Val Arg Gln Leu Arg Leu Arg Arg Pro
545                 550                 555                 560
Asp Asp Gly Ser Arg Glu Ala Met Asn Asn Leu Ser Asp Phe Gln Lys
                565                 570                 575
Asp Asn Leu Ile Pro Ala Ala Gln Leu Lys Asn Thr Asn Gln Lys Lys
            580                 585                 590
Glu Leu Glu Val Asp Cys Gly Leu Asp Lys Ser Asn Cys Gly Lys Gln
            595                 600                 605
Gln Asn His Thr Leu Asp Tyr Asn Leu Ala Pro Gly Pro Leu Gly Arg
        610                 615                 620
Gly Thr Met Pro Gly Lys Phe Pro His Ser Asp Lys Ser Leu Gly Glu
625                 630                 635                 640
Lys Ala Pro Leu Arg Leu His Ser Glu Lys Pro Glu Cys Arg Ile Ser
                645                 650                 655
Ala Ile Cys Ser Pro Arg Asp Ser Met Tyr Gln Ser Val Cys Leu Ile
                660                 665                 670
Ser Glu Glu Arg Asn Glu Cys Val Ile Ala Thr Glu Val
            675                 680                 685

<210> SEQ ID NO 2
<211> LENGTH: 3383
<212> TYPE: DNA
<213> ORGANISM: Homo sapiens

<400> SEQUENCE: 2
gctgcgcgca ggccgggaac acgaggccaa gagccgcagc cccagccgcc ttggtgcagc      60
gtacaccggc actagcccgc ttgcagcccc aggattagac agaagacgcg tcctcggcgc     120
```

```
ggtcgccgcc cagccgtagt cacctggatt acctacagcg gcagctgcag cggagccagc    180
gagaaggcca aggggagca gcgtcccgag aggagcgcct cttttcaggg accccgccgg    240
ctggcggacg cgcgggaaag cggcgtcgcg aacagagcca gattgagggc cgcgggtgg    300 agagagcgac gcccgagggg atggcggcag cgtcccggag cgcctctggc tgggcgctac    360
tgctgctggt ggcactttgg cagcagcgcg cggccggctc cggcgtcttc cagctgcagc    420
tgcaggagtt catcaacgag cgcggcgtac tggccagtgg gcggccttgc gagcccggct    480
gccggacttt cttccgcgtc tgccttaagc acttccaggc ggtcgtctcg cccggaccct    540
gcaccttcgg gaccgtctcc acgccggtat tgggcaccaa ctccttcgct gtccgggacg    600
acagtagcgg cgggggggcgc aaccctctcc aactgcccct caatttcacc tggccgggta    660
ccttctcgct catcatcgaa gcttggcacg cgccaggaga cgacctgcgg ccagaggcct    720
tgccaccaga tgcactcatc agcaagatcg ccatccaggg ctccctagct gtgggtcaga    780
actggttatt ggatgagcaa accagcaccc tcacaaggct gcgctactct taccgggtca    840
tctgcagtga caactactat ggagacaact gctcccgcct gtgcaagaag cgcaatgacc    900
acttcggcca ctatgtgtgc cagccagatg gcaacttgtc ctgcctgccc ggttggactg    960
gggaatattg ccaacagcct atctgtcttt cgggctgtca tgaacagaat ggctactgca   1020
gcaagccagc agagtgcctc tgccgcccag gctggcaggg ccggctgtgt aacgaatgca   1080
tcccccacaa tggctgtcgc cacggcacct gcagcactcc ctggcaatgt acttgtgatg   1140
agggctgggg aggcctgttt tgtgaccaag atctcaacta ctgcacccac cactccccat   1200
gcaagaatgg ggcaacgtgc tccaacagtg ggcagcgaag ctacacctgc acctgtcgcc   1260
caggctacac tggtgtggac tgtgagctgg agctcagcga gtgtgacagc aacccctgtc   1320
gcaatggagg cagctgtaag gaccaggagg atggctacca ctgcctgtgt cctccgggct   1380
actatggcct gcattgtgaa cacagcacct tgagctgcgc cgactccccc tgcttcaatg   1440
ggggctcctg ccgggagcgc aaccagggg ccaactatgc ttgtgaatgt ccccccaact   1500
tcaccggctc caactgcgag aagaaagtgg acaggtgcac cagcaacccc tgtgccaacg   1560
ggggacagtg cctgaaccga ggtccaagcc gcatgtgccg ctgccgtcct ggattcacgg   1620
gcacctactg tgaactccac gtcagcgact gtgcccgtaa cccttgcgcc acggtggca   1680 cttgccatga cctggagaat gggctcatgt gcacctgccc tgccggcttc tctggccgac   1740
gctgtgaggt gcggacatcc atcgatgcct gtgcctcgag tccctgcttc aacagggcca   1800
cctgctacac cgacctctcc acagacacct ttgtgtgcaa ctgcccttat ggctttgtgg   1860
gcagccgctg cgagttcccc gtgggcttgc cgcccagctt cccctgggtg gccgtctcgc   1920
tgggtgtggg gctggcagtg ctgctggtac tgctgggcat ggtggcagtg gctgtgcggc   1980
agctgcggct cgacggccg gacgacggca gcagggaagc catgaacaac ttgtcggact   2040
tccagaagga caacctgatt cctgccgccc agcttaaaaa cacaaaccag aagaaggagc   2100
tggaagtgga ctgtggcctg gacaagtcca actgtggcaa acagcaaaac cacacattgg   2160
actataatct ggccccaggg ccccgtgggc ggggaccat gccaggaaag tttccccaca   2220
gtgacaagag cttaggagag aaggcgccac tgcggttaca cagtgaaaag ccagagtgtc   2280
ggatatcagc gatatgctcc cccagggact ccatgtacca gtctgtgtgt ttgatatcag   2340
aggagaggaa tgaatgtgtc attgccacgg aggtataagg caggagccta cctggacatc   2400
cctgctcagc cccgcggctg gaccttcctt ctgcattgtt tacattgcat cctggatggg   2460
acgtttttca tatgcaacgt gctgctctca ggaggaggag ggaatggcag gaaccggaca   2520
```

-continued

```
gactgtgaac ttgccaagag atgcaatacc cttccacacc tttgggtgtc tgtctggcat    2580
cagattggca gctgcaccaa ccagaggaac agaagagaag agagatgcca ctgggcactg    2640
ccctgccagt agtggccttc aggggctcc ttccggggct ccggcctgtt ttccagagag    2700
agtggcagta gccccatggg gcccggagct gctgtggcct ccactggcat ccgtgtttcc    2760
aaaagtgcct ttggcccagg ctccacggcg acagttgggc ccaaatcaga aggagagag    2820 ggggccaatg agggcagggc ctcctgtggg ctggaaaacc actgggtgcg tctcttgctg    2880
gggtttgccc tggaggtgag gtgagtgctc gagggagggg agtgctttct gccccatgcc    2940
tccaactact gtatgcaggc ctggctctct ggtctaggcc cttgggcaa gaatgtccgt    3000 ctacccggct ccaccaccc tctggccctg gcttctgta agcagacagg cagagggcct    3060 gccctccca ccagccaagg gtgccaggcc taactgggc actcagggca gtgtgttgga    3120
aattccactg aggggaaat caggtgctgc ggccgcctgg gccctttcct ccctcaagcc    3180
catctccaca acctcgagcc tgggctctgg tccactactg ccccagacca ccctcaaagc    3240
tggtcttcag aaatcaataa tatgagtttt tattttgttt ttttttttt ttttgtagtt    3300 tattttggag tctagtattt caataattta agaatcagaa gcactgacct ttctacattt    3360
tataacatta ttttgtatat aat                                           3383
```

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Pro Ser Cys Ile Tyr Arg Arg Ser Trp Arg Ser Arg Gly Ala
1               5                   10                  15

Gln Ile Leu

<210> SEQ ID NO 4
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gctacgcgtg tccactccga ggtccagctg cagcagtctg acctgagct ggtaaagcct      60 ggggcttcag tgaagatgtc ctgcaaggct tctggataca cattcactag ctatgttata    120
aactgggtga agcagaagcc tggcagggc cttgagtgga ttggattaat taatccttac    180
aatgatggta ctaagtacaa tgagaagttc aaagtcaagg ccacactgac ttcagacaaa    240
tcctccagca cagcctacat ggagctcagc agcctgacct ctgaggactc tgcggtctat    300
tactgtgcat cttattacta cggtagtagg tactactttg actactgggg ccaaggcacc    360
actctcacag tctcctcagg taagctt                                         387
```

<210> SEQ ID NO 5
<211> LENGTH: 371
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 5

```
gcgcgcgatg tgacatccag atgacacaat cttcatccta cttgtctgta tctctaggag    60
gcagagtcac cattacttgc aaggcaagtg accacattaa taattggtta gcctggtatc   120
agcagaaacc aggaaatgct cctaggctct taatatctgg tgcaaccagt ttggaaactg   180
gggttccttc aagattcagt ggcagtggat ctggaaagga ttacactctc agcattacca   240
gtcttcagac tgaagatgtt gctacttatt actgtcaaca gtattggagt attccgctca   300
cgttcggtgc tgggaccaag ctggagctga acgtgagta gaatttaaac tttgcttcct   360
cagttggatc c                                                       371
```

<210> SEQ ID NO 6
<211> LENGTH: 418
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgggatgga gcggggtctt tatcttaatc ctgtcagtaa ctacaggtgt ccactctgag    60
gtccagctgc agcagtctgg acctgagctg agaagcctg gcgcttcagt gaagatatcc   120
tgcaaggctt ctggttactc attcactggc tacaacatga actgggtgaa gcagagcaat   180
ggaaagagcc ttgagtggat tggaaatatt gatccttact ttggtggtac taactacaac   240
cagaagttca aggcaaggc acattgact gtagacaaat cctccagcac agcctacatg   300
cagctcaaga gcctgacatc tgaggactct gcagtctatt actgtgcaag aaactatgat   360
tacgacggag gatgctttga ctactggggc caaggcacca ctctcacagt ctcctcag   418
```

<210> SEQ ID NO 7
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atggcctgga ttcctcttat attctctctc ctggctctca gctcaggggc catttcccag    60
gctgttgtga ctcaggaatc tgcactcacc acatcacctg gtgaaacagt cacactcact   120
tgtcgctcaa gtactggggc tgttacaact agtaactatg ccaactgggt ccaagaaaaa   180
ccagatcatt tattcactgg tctaataggt ggtaccaaca accgagctcc aggtgttcct   240
gccagattct caggctccct gattggagac aaggctgccc tcaccatcac aggggcacag   300
actgaggatg aggcaatata tttctgtgct ctatggtaca gcaaccattg ggtgttcggt   360
ggaggaacca aactgactgt cctaggccag cccaag                            396
```

<210> SEQ ID NO 8
<211> LENGTH: 340
<212> TYPE: PRT
<213> ORGANISM: Homo sapiens

<400> SEQUENCE: 8

Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
            20                  25                  30

```
Gln Leu Gln Glu Phe Ile Asn Glu Arg Gly Val Leu Ala Ser Gly Arg
         35                  40                  45

Pro Cys Glu Pro Gly Cys Arg Thr Phe Arg Val Cys Leu Lys His
 50                  55                  60

Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
             115                 120                 125

Leu Arg Pro Glu Ala Leu Pro Pro Asp Ala Leu Ile Ser Lys Ile Ala
130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
290                 295                 300

Gln Arg Ser Tyr Thr Gly Val Asp Cys Glu Leu Glu Leu Ser Glu Cys
305                 310                 315                 320

Asp Ser Asn Pro Cys Arg Asn Gly Gly Ser Cys Lys Asp Gln Glu Asp
                325                 330                 335

Gly Tyr His Cys
            340

<210> SEQ ID NO 9
<211> LENGTH: 349
<212> TYPE: PRT
<213> ORGANISM: Mus sp.

<400> SEQUENCE: 9

Met Thr Pro Ala Ser Arg Ser Ala Cys Arg Trp Ala Leu Leu Leu Leu
 1               5                  10                  15

Ala Val Leu Trp Pro Gln Gln Arg Ala Ala Gly Ser Gly Ile Phe Gln
                 20                  25                  30

Leu Arg Leu Gln Glu Phe Val Asn Gln Arg Gly Met Leu Ala Asn Gly
         35                  40                  45

Gln Ser Cys Glu Pro Gly Cys Arg Thr Phe Arg Ile Cys Leu Lys
 50                  55                  60
```

```
His Phe Gln Ala Thr Phe Ser Glu Gly Pro Cys Thr Phe Gly Asn Val
 65                  70                  75                  80

Ser Thr Pro Val Leu Gly Thr Asn Ser Phe Val Arg Asp Lys Asn
                 85                  90                  95

Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
            115                 120                 125

Asp Leu Arg Pro Glu Thr Ser Pro Gly Asn Ser Leu Ile Ser Gln Ile
            130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
            195                 200                 205

Cys Leu Pro Gly Trp Thr Gly Lys Tyr Cys Asp Gln Pro Ile Cys Leu
210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                245                 250                 255

His Asn Gly Cys Arg His Gly Thr Cys Ser Ile Pro Trp Gln Cys Ala
            260                 265                 270

Cys Asp Glu Gly Trp Gly Gly Leu Phe Cys Asp Gln Asp Leu Asn Tyr
            275                 280                 285

Cys Thr His His Ser Pro Cys Lys Asn Gly Thr Cys Ser Asn Ser
            290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                325                 330                 335

Gly Gly Ser Cys Lys Asp Gln Glu Asn Ser Tyr His Cys
            340                 345
```

<210> SEQ ID NO 10
<211> LENGTH: 352
<212> TYPE: PRT
<213> ORGANISM: Homo sapiens

<400> SEQUENCE: 10

```
Met Gly Ser Arg Cys Ala Leu Ala Leu Ala Val Leu Ser Ala Leu Leu
 1               5                  10                  15

Cys Gln Val Trp Ser Ser Gly Val Phe Glu Leu Lys Leu Gln Glu Phe
             20                  25                  30

Val Asn Lys Lys Gly Leu Leu Gly Asn Arg Asn Cys Cys Arg Gly Gly
         35                  40                  45

Ala Gly Pro Pro Pro Cys Ala Cys Arg Thr Phe Phe Arg Val Cys Leu
     50                  55                  60

Lys His Tyr Gln Ala Ser Val Ser Pro Glu Pro Pro Cys Thr Tyr Gly
 65                  70                  75                  80

Ser Ala Val Thr Pro Val Leu Gly Val Asp Ser Phe Ser Leu Pro Asp
                 85                  90                  95
```

-continued

```
Gly Gly Gly Ala Asp Ser Ala Phe Ser Asn Pro Ile Arg Phe Pro Phe
            100                 105                 110
Gly Phe Thr Trp Pro Gly Thr Phe Ser Leu Ile Ile Glu Ala Leu His
        115                 120                 125
Thr Asp Ser Pro Asp Asp Leu Ala Thr Glu Asn Pro Glu Arg Leu Ile
    130                 135                 140
Ser Arg Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
        195                 200                 205
Glu Lys Val Cys Asn Pro Gly Trp Lys Gly Pro Tyr Cys Thr Glu Pro
    210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
                245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
        275                 280                 285
Leu Asn Tyr Cys Thr His His Lys Pro Cys Lys Asn Gly Ala Thr Cys
    290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Pro Gly
1

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser Gly Gly Gly Gly Gly Gly
1               5

<210> SEQ ID NO 13
<211> LENGTH: 16
<212> TYPE: PRT
```

```
-continued

<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Gly Gly Gly Ser Gly Gly Gly Gly Ser Gly Gly Gly Gly
1               5                   10                  15

<210> SEQ ID NO 14
<211> LENGTH: 6
<212> TYPE: PRT
<213> ORGANISM: Homo sapiens

<400> SEQUENCE: 14

His His His His His His
1               5

<210> SEQ ID NO 15
<211> LENGTH: 4
<212> TYPE: PRT
<213> ORGANISM: Homo sapiens

<400> SEQUENCE: 15

Glu Pro Lys Ser
1
```

METHODS FOR USING AND IDENTIFYING MODULATORS OF DELTA-LIKE 4

CROSS-REFERENCE TO RELATED APPLICATIONS

This application is a continuation-in-part of U.S. patent application Ser. No. 11/514,773, filed Sep. 1, 2006 which claims the benefit of U.S. Provisional Application Ser. No. 60/713,637, filed Sep. 1, 2005. This application also claims the benefit of U.S. Provisional Application Ser. No. 60/876,444, filed Dec. 20, 2006 and U.S. Provisional Application Ser. No. 60/901,754, filed Feb. 16, 2007. All the teachings of the above-referenced applications are incorporated herein by reference.

BACKGROUND OF THE INVENTION

Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis. More recently, it has become apparent that certain types of leukemia are also influenced by signaling involved in angiogenesis.

Agents that inhibit angiogenesis are useful in treating cancer. Avastin™ (bevacizumab), a monoclonal antibody that binds to Vascular Endothelial Growth Factor (VEGF), has proven to be effective in the treatment of a variety of cancers. Antagonists of the SDF/CXCR4 signaling pathway inhibit tumor neovascularization and are effective against cancer in mouse models (Guleng et al. Cancer Res. 2005 Jul. 1; 65(13):5864-71). The isocoumarin 2-(8-hydroxy-6-methoxy-1-oxo-1H-2-benzopyran-3-yl) propionic acid (NM-3) has completed phase I clinical evaluation as an orally bioavailable angiogenesis inhibitor. NM-3 directly kills both endothelial and tumor cells in vitro and is effective in the treatment of diverse human tumor xenografts in mice (Agata et al. Cancer Chemother Pharmacol. 2005 Jun. 10; [Epub ahead of print]).

Angiogenesis is a feature of other, non-neoplastic disorders. Various ocular disorders, particularly proliferative retinopathies and age-related macular degeneration, and inflammatory disorders, such as rheumatoid arthritis and psoriasis, are marked by increased vascularization of the affected tissue. Anti-angiogenic agents are effective for the treatment of these disorders. Macugen™, an aptamer that binds to VEGF has proven to be effective in the treatment of neovascular (wet) age-related macular degeneration. The success of TNF-alpha antagonists in the treatment of rheumatoid arthritis is partially attributed to anti-angiogenic effects on the inflamed joint tissue (Feldmann et al. Annu Rev Immunol. 2001; 19:163-96).

Arteriogenesis, a process related to but distinct from angiogenesis, occurs when the lumen of a pre-existing vessel increases to form a collateral. After myocardial infarction or peripheral ischemia (e.g., limb, kidney, etc.) arterioles become more significant conductance vessels in order to maintain blood flow after occlusion of the major artery serving the affected tissue. Thus, agents that promote arteriogenesis may be used to treat myocardial infarction and other ischemic events, and may also be used to prevent an ischemic event where a partial arterial occlusion is detected or suspected.

The Notch pathway, and particularly Notch1 and Notch4, participates in angiogenic processes. Notch signalling is generally involved in the regulation of processes as diverse as cellular proliferation, differentiation, specification and survival (Artavanis-Tsakonas et al., 1999). Its complexity in vertebrates is illustrated by the existence of multiple Notch receptor and ligands, each with distinct patterns of expression. In mammals there are four Notch receptors (notch1-4) and five ligands (jagged1, 2 and Dll1, 3 and 4). Mutations of Notch receptors and ligands in mice lead to abnormalities in various organs, from all three germ lines, including the vascular system (Iso et al., 2003). The Notch pathway functions through local cell interactions, the extracellular domain of the ligand, present on the surface of one cell, interacts with the extracellular domain of the receptor on an adjacent cell. This interaction allows the action of two ADAM proteases on the extracellular domain of Notch followed by the action of a γ-secretase on the transmembrane domain releasing the intracellular domain from the cell membrane and allowing it to be directed to the nucleus, where it functions with CSL to activate the expression of transcriptional repressors of the enhancer-of-split family (Mumm & Kopan, 2000).

Arterial versus venous differentiation has long been thought to be mainly dependent on physical factors such as blood pressure and oxygen concentration. Recently, however, the identification of a number of genes that are specifically expressed in arterial or venous endothelial cells well before the onset of circulation, seems to indicate an important role for genetic determination of endothelial cells in the primary differentiation events between arteries and veins. Among these genes are eph-B4, specifically expressed in venous endothelial cells (Adams et al., 1999) and ephrin-B2 (Adams et al., 1999; Gale et al., 2001), notch1 (Krebs et al., 2000), notch4 (Uyttendaele et al., 1996) and dll4 (Shutter et al., 2000), among others, which are specifically expressed in arterial endothelial cells.

Studies with mutations in zebrafish Notch homologues demonstrate the importance of this pathway in regulating the arterial versus venous endothelial differentiation, downstream of vascular endothelial growth factor and sonic-hedgehog and upstream of the ephrin pathway (Lawson et al., 2002), being the earliest genes expressed in an endothelial arterial specific fashion. There is mounting evidence, in both zebrafish and mouse, that Notch function is essential in the establishment of the arterial endothelial cell fate (Lawson et al., 2002; Fischer et al., 2004; Duarte et al., 2004).

It is a goal of the present disclosure to provide agents and therapeutic treatments for modulating angiogenesis, arteriogenesis and vessel identity.

SUMMARY OF THE INVENTION

In certain aspects, the disclosure provides uses for, and methods for identifying, agonists and antagonists of the Notch ligand Delta-like 4 (Dll4). Surprisingly, as taught herein, both agonists and antagonists of Dll4 may be used to treat tumors undergoing angiogenesis or in other situations where it is desirable to inhibit or disrupt angiogenesis. Furthermore, the disclosure provides methods for stimulating arteriogenesis by administering a Dll4 agonist. Arteriogenesis is the process of collateral artery formation and growth, typically in ischemic tissues. Thus Dll4 agonists may be used to treat patients suffering from, or at risk for, an ischemic event, such as a peripheral or coronary ischemia. The disclosure further relates to the discovery that upregulation of Dll4 causes endothelial cells to adopt an arterial identity, while inhibition of Dll4 causes endothelial cells to adopt a venous identity. Thus, the disclosure provides methods for altering venous or arterial identity by using, as appropriate an agonist or antagonist of Dll4. Additionally, the disclosure provides biomarkers that may be used to assess whether an agent of interest is an agonist or antagonist of Dll4 signaling.

In one embodiment, the disclosure describes a method for treating cancer comprising administering to a subject in need thereof, an effective amount of an antagonist of Dll4. This antagonist may be a polypeptide, particularly a peptide comprising an extracellular region of Dll4. In one aspect, the polypeptide may be a monomer, but may also function as a dimer. Merely to illustrate, examples of polypeptides that comprise the extracellular region of Dll4 may be selected from the DSL domain, a.a. 27-524, a.a. 1-486, a.a. 27-486, a.a. 1-442, and a.a. 27-442, or variants thereof, of SEQ ID NO: 1. Furthermore, a polypeptide may comprise at least one of, or a combination of, the following domains of Dll4: MNNL, DSL, EGF5, EGF5 (see FIG. 20A). Additionally, an antagonist of Dll4 may comprise an antibody, or a fragment thereof, that binds to an extracellular region of Dll4. Such an antibody may be monoclonal, human, or humanized. In a particular embodiment, said antibodies may comprise at least one of SEQ ID NOs: 4-7. All of the above-mentioned antagonists of Dll4 may be covalently joined to a moiety that confers enhanced pharmacokinetic properties as disclosed throughout herein. Particularly, the moiety may be selected from an Fc domain, His tag, or a polyoxyalkylene (e.g., PEG).

In another embodiment, antagonists of Dll4 stimulate, in a mammalian endothelial cell, at an effective concentration, expression of an arterial phenotype. Such a phenotype maybe be selected from, for example, expression of EphrinB2 and connexin37. Alternatively, antagonists of Dll4 inhibit, in a mammalian endothelial cell, at an effective concentration, expression of a venous phenotype. An example of such a phenotype may be the expression of EphB4. In addition, venous phenotypes may include the inhibition of Notch-regulated genes, such as Hey1, Hey2, Hes1 and Hes2.

The disclosure also provides methods for promoting the adoption of arterial characteristics in a blood vessel such as venous graft or saphenous vein graft. The method comprises administering to a subject in need thereof, an effective amount of a therapeutic polypeptide comprising an extracellular domain of Dll4. The polypeptides comprising an extracellular domain of Dll4 may be selected from the DSL domain, a.a. 27-524, a.a. 1-486, a.a. 27-486, a.a. 1-442, and a.a. 27-442 of SEQ ID NO: 1, all of which may be covalently linked to a moiety that confers enhanced pharmacokinetic properties as disclosed throughout herein. Particularly, the moiety may be selected from an Fc domain, His tag, or a polyoxyalkylene (e.g., PEG). Such therapeutic polypeptides may be a monomer or a dimer as described above.

In a further embodiment, the disclosure provides a method for inhibiting angiogenesis, the method comprising administering to a subject in need thereof, an effective amount of an antagonist of Dll4 signaling. However, in some aspects, this method is also useful for disrupting angiogenesis. That is, "inhibiting" angiogenesis may be defined not only as the prevention of vascular formation, but the prevention of functional vascular formation. The antagonist useful for angiogenesis inhibition may be a polypeptide, particularly a peptide comprising an extracellular region of Dll4. In one aspect, the polypeptide may be a monomer, but may also function as a dimer. Some examples of polypeptides that comprise the extracellular region of Dll4 may be selected from the DSL domain, a.a. 27-524, a.a. 1-486, a.a. 27486, a.a. 1442, and a.a. 27442, or variants thereof, of SEQ ID NO: 1. Furthermore, a polypeptide may comprise at least one of, or a combination of, the following domains of Dll4: MNNL, DSL, EGF5, EGF5 (see FIG. 20A). Additionally, an antagonist of Dll4 may comprise an antibody, or a fragment thereof, that binds to an extracellular region of Dll4. Such an antibody may be monoclonal, human, or humanized. In a particular embodiment, said antibodies may comprise at least one of SEQ ID NOs: 4-7. All of the above-mentioned antagonists of Dll4 may be covalently joined to a moiety that confers enhanced pharmacokinetic properties as disclosed throughout herein. Particularly, the moiety may be selected from an Fc domain, His tag, or a polyoxyalkylene (e.g., PEG). Some particular examples of Dll4-Fc conjugates are illustrated, by sequence, in FIG. 25.

Furthermore, any of the aforementioned antagonists of Dll4 signaling inhibit, in a mammalian endothelial cell, at an effective concentration, VEGF-stimulated angiogenesis, and may be administered to treat angiogenesis-associated disease. Examples of angiogenesis-associated diseases include angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, wound granulation, wound healing, telangiectasia psoriasis scleroderma, pyogenic granuloma, rubeosis, arthritis and diabetic neovascularization. Additionally, angiogenesis may be inhibited by further administering, either simultaneously or sequentially, at least one additional anti-angiogenesis agent that inhibits angiogenesis in an additive or synergistic manner with said antagonist. In a particular embodiment, said additional anti-angiogenesis agent may be an inhibitor of a Notch-receptor.

The disclosure further demonstrates that a monomeric polypeptide comprising a portion of the extracellular domain of Dll4 promotes angiogenesis at low concentrations and inhibits VEGF-mediated angiogenesis at higher concentrations. Soluble Dll4 polypeptide promotes arterialization or arteriogenesis at all concentrations. Accordingly, by selecting the appropriate dose of monomeric soluble Dll4 polypeptide, differing effects on angiogenesis may be achieved. In certain embodiments, a soluble Dll4 polypeptide comprises the DSL domain of SEQ ID NO:1 (amino acids 173-233) but lacks the transmembrane and intracellular portions (amino acids 552-685). Optionally, the Dll4 polypeptide comprises at least 200 amino acids in the region of amino acids 27-528 of SEQ ID NO:1. Optionally, the Dll4 polypeptide comprises amino acids 27-486 of SEQ ID NO:1 and preferably amino acids 27-524. In certain embodiments, the soluble Dll4 polypeptide includes a moiety that confers desirable pharmacokinetic properties, such as an Fc domain or a polyoxyalkylene moiety (e.g., PEG).

In certain embodiments, the disclosure provides methods for stimulating arteriogenesis. Such methods may comprise administering to a subject in need thereof, an effective amount of an agonist of Dll4 signaling. The subject may have or be at risk for an ischemic condition. The subject may have coronary artery disease, including, for example, angina or may have had a myocardial infarction. The subject may have a peripheral artery disease, such as an ischemic event or partial occlusion in a limb, the brain or an organ, such as the kidney. The subject may be diagnosed as being at risk for an ischemic event.

In certain embodiments, the disclosure provides methods for promoting the adoption of arterial characteristics in a blood vessel. Such a method may comprise administering to a blood vessel ex vivo or to a subject in need thereof, an effective amount of an agonist of Dll4 signaling. The blood vessel may be a venous graft, such as a saphenous vein graft.

In certain embodiments, the disclosure provides methods for disrupting angiogenesis. Such methods may comprise administering to a subject in need thereof, an effective amount of an agonist of Dll4 signaling.

In certain embodiments, the disclosure provides methods for disrupting tumor vasculature. Such methods may comprise administering to a subject in need thereof, an effective amount of an agonist of Dll4 signaling.

In certain embodiments, the disclosure provides methods for evaluating the effects of a test agent on Dll4 signaling. A method may comprise (a) contacting a cell of endothelial lineage with the test agent; and (b) detecting a phenotype associated with arterial or venous phenotype. A test agent that promotes the adoption of an arterial phenotype or an agent that inhibits the adoption of a venous phenotype is an agonist of Dll4 signaling, while a test agent that inhibits the adoption of an arterial phenotype or promotes the adoption of a venous phenotype is an antagonist of Dll4 signaling.

The disclosure provides characteristics that may be used to distinguish agonists and antagonists of Dll4 signaling. In general, agonists of Dll4 signaling stimulate, in a mammalian endothelial cell, expression of an arterial phenotype and inhibit expression of a venous phenotype. In general, antagonists of Dll4 signaling inhibit, in a mammalian endothelial cell, expression of an arterial phenotype and stimulate expression of a venous phenotype. Any known feature that distinguishes arterial and venous endothelial cells may be detected for the purpose of assessing arterial and venous phenotypes. For example, expression of EphrinB2 and expression of connexin37 may be used as indicators of arterial phenotype. As another example, expression of EphB4 may be used as an indicator of venous phenotype.

In certain aspects, the disclosure provides methods for inhibiting alpha smooth muscle actin (α-SMA) positive cell recruitment to a blood vessel, the method comprising, administering to a subject in need thereof, an effective amount of an inhibitor of Dll4 signaling. In certain embodiments, the inhibitor is selected from the group consisting of: an antibody to Dll4, a Dll4-His fusion or a Dll4-Fc fusion. In certain embodiments, the α-SMA positive cell is selected from the group consisting of: a pericyte, a smooth muscle cell, or a periendothelial cell. In certain embodiments, the blood vessel is a venous graft. In certain embodiments, the venous graft is a saphenous vein graft. In certain embodiments, the subject has an angiogenesis-associated disease. In certain embodiments, the angiogenesis-associated disease is selected from the group described above. In certain embodiments, the methods further include administering at least one additional anti-angiogenesis agent that inhibits angiogenesis in an additive or synergistic manner with the inhibitor of Dll4 signaling.

In further aspects, the disclosure provides compositions of isolated monoclonal antibodies or antigen binding portion that binds to an epitope that is situated in the extracellular portion of Dll4. Examples of epitopes situated in the extracellular portion of Dll4 include the MNNL and DSL domains, as well as any one or more of the EGF repeats as illustrated in FIG. 20A. Without limitation, such antibodies may comprise any one of SEQ ID NOs: 4-7. Said antibodies may further be humanized antibodies.

BRIEF DESCRIPTION OF THE DRAWINGS

FIG. 1 shows the amino acid sequence of the human Delta-like 4 protein (SEQ ID NO:1; GenBank NP_061947). The signal sequence, amino acids 1-26, is underlined. The transmembrane domain, amino acids 532-552, is bolded. The extracellular domain of the mature protein is amino acids 27-531, although imprecision in signal peptide processing may result in a protein that is slightly longer or shorter. The intracellular domain is amino acids 532-685.

FIG. 2 shows the nucleic acid sequence (cDNA) encoding the human Delta-like 4 protein (SEQ ID NO:2; GenBank NM_019074). The coding sequence is nucleic acids 321-2378.

FIG. 6. PECAM1 immunostaining in cryosections and microangiography. (a-g) serial sections of a E9.5 dt embryo (anterior-posterior) showing fusion between the aorta (upper right arrow) and the ACV (upper left arrow) just prior to its connection to the sinus venosus (lower arrow). In section (a) the ACV consists of a plexus of small capillaries (upper left arrow) which join to form a single vessel with a large lumen just prior to its fusion with the dorsal aorta. Section (e) shows the aortic atrophy in regions posterior to the sinus venosus. (f,g) serial sections of a E9.5 wild type embryo depicting the same regions stated above. Microangiography with India ink injection confirmed the existence of functional connections between the dorsal aortae and the ACV of dt embryos (i), with ink flowing directly from the aortae (left hand arrow) to the sinus venosus (right hand arrow), in contrast to the regular flow observed in the control embryos (h).

FIG. 15. Dll4+/− mutant mice show defective increase in vascular proliferation: (A) The vasculature of wild type and Dll4+/− embryos were examined using PECAM wholemount immunostaining. Dorsal aorta and cardinal vein are labeled a and v. Absence of large vessels and an increase in vessel branching and density was seen in Dll4+/− embryos at E10.5 compared to wild type. (B) Vascular response in Dll4+/− adult mice was examined as in (A) after tumor implantation. Wild type mice showed organized vascular proliferation in the tumor (left half), while mutant mice showed markedly increased vascular response which lacks organization and vascular hierarchy. (C) Expression of Dll4 in tumor and normal regions in Dll4+/− mutant mice was examined by β-gal staining. Dll4 expression was observed in a few discrete vessels in the normal tissue, while the tumor region showed many β-gal positive vessels of similar appearance indicative of Dll4 induction in tumor vessels. (D) Pericyte coverage around newly forming vessels was examined by α-SMA localization. In wild type mice, the vessels showed co-localization of PECAM and α-SMA (left panel). In Dll4+/− mice tumor vessels however, the number of α-SMA positive cells lining the endothelial cells was profoundly reduced (right panel). (E) Dll4 is activated in most but not all vessels in the tumor. β-gal (left panel) and PECAM immuno-staining (right panel) of adjacent tumor sections show that endothelial specific PECAM staining is more abundant that lacZ Dll4-reporter expression.

FIG. 16. Biochemical properties of sDll4: (A) Notch-Fc fusion protein was coated directly on ELISA plates. sDll4-AP was allowed to bind Notch-Fc and the bound Dll4 was quantitated by the addition of AP substrate. sDll4-AP bound efficiently to Notch 1 and not Notch 3 (left panel). Binding of sDll-4Fc and sDll4-His to Notch 1 was examined. (B) HUVEC cells were transfected with expression vectors for sDll4-Fc, sDll4-His or vector alone. Notch responsive Hes-2 gene expression was not induced by sDll4 proteins. (C) Notch activation measured by the induction in Hes-1, Hey-1 and Hes-2 when HUVEC cells were co-cultivated with choK expressing Dll4-FL (full length). Addition of recombinant sDll4-Fc and sDll4-His reduced the induction of Notch responsive genes. Two independent experiments produced similar results.

FIG. 17. sDll4 induces vessel response but lack perfusion in murine Matrigel assay: (A) Matrigel was injected subcutaneously into Balb/C nu/nu nice. After 6 days, plugs were removed and processed in paraffin. Individual sections were stained with H&E and representative photographs at ×20 magnification from triplicate plugs in 2 independent experiments are shown. (B) Matrigel plugs were stained for PECAM. Photomicrographs were taken with a Nikon Coolpix 5000 camera on a Nikon Eclipse E400 microscope with a 4×/0.13 NA objective and a 10× eyepiece. Quantitation of vascularized area averaged (±SEM) from all plugs (Scion Image software) in bar graph. P value <0.01.

FIG. 21. Protein sequence alignment of human Dll4 (hDll4) (SEQ ID NO: 8), mouse Dll4 (mDll4) (SEQ ID NO: 9), and human Dll1 (hDll1) (SEQ ID NO: 10). From N terminus to C terminus, first shaded region indicates the epitope for antibody clone #2-6. Second shaded region represents the DSL region. Third shaded region, which comprises EGF-like 3 (E3) domain, indicates the epitope for antibody clone #61B.

FIG. 22. Characterization of anti-Dll4 antibodies: (A). Human Dll4 antibodies were raised in mouse by immunization with soluble human Dll4-His protein (aa 1-524 of SEQ ID NO: 1). Four antibody clones are summarized. (B). Two antibody clones designated #2-6 and #61B efficiently neutralize Dll4-Notch1 interaction. Coat 0.5 ug/ml (100 ul) Notch1-Fc on ELISA plate overnight in PBS at 4° C. Block the plate with 0.5% BSA for 2 hours, and then add indicated amount of Dll4 antibodies premixed with 50 ng soluble Dll4 fused with alkaline phosphatase. After 45 min incubation at room temperature, the plate is washed with PBST and incubated with PNPP at 37° C. for 1.5 hours. This experiment has been repeated at least three times.

FIG. 23. Sequence identifying the variable regions $V_H$ (SEQ ID NO: 4) and $V_L$ (SEQ ID NO: 5) of Dll4 antibody clone designated #61B.

FIG. 24. Sequence identifying the variable regions $V_H$ (SEQ ID NO: 6) and $V_L$ (SEQ ID NO: 7) of Dll4 antibody clone designated #2-6.

DETAILED DESCRIPTION OF THE INVENTION

Figure 3:
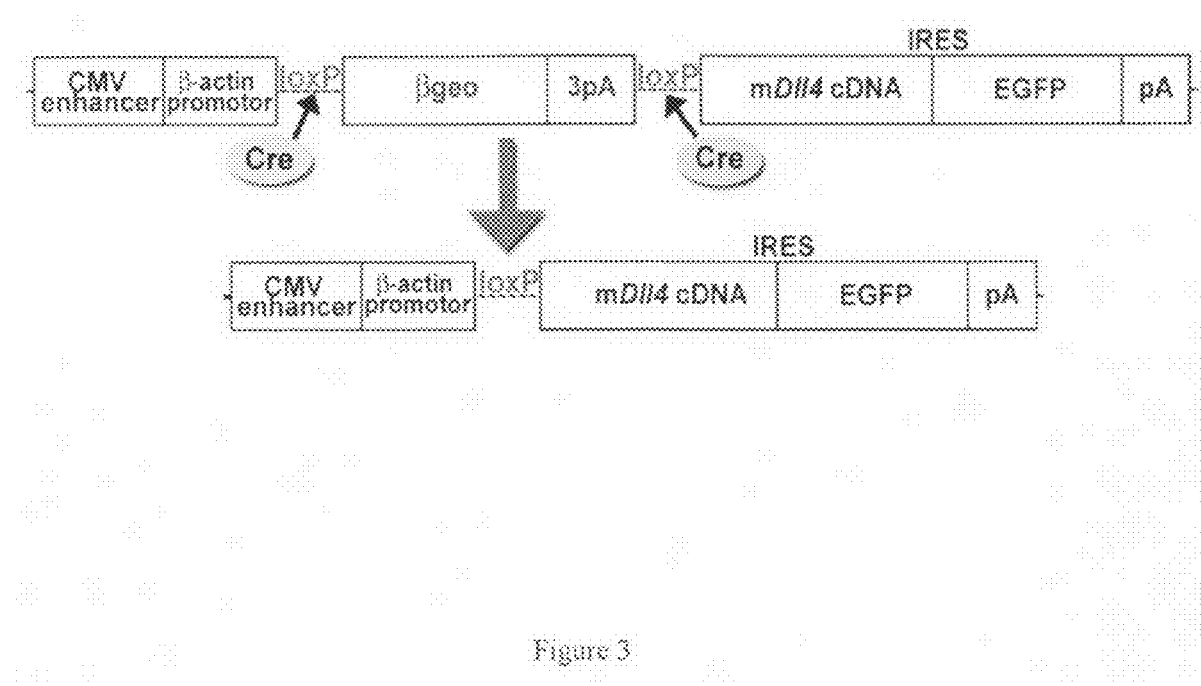
FIG. 3 shows pZ/EG-mDll4 transgenesis vector and result of Cre activity.
Figure 4:
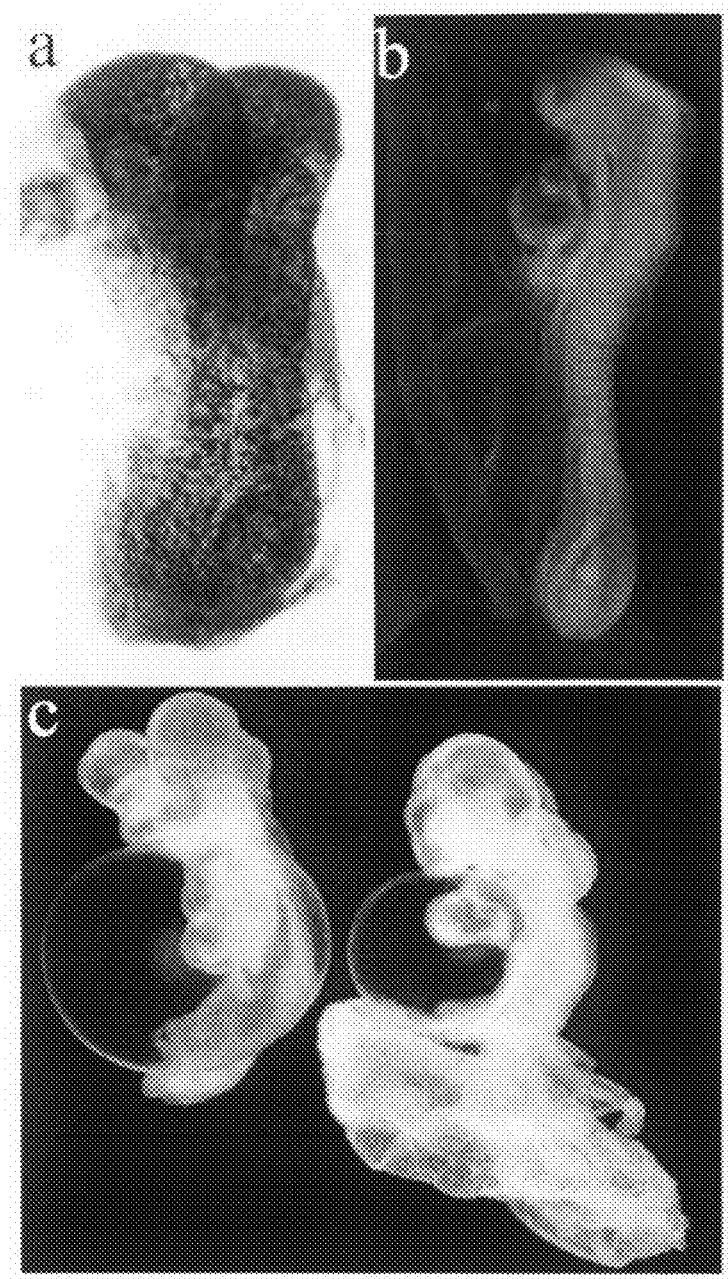
FIG. 4. (a) LacZ staining of a ZEG-mDll4 embryo at E8.0; (b) EGFP expression in the dt embryos at E8.5. (c) haemorrhaging and pericardial edema in dt embryos at E9.0.
Figure 5:
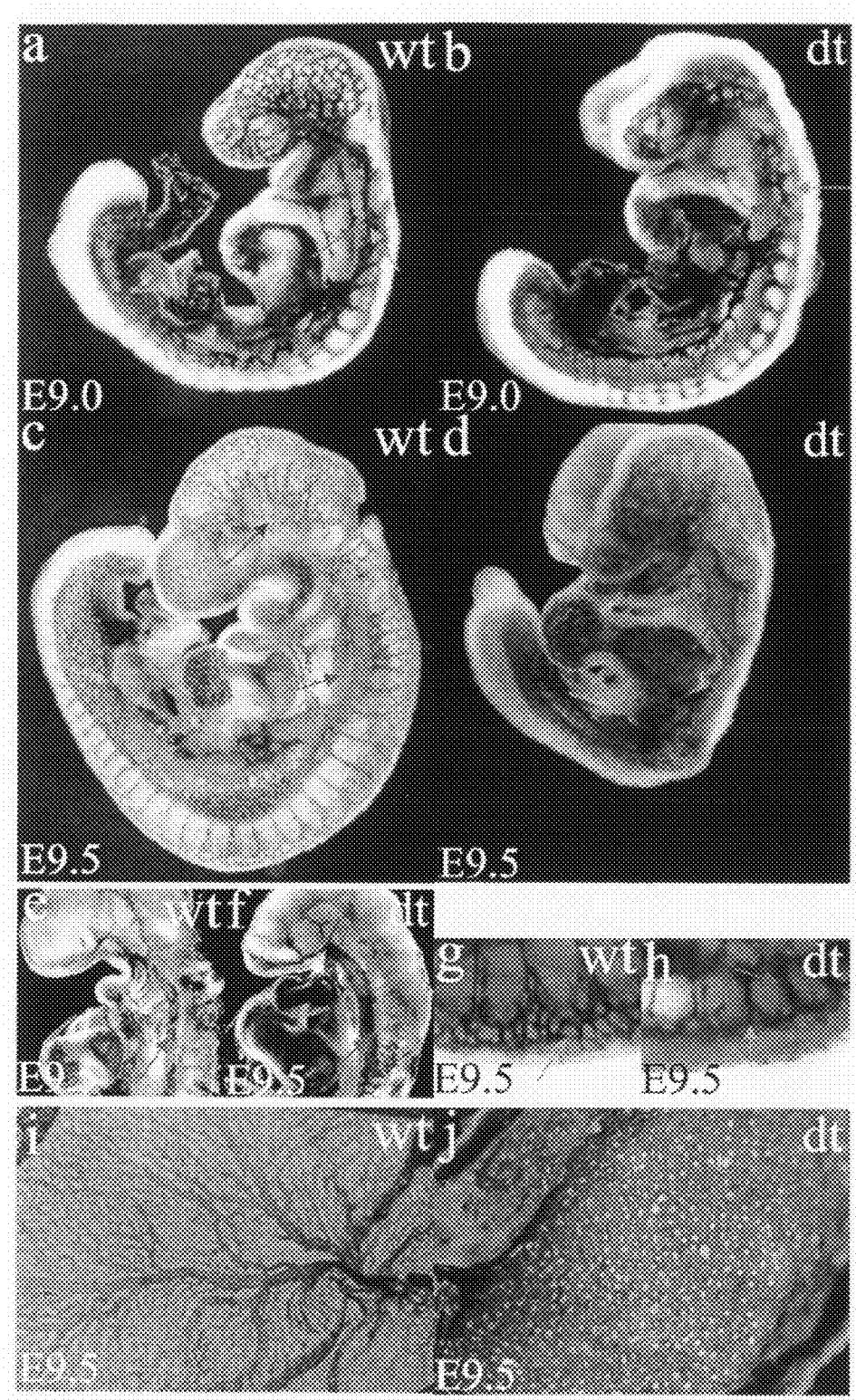
FIG. 5. Wholemount PECAM1 immunostaining of E9.0 and E9.5 dt and control embryos. (a) control embryo at E9.0, (b) dt embryo at E9.0 showing a hypertrophied dorsal aorta (lower left arrow), ramified ACV (lower right arrow) and an immature vascular plexus in the head region (upper arrow) (c) control embryo at E9.5, (d) dt embryo at E9.5 showing hypertrophied dorsal aorta and almost no sign of an ACV, immature vascular plexus in the head region and hypertrophied sinus venosus and heart ventricle. Half sectioning the stained embryos at E9.5 showed that the aorta of the dt embryos (f) atrophies just posterior to its connection to the sinus venosus (lower arrow), while in the control embryo (e) remains with the same calibre throughout the embryo. The intersomitic vessels (upper arrow) of the dt embryos (h) appear slightly dilated and shorter than those of control embryos (g). In the dorsal region (lower arrow) of the dt embryos angiogenesis fails to occur. (i) yolk sac of a E9.5 control embryo, (j) yolk sac of a dt embryo showing lack of remodelling of the primary plexus in contrast to the highly organized structure of the vasculature in the control embryos.

The current invention is based in part on the discovery that Delta-like 4 function is essential for angiogenesis in vivo, and, moreover, that an increase of Delta-like 4 activity is associated with increased proliferation of arterial endothelial cells and an increased adoption of an arterial identity by endothelial cells. Applicants generated mouse Dll4 knockout mutations that evinced dosage sensitive defects in angiogenesis. Furthermore, Applicants generated Dll4 overexpression models in mouse and demonstrated that increased expression of Dll4 causes, in some instances, hypertrophy of arterial tissue and, moreover, causes venous tissue to adopt an arterial identity. Based on these results, it is apparent that angiogenesis, in which a system of arterial and venous microvessels is generated, is highly sensitive to Dll4 activity and may be perturbed (e.g., inhibited or caused to occur in a disorganized or ineffective manner) by inhibition or hyperactivation of Dll4. Thus, surprisingly, both agonists and antagonists of Dll4 may be used to treat tumors undergoing angiogenesis. Furthermore, the invention relates to the discovery that overexpression of Dll4 can stimulate arterial growth, and may therefore be used to stimulate arteriogenesis. Arteriogenesis is the process of collateral artery formation and growth, typically in ischemic tissues. Thus Dll4 agonists may be used to treat patients suffering from, or at risk for, an ischemic event, such as a peripheral or coronary ischemia. Furthermore, the disclosure demonstrates that a soluble monomeric or dimeric Dll4 polypeptide can act to inhibit or promote angiogenesis at low or high concentrations, respectively.

Dll4 Agonist/Antagonist Determinant

The invention further relates to biomarkers that may be used to assess whether an agent of interest is an agonist or antagonist of Dll4 signaling. The scientific literature relating to Delta proteins generally, including Dll4, provides no clarity as to whether a particular agent activates or inhibits Dll4-mediated signaling. For example, Dll4 and Delta extracellular domains (e.g., soluble monomeric or dimeric forms, forms with deleted intracellular domains, and soluble Fc fusions) have been tested in a variety of assays and it remains unclear whether any of the observed effects are due to agonist or antagonist activity, or whether there is any meaningful activity at all. Moreover, reagents may affect Dll4 signaling in a variety of ways. For example, a reagent may affect Notch 1 and/or Notch 4 activation, or activation of retrograde Dll4 signaling, possibly mediated by the Dll4 intracellular domain. A reagent may also affect the activity of presenilin protease activity, which may affect both Notch1 and Notch4. The present disclosure demonstrates that Dll4 hyperactivation causes endothelial cells to adopt an arterial phenotype, typified by expression of EphrinB2 and connexin37, while Dll4 loss of function causes endothelial cells to adopt a venous identity, typified by expression of EphB4. This information about the genetically-determined, in vivo effects of Dll4 activity will permit the identification of both known and newly discovered agents as agonists or antagonists of Dll4 signaling.

Agents

Accordingly, in certain aspects, the disclosure provides numerous polypeptide compounds (agents) that may be used to treat cancer as well as angiogenesis related disorders and unwanted angiogenesis related processes.

Dll4 is a Notch ligand and contains a signal sequence, a DSL domain, eight epidermal growth factor-like repeats, a transmembrane domain, and an intracellular region, all of which are characteristics of members of the Delta protein family. The tissue distribution of Delta-4 mRNA resembles that previously described for Notch-4 (Int-3) transcripts. Soluble forms of the extracellular portion of Delta-4 inhibit the apparent proliferation of human aortic endothelial cells, but not human pulmonary arterial endothelial cells. Yoneya et al. J. Biochem. Vol. 129, pp. 27-34 (2001).

Members of the Notch family of proteins are transmembrane receptors that contain characteristic multiple epidermal growth factor (EGF)-like repeats as well as conserved domains such as RAM, ankyrin-like repeat, and PEST sequences. Ligands for Notch proteins include Delta and Serrate in *Drosophila melanogaster*, LAG-2 and APX-1 in *Caenorhabditis elegans*, and Delta and Serrate (or Jagged) in vertebrates. These ligands are also transmembrane proteins and contain a highly conserved DSL (Delta-Serrate-LAG-2) motif upstream of a variable number of EGF-like repeats. The DSL domain is a characteristic feature of Notch ligands and is important for protein function; thus, point mutation of the DSL domain in LAG-2-results in a loss of activity. Although the Delta and Jagged (Serrate) proteins of vertebrates exhibit similar structures, each group of proteins also possesses several distinct features. Thus, whereas vertebrate Delta proteins contain eight EGF-like repeats, Jagged proteins contain 16 such repeats. Furthermore, the EGF domains are followed by a cysteine-rich domain in Jagged proteins but not in Delta proteins. However, the consequences of these structural differences remain unclear.

Uyttendaele et al. (1996) cloned cDNAs corresponding to the complete coding region of the mouse Notch4 gene. In situ hybridization revealed that Notch4 transcripts are primarily restricted to endothelial cells in embryonic and adult life, suggesting a role for Notch4 during development of vertebrate endothelium.

Li et al. (Genomics. 1998 Jul. 1; 51(1):45-58) reported that the human NOTCH4 gene contains 30 exons and spans approximately 30 kb. They isolated cDNAs corresponding to 6.7-kb NOTCH4(S) and 9.3-kb NOTCH4(L) mRNA isoforms. The predicted protein encoded by NOTCH4(S) is 2,003 amino acids long and contains the characteristic Notch motifs: a signal peptide, 29 epidermal growth factor (EGF)-like repeats, 3 Notch/lin-12 repeats, a transmembrane region, 6 cdc10 (603151)/ankyrin repeats, and the PEST conserved region at the C terminus. The sequences of the mouse and human NOTCH4 proteins are 82% identical. The incompletely spliced NOTCH4(L) cDNA potentially encodes 2 different proteins. One consists of the first 7 EGF repeats. The second contains the transmembrane domain and intracellular region and is similar to the mouse int3 protooncoprotein. Northern blot analysis revealed that NOTCH4(S) is the major transcript and is expressed in a wide variety of tissues.

Krebs et al. (2000) generated Notch4-deficient mice by gene targeting. Embryos homozygous for this mutation developed normally, and homozygous mutant adults were viable and fertile. However, the Notch4 mutation displayed genetic interactions with a targeted mutation of the related Notch1 gene. Both Notch1 mutant and Notch1/Notch4 double mutant embryos displayed severe defects in angiogenic vascular remodeling. Analysis of the expression patterns of genes encoding ligands for Notch family receptors indicated that only the Dll4 gene is expressed in a pattern consistent with that expected for a gene encoding a ligand for the Notch1 and Notch4 receptors in the early embryonic vasculature. Therefore, there is an essential role for the Notch signaling pathway in regulating vascular morphogenesis and remodeling, and indicate that whereas the Notch4 gene is not essential during embryonic development, the Notch4 and Notch1 genes have partially overlapping roles during embryogenesis in mice.

As noted above, the disclosure provides methods for using and identifying agonists and antagonists of Dll4 signaling. Candidate agonists and antagonists will generally be any antibody that binds to, or soluble portions of, proteins involved in the Dll4 signaling pathway, including, for example, Dll4, Notch1, Notch4 and presenilin. Candidate agonists and antagonists may also be small molecules or other agents that bind to or effect members of the pathway. Antisense or RNAi nucleic acids may be used as antagonists of Dll4, Notch1, Notch4 or presenilin or other members of the signaling pathway.

Examples of agents include:
(a) an antibody that binds selectively to Dll4;
(b) an antibody that binds selectively to Notch 1;
(c) an antibody that binds selectively to Notch4;
(d) an antibody that binds to Notch1 and Notch4;
(e) a polypeptide monomer comprising a Notch-receptor binding portion of Dll4;
(f) a polypeptide dimer comprising a Notch-receptor binding portion of Dll4;
(g) a polypeptide multimer comprising two or more polypeptides comprising a Notch-receptor binding portion of Dll4;
(h) a polypeptide monomer comprising a Dll4-binding portion of Notch1 or Notch4;
(i) a polypeptide multimer comprising two or more polypeptides comprising a Dll4-binding portion of Notch 1 or Notch4.

Agents that interfere with presenilin activity or other metalloproteinases (e.g., kuzbanian) are expected to modulate Dll4 signaling. Each of these agents may be assessed for agonist or antagonist activity as described herein.

Dll4 Polypeptides

In certain aspects, the agent is a soluble polypeptide comprising an extracellular domain of a Dll4 protein, e.g., as shown in amino acids 27-531 of SEQ ID NO:1. In a specific embodiment, the Dll4 soluble polypeptide comprises a DSL domain of a Dll4 protein. In another embodiment, the Dll4 soluble polypeptide is a truncate comprising at least domains 5 or 6 of the EGF-like domains.

As used herein, the subject soluble polypeptides include fragments, functional variants, and modified forms of Dll4 soluble polypeptide. These fragments, functional variants, and modified forms of the subject soluble polypeptides may be tested for activity as agonists or antagonists of Dll4 by assessing effects on arterial or venous phenotype in endothelial cells.

In certain embodiments, isolated fragments of the subject soluble polypeptides can be obtained by screening polypeptides recombinantly produced from the corresponding fragment of the nucleic acid encoding an Dll4. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can modulate Dll4 signaling.

In certain embodiments, a functional variant of an Dll4 soluble polypeptide comprises an amino acid sequence that is at least 90%, 95%, 97%, 99% or 100% identical to residues 27-531 of the amino acid sequence of SEQ ID NO:1.

In certain embodiments, the present invention contemplates making functional variants by modifying the structure of the subject soluble polypeptide for such purposes as enhancing therapeutic or prophylactic efficacy, or stability (e.g., ex vivo shelf life and resistance to proteolytic degradation in vivo). Modified soluble polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

This invention further contemplates a method of generating sets of combinatorial mutants of the Dll4 polypeptides, as well as truncation mutants, and is especially useful for identifying functional variant sequences. The purpose of screening such combinatorial libraries may be to generate, for example, soluble polypeptide variants which can act as agonists or antagonists of Dll4. Combinatorially-derived variants can be generated which have a selective potency relative to a naturally occurring soluble polypeptide. Such variant proteins, when expressed from recombinant DNA constructs, can be used in gene therapy protocols. Likewise, mutagenesis can give rise to variants which have intracellular half-lives dramatically different than the corresponding wild-type soluble polypeptide. For example, the altered protein can be rendered either more stable or less stable to proteolytic degradation or other cellular process which result in destruction of, or otherwise inactivation of the protein of interest (e.g., a soluble polypeptide). Such variants, and the genes which encode them, can be utilized to alter the subject soluble polypeptide levels by modulating their half-life. A short half-life can give rise to more transient biological effects and, when part of an inducible expression system, can allow tighter control of recombinant soluble polypeptide levels within the cell. As above, such proteins, and particularly their recombinant nucleic acid constructs, can be used in gene therapy protocols.

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential soluble polypeptide sequences. The synthesis of degenerate oligonucleotides is well known in the art (see for example, Narang, S A (1983) *Tetrahedron* 39:3; Itakura et al., (1981) Recombinant DNA, Proc. 3rd Cleveland Sympos. Macromolecules, ed. A G Walton, Amsterdam: Elsevier pp 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *PNAS USA* 89:2429-2433; Devlin et al., (1990) *Science* 249: 404-406; Cwirla et al., (1990) *PNAS USA* 87: 6378-6382; as well as U.S. Pat. Nos. 5,223,409, 5,198,346, and 5,096,815).

Alternatively, other forms of mutagenesis can be utilized to generate a combinatorial library. For example, soluble polypeptide variants (e.g., the antagonist forms) can be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137: 109-118; Grodberg et al., (1993) *Eur. J. Biochem.* 218:597-601; Nagashima et al., (1993) *J. Biol. Chem.* 268:2888-2892; Lowman et al., (1991) *Biochemistry* 30:10832-10838; and Cunningham et al., (1989) *Science* 244:1081-1085), by linker scanning mutagenesis (Gustin et al., (1993) *Virology* 193: 653-660; Brown et al., (1992) *Mol. Cell. Biol.* 12:2644-2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11-19); or by random mutagenesis, including chemical mutagenesis, etc. (Miller et al., (1992) *A Short Course in Bacterial Genetics*, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying truncated (bioactive) forms of the subject soluble polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the subject soluble polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the soluble polypeptides of the invention may further comprise post-translational modifications. Such modifications include, but are not limited to, acetylation, carboxylation, glycosylation, phosphorylation, lipidation, and acylation. As a result, the modified soluble polypeptides may contain non-amino acid elements, such as polyethylene glycols, lipids, poly- or mono-saccharide, and phosphates. Effects of such non-amino acid elements on the functionality of a soluble polypeptide may be tested for its agonist or antagonist effects on Dll4.

In certain aspects, functional variants or modified forms of the subject soluble polypeptides include fusion proteins having at least a portion of the soluble polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Another fusion domain well known in the art is green fluorescent protein (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the soluble polypeptides of the present invention contain one or more modifications that are capable of stabilizing the soluble polypeptides. For example, such modifications enhance the in vitro half life of the soluble polypeptides, enhance circulatory half life of the soluble polypeptides or reducing proteolytic degradation of the soluble polypeptides.

In certain embodiments, soluble polypeptides (unmodified or modified) of the invention can be produced by a variety of art-known techniques. For example, such soluble polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the soluble polypeptides, fragments or variants thereof may be recombinantly produced using various expression systems as is well known in the art (also see below).

Gene Therapy

In certain aspects, the invention relates to isolated and/or recombinant nucleic acids encoding a Dll4 polypeptide. The subject nucleic acids may be single-stranded or double-stranded, DNA or RNA molecules. These nucleic acids are useful as therapeutic agents. For example, these nucleic acids are useful in making recombinant soluble polypeptides which are administered to a cell or an individual as therapeutics. Alternative, these nucleic acids can be directly administered to a cell or an individual as therapeutics such as in gene therapy.

In certain embodiments, the invention provides isolated or recombinant nucleic acid sequences that are at least 80%, 85%, 90%, 95%, 97%, 98%, 99% or 100% identical to a region of the nucleotide sequence depicted in SEQ ID NO:2. One of ordinary skill in the art will appreciate that nucleic acid sequences complementary to the subject nucleic acids, and variants of the subject nucleic acids are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence depicted in SEQ ID NO:2, or complement sequences thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the subject nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspect of the invention, the subject nucleic acid is provided in an expression vector comprising a nucleotide sequence encoding a Dll4 polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene including a coding sequence for one or more of the subject soluble polypeptide. The host cell may be any prokaryotic or eukaryotic cell. For example, a soluble polypeptide of the invention may be expressed in bacterial cells such as *E. coli*, insect cells (e.g., using a baculovirus expression system), yeast, or mammalian cells. Other suitable host cells are known to those skilled in the art.

Method of Producing Soluble Polypeptide

Accordingly, the present invention further pertains to methods of producing the subject soluble polypeptides. For example, a host cell transfected with an expression vector encoding a Dll4 soluble polypeptide can be cultured under appropriate conditions to allow expression of the Dll4 soluble polypeptide to occur. The Dll4 soluble polypeptide may be secreted and isolated from a mixture of cells and medium containing the soluble polypeptides. Alternatively, the soluble polypeptides may be retained cytoplasmically or in a membrane fraction and the cells harvested, lysed and the protein isolated. A cell culture includes host cells, media and other byproducts. Suitable media for cell culture are well known in the art. The soluble polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the soluble polypeptides. In a preferred embodiment, the soluble polypeptide is a fusion protein containing a domain which facilitates its purification.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant soluble polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

Antibody

In certain aspects, the present invention provides antibodies that have agonist or antagonist effects on Dll4 signaling. Such antibodies may bind to antigens such as Dll4, Notch1 or Notch4. Preferably, the antibody binds to an extracellular domain of such antigens. It is understood that antibodies may be polyclonal or monoclonal; intact or truncated, e.g., F(ab')2, Fab, Fv; xenogeneic, allogeneic, syngeneic, fully human or modified forms thereof, e.g., humanized, chimeric. Fully human antibodies may be selected from transgenic animals that express human immunoglobulin genes or assembled from recombinant libraries expressing antibody fragments.

For example, by using immunogens derived from Dll4, Notch1 or Notch4, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the peptide. (e.g., a polypeptide or an antigenic fragment which is capable of eliciting an antibody response, or a fusion protein). Techniques for conferring immunogenicity on a protein or peptide include conjugation to carriers or other techniques well known in the art. An immunogenic portion of an antigen can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature*, 256: 495-497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with Dll4, Notch1, Notch4 or other target polypeptide and monoclonal antibodies isolated from a culture comprising such hybridoma cells.

The term "antibody" as used herein is intended to include fragments thereof which are also specifically reactive with antigen. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for antigen conferred by at least one CDR region of the antibody. Techniques for the production of single chain antibodies (U.S. Pat. No. 4,946,778) can also be adapted to produce single chain antibodies. Also, transgenic mice or other organisms including other mammals, may be used to express humanized antibodies. In preferred embodiments, the antibodies further comprise a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to Dll4, Notch1 or Notch4 may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody. The monoclonal antibody may be purified from the cell culture.

In certain embodiments, the disclosure provides humanized versions of any of the antibodies disclosed herein, as well as antibodies and antigen binding portions thereof that comprise at least one CDR portion derived from an antibody disclosed herein, particularly the CDR3. In preferred embodiments, the antibody is a monoclonal antibody that is immunocompatible with the subject to which it is to be administered, and preferably is clinically acceptable for administration to a human.

In certain embodiments, single chain antibodies, and chimeric, humanized or primatized (CDR-grafted) antibodies, as well as chimeric or CDR-grafted single chain antibodies, comprising portions derived from different species, are also encompassed by the present invention as antigen binding portions of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125, 023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946, 778; and Bird, R. E. et al., Science, 242: 423-426 (1988)), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Preferred functional fragments retain an antigen binding function of a corresponding full-length antibody (e.g., specificity for Dll4). Certain preferred functional fragments retain the ability to inhibit one or more functions characteristic of Dll4, such as a binding activity, a signaling activity, and/or stimulation of a cellular response.

Figure 20:
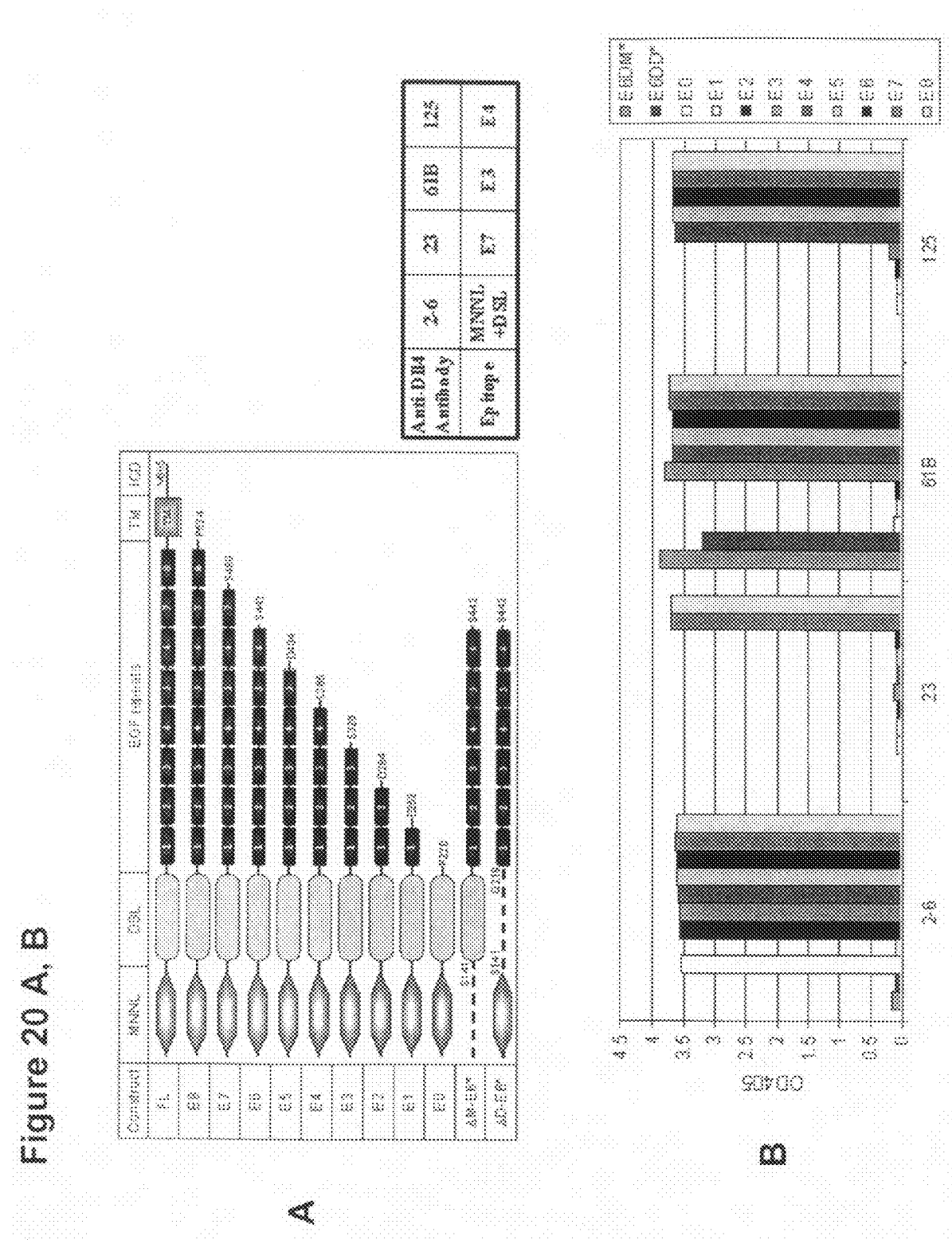
FIG. 20. Epitope mapping of anti-Dll4 antibodies: (A). Illustration of a complete set of Dll4 truncation mutants fused to alkaline phosphatase. Four individual clones were identified, each with a specific binding region to Dll4. (B). Coat 4 ug/ml (100 ul) Dll4 antibodies on ELISA plate overnight in PBS at 4° C. Block the plate with 0.5% BSA for 2 hours, and then add 20 ng of soluble Dll4 proteins fused with alkaline phosphatase. After 45 min incubation at room temperature, the plate is washed with PBST and incubated with PNPP at 37° C. for 20 min. This experiment has been repeated at least three times.
Figure 25:
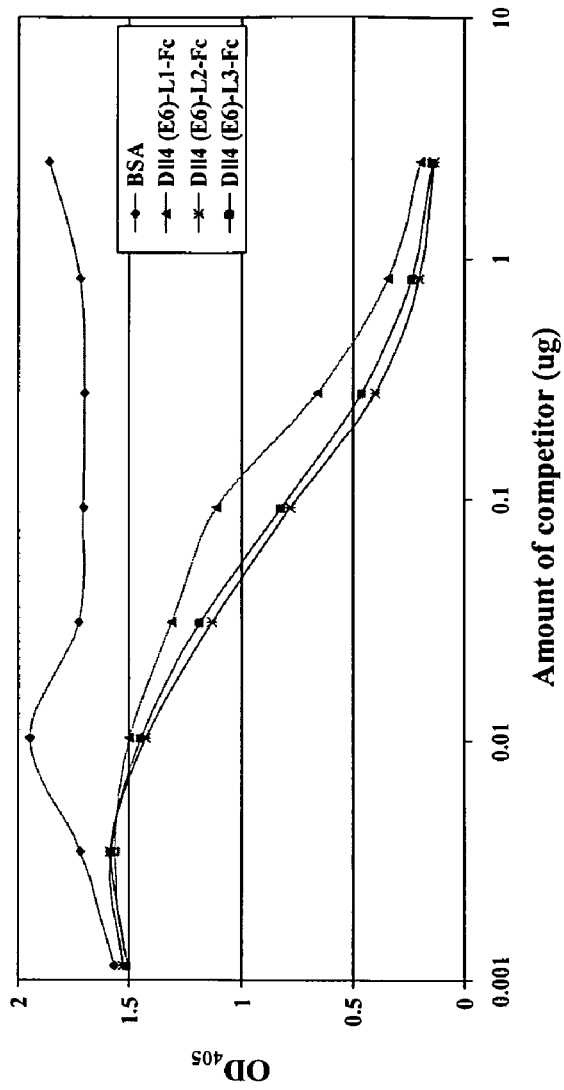
FIG. 25. Dll4-Fc fusion protein linker engineering. The linker region between fusion proteins may affect the function of protein of interest. Three different linkers between Dll4 (E6) and human IgG1 Fc (starts at EPKS in Fc hinge region) were tested. Linker1 (L1) has the sequence of SEQ ID NO: 11. Linker2 (L2) has the sequence of SEQ ID NO: 12. Linker3 (L3) has the sequence of SEQ ID NO: 13. There is a threefold-difference between L1 and L2 fusion proteins. Dll4-L2-Fc was chosen for tumor xenograft study. ELISA plate was coated with 0.5 ug/ml (100 ul) Notch1-Fc in PBS at 4° C. for overnight, and then blocked with 0.5% BSA for 2 hours. Indicated amount of Dll4-Fc proteins or BSA were premixed with 50 ng Dll4 (E8)-AP and then added. After 45 min incubation at room temperature, the plate was washed with PBST and incubated with PNPP at 37 C for 1 hour.

As shown in the Examples below, Applicants have generated monoclonal antibodies against Dll4 as well as hybridoma cell lines producing Dll4 monoclonal antibodies. These antibodies were further characterized in many ways, such as, their ability to inhibit interaction between Dll4 and Notch and their cross-reactivity. Further, epitope mapping studies reveals that these Dll4 antibodies may specifically bind to one or more regions of Dll4. For example, as illustrated in FIG. 21, the antibody clone designated #2-6 binds to a region that spans an area that includes the MNNL domain, while a clone designated #61B binds to a region that includes the EGF-like 3 domain. Other antibody clones that have been identified bind to other EGF-like domains, as shown in FIG. 20A.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

Antisense and RNAi

In certain aspects, the disclosure provides isolated nucleic acid compounds comprising at least a portion that hybridizes to a Dll4 transcript under physiological conditions and decreases the expression of Dll4 in a cell. Such nucleic acids may be used as Dll4 antagonists, as described herein. The Dll4 transcript may be any pre-splicing transcript (i.e., including introns), post-splicing transcript, as well as any splice variant. In certain embodiments, the Dll4 transcript has a sequence corresponding to the cDNA set forth in SEQ ID NO:2, and particularly the coding portion thereof. In certain aspects, the disclosure provides isolated nucleic acid compounds comprising at least a portion that hybridizes to a Notch1 or Notch4 transcript under physiological conditions and decreases the expression of Notch 1 or Notch4 in a cell. These may be used as Dll4 antagonists also. The Notch1 or Notch4 transcript may be any pre-splicing transcript (i.e., including introns), post-splicing transcript, as well as any splice variant.

Examples of categories of nucleic acid compounds include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50 nucleotides of the Dll4, Notch1 or Notch4 nucleic acid sequence. The region of complementarity will preferably be at least 8 nucleotides, and optionally at least 10 or at least 15 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on cellular phenotypes, such as arterial or venous identity.

Methods of Screening/Assays

There are numerous approaches to screening for candidate agents that act as agonists or antagonists of Dll4 signaling. The disclosure provides characteristics that may be used to distinguish agonists and antagonists of Dll4 signaling. In general, agonists of Dll4 signaling stimulate, in a mammalian endothelial cell, expression of an arterial phenotype and inhibit expression of a venous phenotype. In general, antagonists of Dll4 signaling inhibit, in a mammalian endothelial cell, expression of an arterial phenotype and stimulate expression of a venous phenotype. Any known feature that distinguishes arterial and venous endothelial cells may be detected for the purpose of assessing arterial and venous phenotypes. For example, expression of EphrinB2 and expression of connexin37 may be used as indicators of arterial phenotype. As another example, expression of EphB4 may be used as an indicator of venous phenotype.

Agents may also be screened for binding activity to Dll4, Notch1 or Notch4, or for the ability to stimulate or inhibit the production of the active intracellular domain of Notch1 (NICD), Notch4 or Dll4. Expression from hairy/enhancer of split (HES) sensitive promoters may also be useful in determining whether Notch signaling is activated. NICD stimulates expression of HES and HES-driven promoters.

Compounds identified through any screening system can then be tested in animals to assess their effects on angiogenesis, arteriogenesis, or anti-tumor activity in vivo, as well as effects on arterial or venous identity in vivo High-throughput screening of compounds or molecules can be carried out to identify agents or drugs which inhibit angiogenesis or inhibit tumor growth. Test agents can be any chemical (element, molecule, compound, drug), made synthetically, made by recombinant techniques or isolated from a natural source. For example, test agents can be peptides, polypeptides, peptoids, sugars, hormones, or nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

For example, an assay can be carried out to screen for compounds that specifically inhibit binding of Dll4 (ligand) to Notch1/Notch4(receptor), or vice-versa, e.g., by inhibition of binding of labeled ligand- or receptor-Fc fusion proteins to immortalized cells.

In one embodiment of an assay to identify a substance that interferes with interaction of two cell surface molecules (e.g., Notch 1 and Dll4), samples of cells expressing one type of cell surface molecule are contacted with either labeled ligand or labeled ligand plus a test compound (or group of test compounds). The amount of labeled ligand which has bound to the cells is determined. A lesser amount of label (where the label can be, for example, a radioactive isotope, a fluorescent or colormetric label) in the sample contacted with the test compound(s) is an indication that the test compound(s) interferes with binding. The reciprocal assay using cells expressing a ligand can be used to test for a substance that interferes with the binding of an Eph receptor or soluble portion thereof.

An assay to identify a substance which interferes with interaction between Dll4 and Notch1/Notch4 can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all, or a portion of, a protein linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein). Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

Therapeutic Applications

In certain embodiments, the present invention provides methods of inhibiting angiogenesis and methods of treating angiogenesis-associated diseases. In other embodiments, the present invention provides methods of inhibiting or reducing tumor growth and methods of treating an individual suffering from cancer. These methods involve administering to the individual a therapeutically effective amount of one or more modulators of Dll4 signaling as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome, corneal diseases, rubeosis, arthritis, diabetic neovascularization.

In particular, therapeutic agents of the present invention are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia. In certain embodiments, the subject methods of the invention can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject polypeptide therapeutic agent. In certain embodiments of such methods, one or more therapeutic agents of the disclosure can be administered, together (simultaneously) or at different times (sequentially). In addition, therapeutic agents can be administered with another type of compounds for treating cancer or for inhibiting angiogenesis.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a therapeutic agent of the present invention is administered in combination with another conventional anti-neoplastic agent, either concomitantly or sequentially, such therapeutic agent is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha,\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the therapeutic agents of the invention may be continued while the other therapy is being administered and/or thereafter. Administration of the polypeptide therapeutic agents may be made in a single dose, or in multiple doses. In some instances, administration of the therapeutic agents is commenced at least several days prior to the conventional therapy, while in other instances, administration is begun either immediately before or at the time of the administration of the conventional therapy.

In certain embodiments, the disclosure provides methods for stimulating arteriogenesis. Such methods may comprise administering to a subject in need thereof, an effective amount of an agonist of Dll4 signaling. The subject may have or be at risk for an ischemic condition. The subject may have coronary artery disease, including, for example, angina or may have had a myocardial infarction. The subject may have a peripheral artery disease, such as an ischemic event or partial occlusion in a limb, the brain or an organ, such as the kidney. The subject may be diagnosed as being at risk for an ischemic event.

In certain embodiments, the disclosure provides methods for promoting the adoption of arterial characteristics in a blood vessel. Such a method may comprise administering to a blood vessel ex vivo or to a subject in need thereof, an effective amount of an agonist of Dll4 signaling. The blood vessel may be a venous graft, such as a saphenous vein graft, such as may be used in a coronary bypass surgery.

Formulation

In certain embodiments, the subject therapeutic agents of the present invention are formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In certain aspects, the disclosure provides pharmaceutical compositions comprising any of the various nucleic acid compounds targeted to Dll4, Notch1, Notch4 or other members of the pathway. A pharmaceutical composition will generally include a pharmaceutically acceptable carrier.

Pharmaceutical compositions suitable for parenteral administration may comprise one or more polypeptide therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations of the subject polypeptide therapeutic agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject therapeutic agent as an active ingredient.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Therapeutic agents of the invention can be administered topically, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject polypeptide therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Formulations for intravaginal or rectal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In other embodiments, polypeptide therapeutic agents of the instant invention can be expressed within cells from eukaryotic promoters. For example, a soluble polypeptide of Dll4 or Notch1/Notch4 can be expressed in eukaryotic cells from an appropriate vector. The vectors are preferably DNA plasmids or viral vectors. Viral vectors can be constructed based on, but not limited to, adeno-associated virus, retrovirus, adenovirus, or alphavirus. Preferably, the vectors stably introduced in and persist in target cells. Alternatively, viral vectors can be used that provide for transient expression. Such vectors can be repeatedly administered as necessary. Delivery of vectors encoding the subject polypeptide therapeutic agent can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

EXEMPLIFICATION

The invention now being generally described, it will be more readily understood by reference to the following examples, which are included merely for purposes of illustration of certain aspects and embodiments of the present invention, and are not intended to limit the invention.

Example 1

Dosage-Sensitive Requirement for Mouse Dll4 in Artery Development

Duarte et al. (Genes Dev. 2004 Oct. 15; 18(20):2474-8) demonstrated that loss-of-function mutations in mouse Dll4 cause defects in vasculogenesis and angiogenesis, and that these defects are dosage dependent, with $Dll4^{+/-}$ mice showing a less severe phenotype that homozygous $Dll4^{-/-}$ mice. Additionally, the loss of Dll4 function causes a loss of arterial vessel identity. These results demonstrate a level of sensitivity to Dll4 signaling that is unprecedented in the Notch pathway. The sensitivity of vascular development to Dll4 dosage indicates that antagonists of the Dll4-Notch1/4 signaling pathway will be highly effective in inhibiting angiogenesis.

Example 2 mDLL4 Overexpression Causes Arterial Hypertrophy and Loss of Venous Identity in Developing Mouse Embryos In this study Applicants set out to further investigate the role of mDll4 in mammalian vascular development by producing and characterizing murine gain-of-function mutants. To achieve generalized overexpression of mDll4, conditional transgenic mouse lines, ZEG-mDll4, were produced. When crossed with a constitutive cre line, CAG-Cre mice (Sakai et al., 1997), these mice express the native form of mDll4 under the control of the chick beta actin promoter and CMV enhancer. What follows is the description of the gain-of function phenotype observed.

Figure 7:
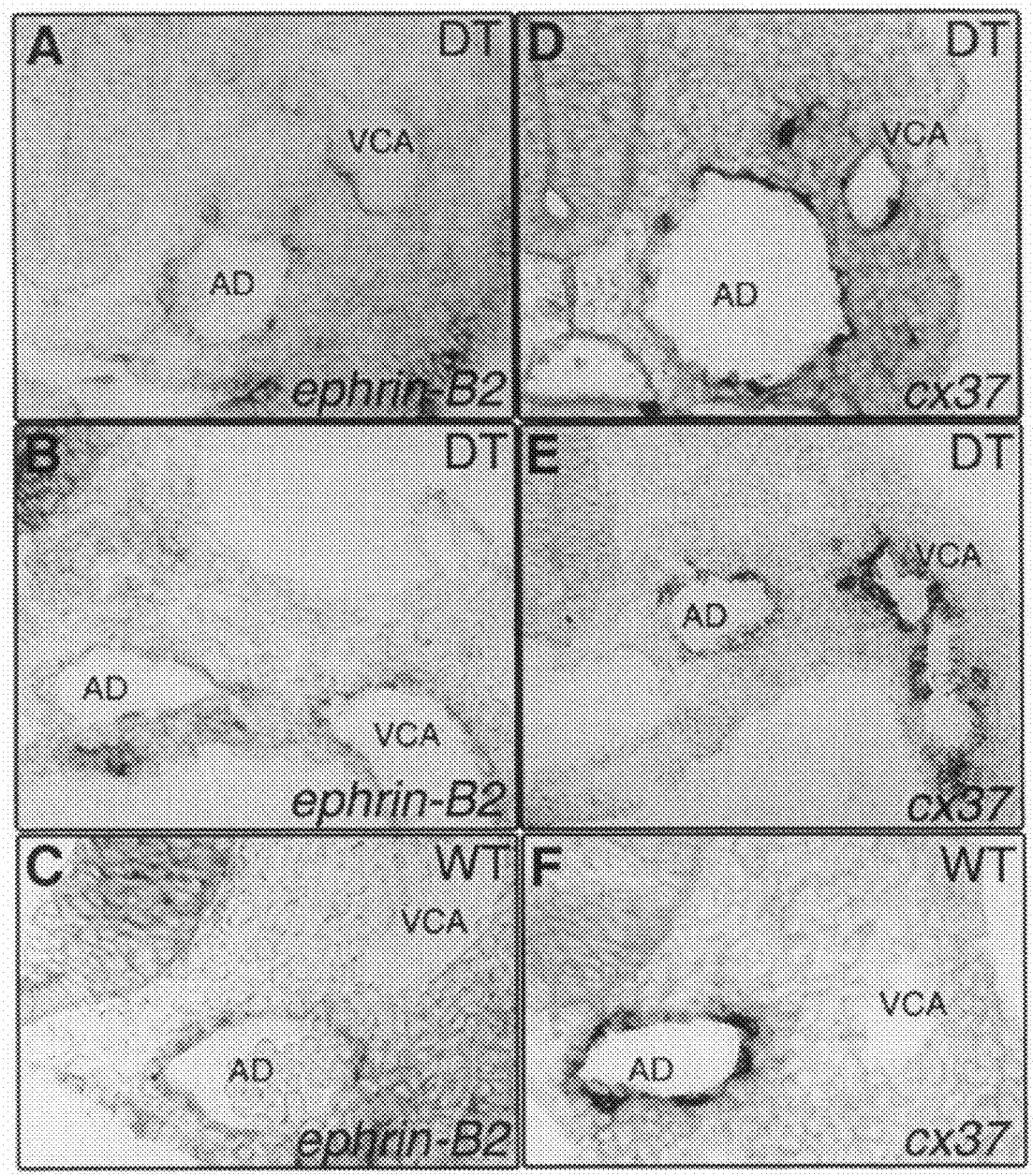
FIG. 7. Venous expression of arterial markers in dt embryos. In situ hybridization of cryosections from E9.0 dt embryos. with ephrin-B2(a, b, c) and connexin-37 (d, e, f) specific riboprobes. The mutant embryos show concomitant expression of these arterial specific markers in the both the dorsal aortae (AD) and anterior cardinal veins (VCA) In the control embryos (c,f), as expected, the expression is restricted to the aortae.
Figure 8:
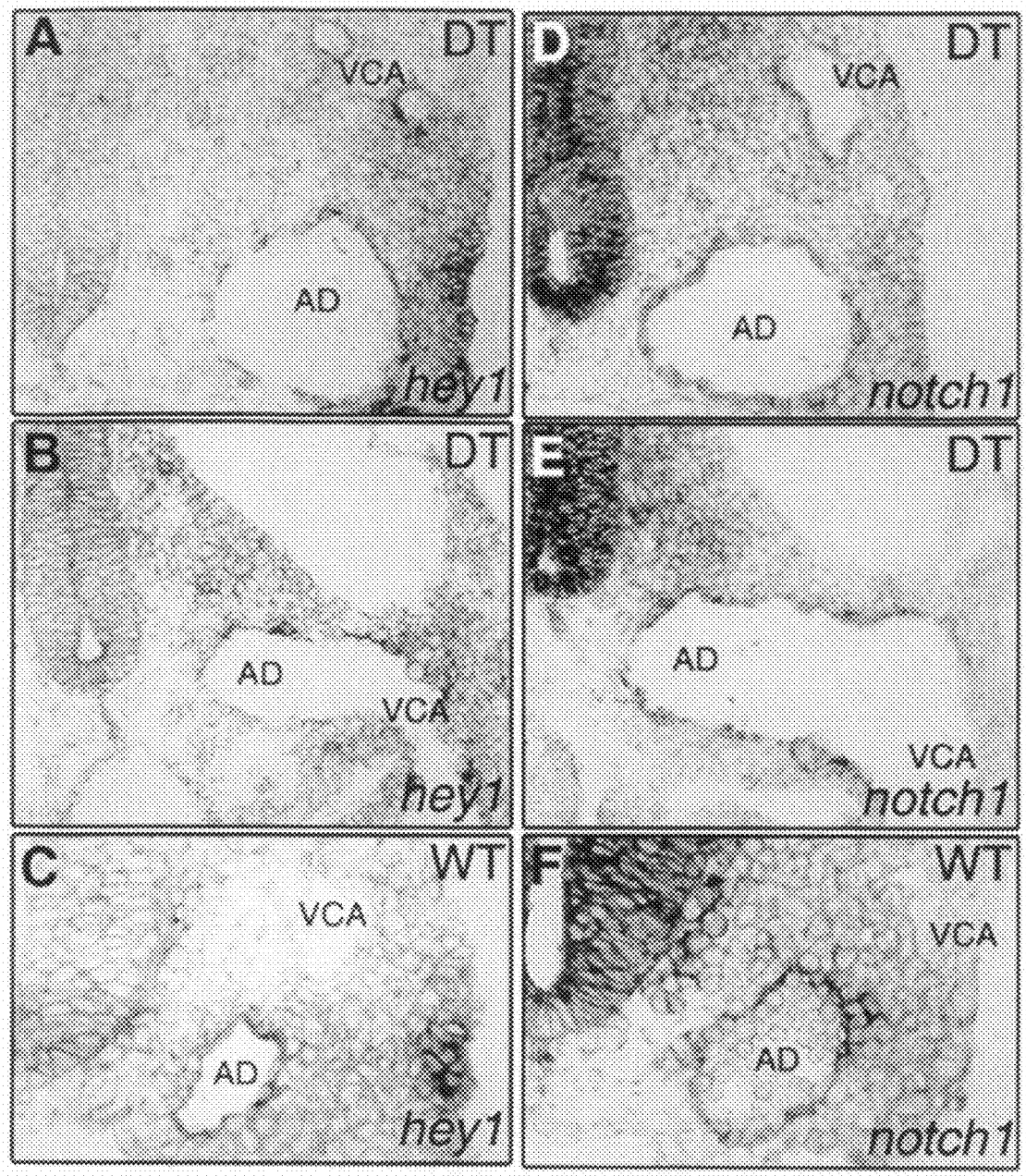
FIG. 8. Upregulation of Notch signalling in the venous endothelium of the mutant embryos. In situ hybridization of cryosections from E9.0 dt embryos. with hey1 (a, b, c) and Notch1 (d, e, f) specific riboprobes. Both genes appear upregulated in the anterior cardinal veins (VCA). In the control embryos (c,f), as expected, the expression is restricted to the aortae.
Figure 9:
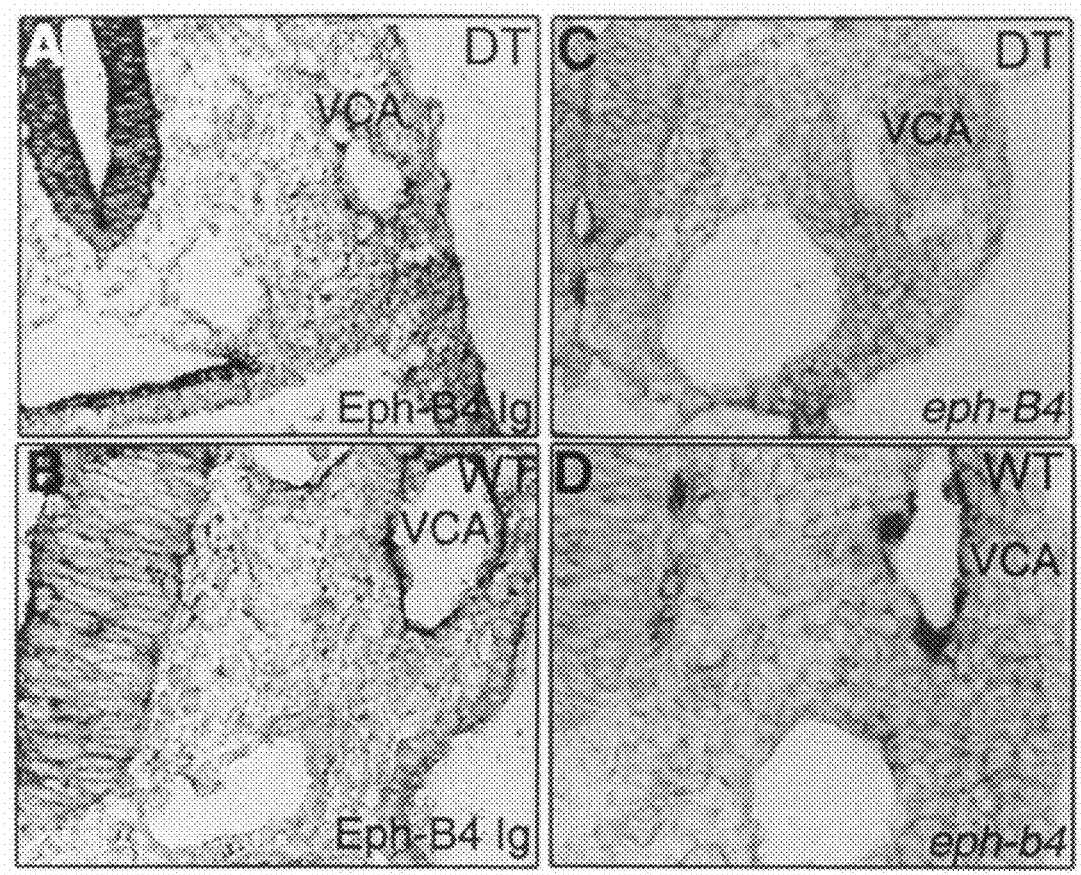
FIG. 9. Downregulation of venous specific markers in dt embryos. In situ hybridization and immunostainings of cryosections from E9.0 dt embryos, (a) anti-Eph-B4 immunostain, (c) eph-b4 mRNA, and E9.0 control embryos, (b) anti-Eph-B4 immunostain, (d) eph-b4 mRNA.
Figure 10:
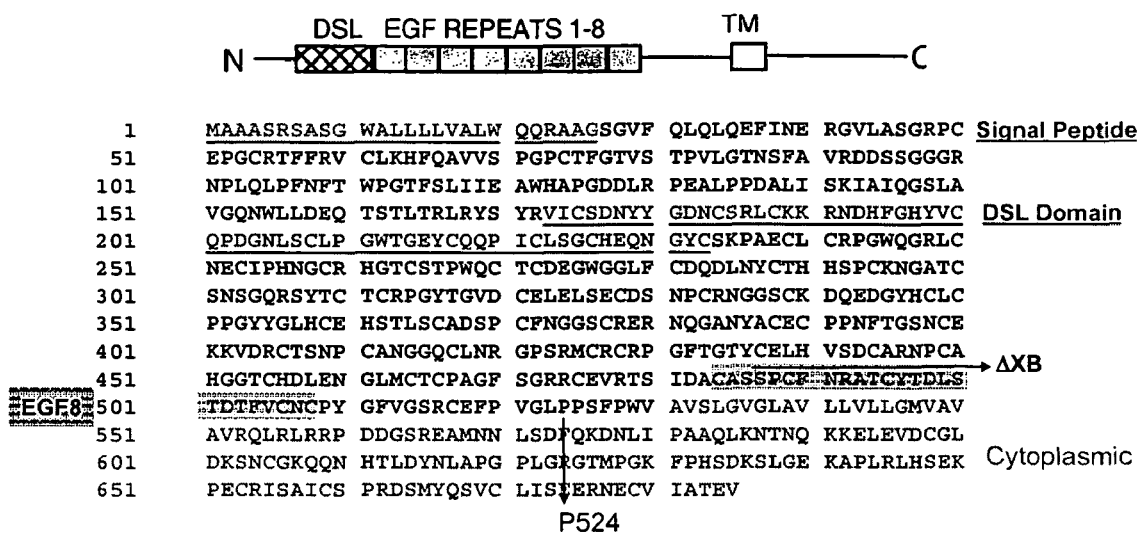
FIG. 10. Shows a schematic of the human Dll4 domain structure (top) and an annotated human Dll4 amino acid sequence (SEQ ID NO:1) (bottom). The signal sequence and DSL domain are underlined and indicated. The eighth EGF8 domain (EGF8) is shaded. The ΔXB (ΔEGF8) construct contains 19 extra amino acids (RSPSCIYRRSWRSRGAQIL) (SEQ ID NO:3) at the C-terminus after the CAS residues of the EGF8 repeat. The P524-His construct ends at P524, 4 amino acids before the transmembrane domain, with a 6×His tag (SEQ ID NO: 14) at the C-terminus. Both constructs contain the receptor-binding domain, DSL domain. Full length constructs have either a Myc tag or no tag.

The mDll4 cDNA was cloned in pCALL2-MigR (Lobe et al., 1999) to produce the pZ/EG-mDll4 transgenesis vector (FIG. 7), which was electroporated into R1 mouse embryonic stem (ES) cells. The transgenic mouse lines, derived from electroporated ES cells by standard methods (Nagy & Rossant, 2000), were crossed to the constitutive cre line, CAG-Cre. Resulting embryos were analysed for EGFP fluorescence, the secondary reporter, which is co-expressed with mDll4 in those cells where the Cre recombination has taken place. EGFP expression was found to be strong and generalized in double transgenic embryos (dt) (FIG. 8), which occurred in normal Mendelian ratios at E8.5 through E9.5. These embryos displayed severe haemorrhaging in the head, heart, branchial arches and posterior ventral region, pericardial edema and incomplete turning at E9.0 (FIG. 8 c). After E10.5 no double-transgenic embryos were recovered. Immunostaining with PECAM1 antisera in wholemount and cryosections of double transgenic embryos revealed arteriovenous malformations, in particular fusions between the dorsal aortae and the anterior cardinal veins (FIG. 10), as early as E8.5. At this stage there was also an evident degree of aortic hypertrophy, which became progressively more pronounced until E9.5, suggesting a role for the Notch pathway in the regulation of endothelial cell proliferation (FIG. 9). In line with this hypothesis, BrdU incorporation studies showed a 40% average increase in endothelial cell proliferation at the anterior dorsal aortae of the double transgenic embryos (not shown). The anterior cardinal veins (ACV), on the other hand, appeared ramified as if they had not undergone correct angiogenic remodelling (FIG. 9) or nearly absent, except for the region directly connecting to the sinus venosus (FIG. 10). Angiogenic remodelling has also failed to occur in the yolk sac and in the head region, the primary capillary plexus persisting in both cases (FIG. 9). The intersomitic vessels were slightly enlarged and shorter than normal, probably as a consequence of fusions between the arterial and venous vessels and failure to ramify at the dorsal-most extremity (FIG. 9). They were also occasionally seen invading somites, which suggests a disruption of their growth path orientation (not shown). At E9.5, the aortae of dt embryos were seen connecting directly to the sinus venosus region (FIG. 10), creating an arterial microcirculation between the extremities of the heart. Presumably as a consequence of insufficient blood flow, the aorta is severely atrophied posteriorly to its connection to the sinus venosus (FIGS. 9 and 10). Microangiography studies with India ink injections show that in these mutants the blood flows from the aortic arches to the aortae and then directly into the sinus venosus, with almost no blood reaching the posterior dorsal aortae (FIG. 10).

Figure 11:
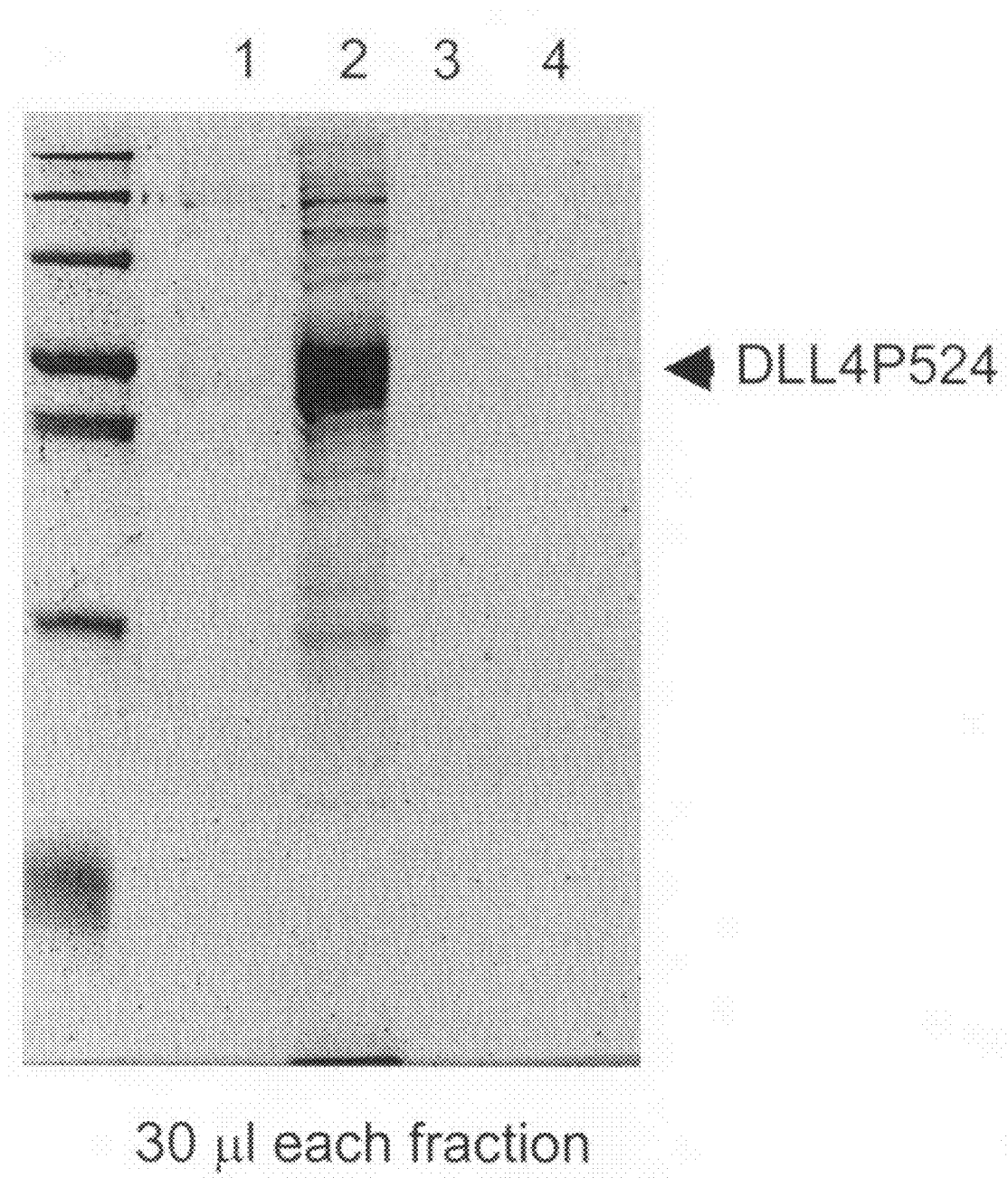
FIG. 11 shows the purified hDll4-P524-6×His protein (SEQ ID NO: 14) (histidine tagged hDll4-P524) after nickel column purification (SDS-PAGE: CBB-G250 Staining).
Figure 12:
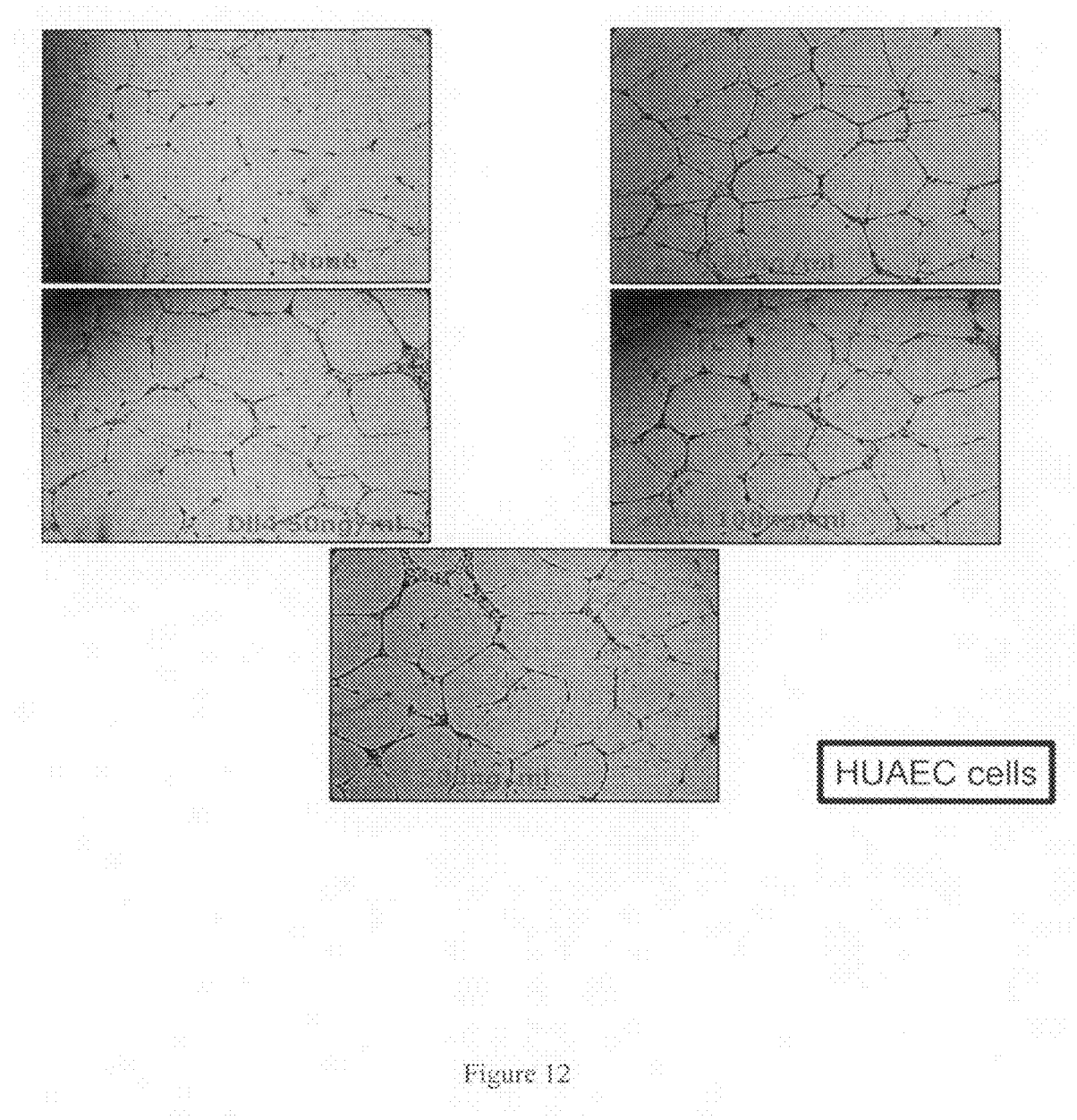
FIG. 12. hDll4 inhibits tube formation in human arterial endothelial cells (HUAEC). VEGF was used at 50 ng/ml as a positive control. Dll4 at lower concentrations (30 ng/ml or 100 ng/ml) promoted tube formation, while Dll4 at 500 ng/ml inhibited tube formation (data not shown). Quantitative analysis for tube length and the number of junctions in sDll4-treated HUVECs (Bioquant Image Analysis; mean from triplicate wells in 2 repetition experiments). Similar results were seen with human arterial endothelial cell assay (data not shown).
Figure 13:
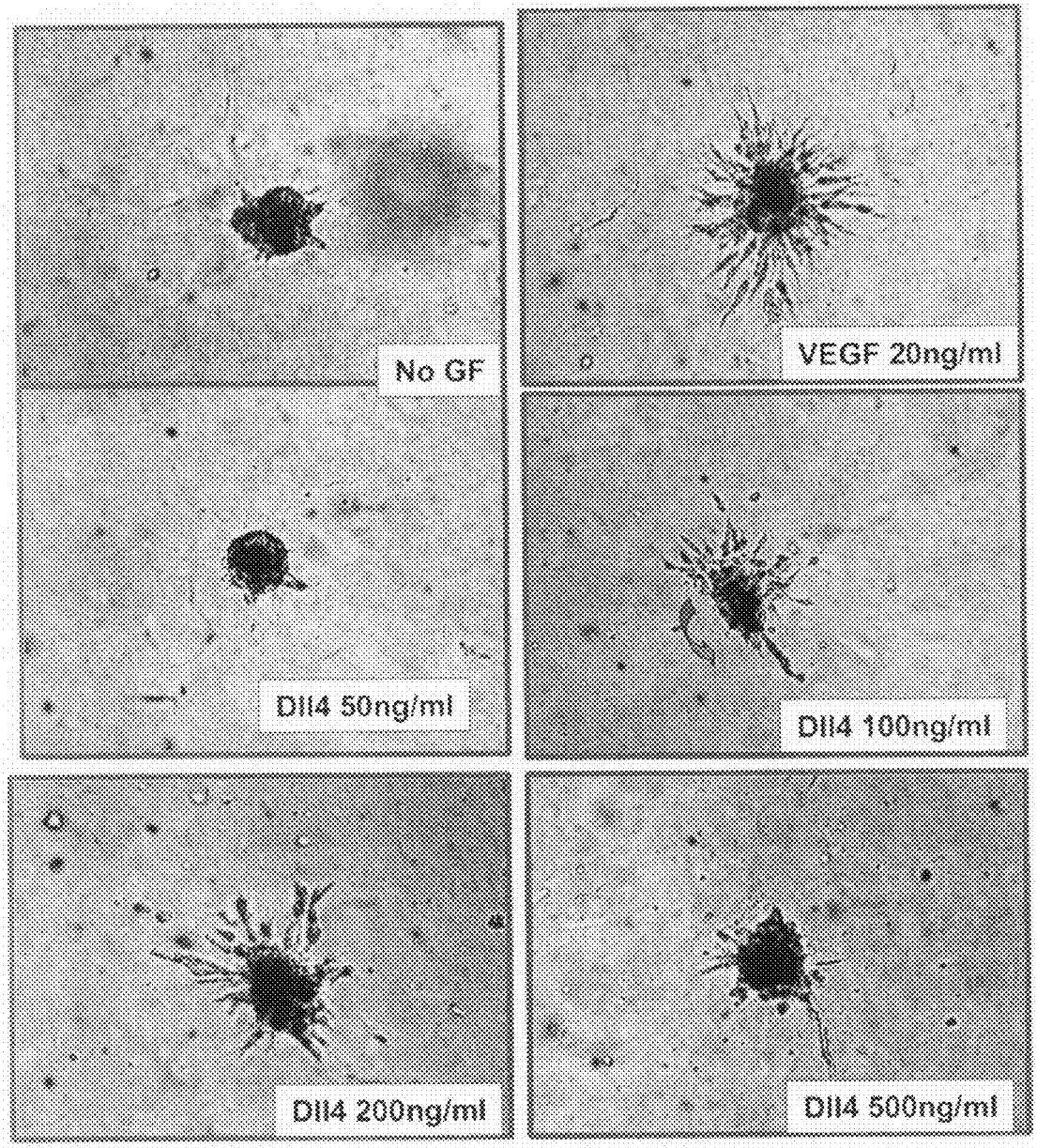
FIG. 13. hDll4 inhibits sprouting in human arterial endothelial cells (HUAEC). VEGF was used at 20 ng/ml as a positive control. Dll4 at 100 ng/mil or 200 ng/ml promoted sprouting, while Dll4 at 500 ng/ml inhibited sprouting (not shown). Quantitative analysis for vascular area is shown (Bioquant Image Analysis; mean from triplicate wells in 2 repetition experiments). Similar results were seen with sDll4-Fc (data not shown).

The characterization of arterial- and venous-specific marker expression revealed a striking mutant phenotype, in which all blood vessels in the embryo presented exclusively arterial markers. The veins of the double transgenic embryos showed ectopic expression of arterial-specific markers such as ephrin-B2, connexin37, hey1 and notch1 (FIGS. 11 and 12). Expression of venous markers (such as EphB4), on the other hand, could not be detected in these mutants (FIG. 13). Furthermore, hematopoietic clusters, which are normally specific of major arteries in the aorta-gonad-mesonephros region, were detected in the sinus venosus region of the mutant embryos at E9.0 (not shown), providing evidence for functional arteriolization of venous structures.

mDll4 overexpression causes aortic hypertrophy and arteriovenous shunting, localized angiogenic arrest, ectopic expression of endothelial arterial identity markers in venous vessels and downregulation of endothelial venous identity markers.

These results demonstrate a role for mDll4 in the establishment of the endothelial arterial cell identity, and suggest its involvement in the regulation of angioblast/endothelial cell proliferation and angiogenesis.

Example 3

Human Delta-Like (hdll4) Regulates Endothelial Cell Tube Formation and Endothelial Cell Sprouting The extracellular domain of human dll4 (amino acids 26-524 of SEQ ID NO:1) was cloned in mammalian expression vector with His tag or Fc tag, and expressed as secreted protein in 293 cell and CHO-K cells. Purified dll4 was first shown to bind Notch 1 and then tested for its in vitro activity on endothelial cell when cultivated on matrigel. See FIGS. 10 and 11. Endothelial cells organized to make tube like structures within 8-24 hr, and the tube formation was minimal in growth factor deprived condition. Addition of VEGF at 20 ng/ml induces tube formation. Dll4 when tested in growth factor deficient conditions, induced tube formation at lower dose levels (100 and 200 ng/ml) while the higher dose level of 500 ng/ml failed to induce tube formation (FIG. 12). Dll4 however did not induce tube formation when added to VEGF containing cultures.

Figure 14:
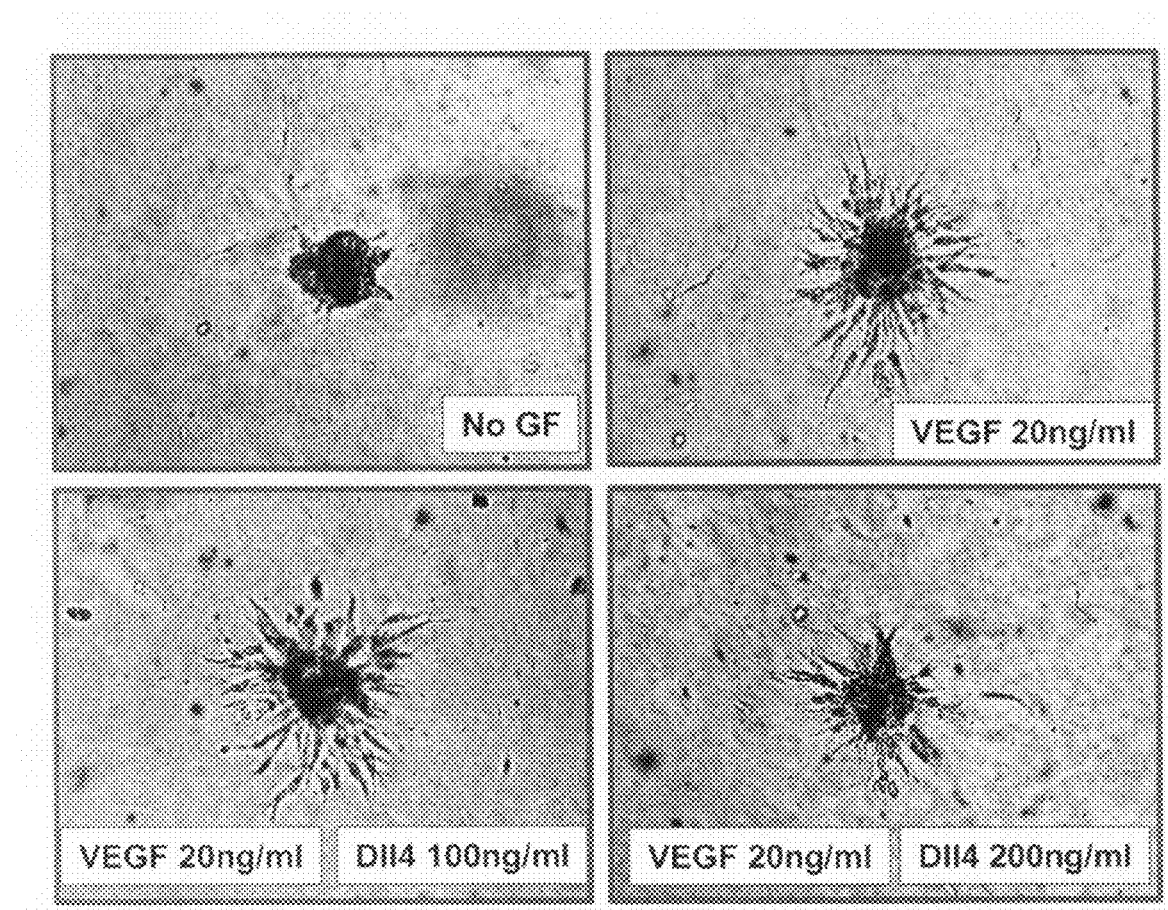
FIG. 14. hDll4 inhibits VEGF-stimulated sprouting in human arterial endothelial cells (HUAEC) at high concentrations. VEGF was used at 20 ng/ml. Dll4 at 100 ng/ml had little effect, while Dll4 at 200 ng/ml inhibited VEGF-stimulated sprouting.

Human dll4 was also tested in sprouting assay where endothelial cell spheroids were treated with varying dose levels of dll4 (FIGS. 13 and 14). Sprouting was induced at the lower dose levels and while higher dose level failed to promote sprouting (FIG. 13). In contrast VEGF treated endothelial cell sprouts were minimally affected by lower levels of dll4, but showed marked reduction in sprouting at higher dose levels (FIG. 14).

Methods and Materials for Example 3:

Generation of Endothelial Cell, Smooth Muscle Cell, and Coculture Spheroids

Endothelial cell and smooth muscle cell spheroids of defined cell number were generated. In brief, SM or HUVE cells were suspended in corresponding culture medium containing 0.25% (w/v) carboxymethylcellulose and seeded in nonadherent round-bottom 96-well plates. Under these conditions, all suspended cells contribute to the formation of a single spheroid per well of defined size and cell number (standard size: 2250 cells/spheroid; in vitro angiogenesis: 750-1000 cells/spheroid). To generate coculture spheroids, equal amounts of suspended SM and HUVE cells (standard size: 1125 SMC and 1125 HUVEC per spheroid; in vitro angiogenesis: 500 SMC and 500 HUVEC per spheroid) were mixed and seeded in nonadherent round-bottom 96-well plates as described above. Spheroids were cultured for at least 24 h and used for the corresponding experiments.

In Vitro Angiogenesis Assay

In vitro angiogenesis in collagen gels was quantitated using endothelial cell, smooth muscle cell, and coculture spheroids as described previously. In brief, spheroids containing 750-1000 cells were generated overnight, after which they were embedded into collagen gels. A collagen stock solution was prepared prior to use by mixing 8 vol acidic collagen extract of rat tails (equilibrated to 2 mg/ml, 4° C.) with 1 vol 10×EBSS (Gibco BRL, Eggenstein, Germany); 1 vol 0.1 N NaOH to adjust the pH to 7.4. This stock solution (0.5 ml) was mixed with 0.5 ml room temperature medium (ECGM basal medium [PromoCell] with 40% FCS containing 0.5% (w/v) carboxymethylcellulose to prevent sedimentation of spheroids prior to polymerization of the collagen gel, 50 spheroids, and the corresponding test substance. The spheroid containing gel was rapidly transferred into prewarmed 24-well plates and allowed to polymerize (1 min), after which 0.1 ml ECGM basal medium was pipetted on top of the gel. The gels were incubated at 37° C., 5% CO2, and 100% humidity. After 24 h, in vitro angiogenesis was digitally quantitated by measuring the length of the sprouts that had grown out of each spheroid (ocular grid at 100× magnification) using the digital imaging software DP-Soft (Olympus) analyzing at least 10 spheroids per experimental group and experiment.

Fluorescent Cell Labeling

SMC and HUVEC were labeled using the fluorescent dyes PKH26 (red fluorescence) and PKH67 (green fluorescence) following manufacturer's instructions. After trypsinization, suspended cells were washed once with HBSS, membrane labeled with PKH26 or PKH67 for 5 min, and washed three times using corresponding culture medium. Quality of cell labeling was examined using fluorescence microscopy.

Ultrastructural Analysis

Spheroids were fixed in Karnovsky's fixative, postfixed in 1.0% osmium tetroxide, dehydrated in a graded series of ethanol, and embedded in Epon. Sections of 0.5 μm were cut and stained with azure 11 methylene blue for light microscopic evaluation. Ultrathin sections (50-80 nm) were cut, collected on copper grids, and automatically stained with uranyl acetate and lead citrate for observation with a Zeiss EM 10 electron microscope.

For quantitation of interendothelial junctional complexes in surface spheroid endothelial cells, all junctional complexes of 20 randomly selected spheroids per experimental group in two independent preparations were counted. Results were expressed as the number of junctional complexes per 100 surface monolayer endothelial cells (analysis of at least 200 EC per experimental group).

Morphological and Immunohistochemical Analysis

Spheroids were harvested and centrifuged for 3 min at 200 g. Cultured monolayer cells were harvested by trypsinization and collected by centrifugation. Spheroids and pelleted monolayer cells were fixed in HBSS containing 4% paraformaldehyde and processed for paraffin embedding; after dehydration (graded series of ethanol and isopropanol, 1 h each), the specimens were first immersed with paraffin I (melting temperature 42° C.) for 12 h at 60° C. Spheroids and monolayer cells were again collected by centrifugation and immersed with paraffin II (melting temperature 56° C.) for 12 h at 70° C. Finally, the resulting paraffin block was cooled to room temperature and trimmed for sectioning. For histochemical analyses, paraffin sections (4 μm) were cut, deparaffinized, and rehydrated. Sections were then incubated with 3% H2O2 in H2O to inhibit endogenous peroxidase. After washings in phosphate-buffered saline, the sections were incubated for 30 min with blocking solution (10% normal goat serum), followed by incubation with the corresponding primary antibody in a humid chamber at 4° C. overnight. Then they were incubated with secondary antibody (biotinylated goat anti-rabbit immunoglobulin or biotinylated goat anti-mouse immunoglobulin antibody; Zymed, San Francisco, Calif.), exposed to streptavidin peroxidase, developed with diaminobenzidine as substrate, and weakly counterstained with hematoxylin.

Detection of Apoptotic Cells in Spheroids

Apoptotic cells were visualized by histochemical detection of nucleosomal fragmentation products (TUNEL) applying the In Situ Cell Death Detection Kit, following the manufacturer's instructions. In brief, nucleosomal fragmentation products in sections of paraffin-embedded spheroids were detected after deparaffination and proteinase K digestion by 3' end labeling with fluorescein-dUTP using terminal deoxynucleotidyl transferase. Labeling was visualized either directly by fluorescence microscopy or indirectly after incubating the sections with peroxidase-labeled anti-fluorescein antibody and developing with diaminobenzidine as substrate.

DNA Fragmentation Enzyme-Linked Immunoassay (ELISA)

Quantitation of fragmented DNA was performed by ELISA (Cell Death Detection ELISA Kit). Fragmented DNA of 10 spheroids was extracted by lysis for 60 min at room temperature with vigorous shaking. The extracts were centrifuged for 10 min at 13,000 g and 300 μl of the supernatant was incubated with peroxidase-labeled anti-DNA antibody and biotinylated anti-histone antibody in streptavidin-coated microtiter plates following the manufacturer's instructions. After washing, binding of mono- and oligonucleosomal DNA was visualized by developing with the peroxidase substrate ABTS (2,2'-azino-di[3-ethylbenzthiazolin-sulfonate]). Plates were analyzed at 405 nm using an automated microtiter plate reader.

Statistical Analysis

All results are expressed as mean±SD. Differences between experimental groups were analyzed by unpaired Student's t test. P values <0.05 were considered statistically significant

Example 4

Vascular Proliferation in Embryonic and Adult Dll4+/− Mutant Mice

Dll4$^{-/-}$ and most of Dll4$^{+/-}$ mice die in utero due to defective vascular development[17]. Close examination of the Dll4$^{+/-}$ embryos showed normal vasculogenesis until E8.75, when the first vascular defect became apparent. There was increased vascular proliferation appearing like honeycomb and lacking hierarchical arterial branching and maturation (FIG. 15A). We next studied vascular response and remodeling in adult Dll4$^{+/-}$ mutant and wild type mice. Mice (six week old) were implanted with S180 tumor cells. Tumor and adjacent tissue harvested after 10 days was examined for vascular response by PECAM, and α-SMA immuno-localization. Wild type mice showed increased vascular response in the tumor (FIG. 15B) and the vessels had organized network. In comparison Dll4$^{+/-}$ mice showed an even greater increase in the vascular response (1.5 fold increase, P<0.05). Furthermore the vessels showed lack of architecture and loss of hierarchy. Thus vascular response was increased but maturation was lacking. Maturation of newly forming vessels accompanies the recruitment of pericytes. We hypothesized that newly forming vessels in Dll4$^{+/-}$ mice may be defective in pericyte recruitment. Thus localization of pericytes with A-SMA antibodies showed abundant signal in tumor vessels in wild type mice, whereas tumor vessels in Dll4$^{+/-}$ mice showed a profound deficiency in pericyte coverage (FIG. 15D). Reduced recruitment of pericytes may contribute to the lack of vascular hierarchy in Dll4$^{+/-}$ mice tumor vessels. Furthermore these findings reveal a novel function of Dll4 in the recruitment of pericytes to newly forming vessels. We next wished to determine if defective vascular response in adult mice lead to alteration in gene expression, in particular dll4. To this end we utilized the LacZ reporter included in the targeting vector used to generate mutant mice to observe Dll4 promoter activity. Dll4$^{+/-}$ mutant mice showed highly structured LacZ expressing vessels in the normal tissue adjacent to the tumor (FIG. 15C), whereas LacZ activity was markedly increased in vessels within the tumor vessels (FIG. 15C), indicative of Dll4 activation in the tumor vasculature. PECAM localization in serial sections of the tumor vessels was done to determine the extent of Dll4 activation in tumor vasculature. Dll4 is expressed in the majority but not all tumor vessels (FIG. 15E).

Example 5

Soluble Dll4 Inhibits Dll4-Notch Signaling

We next wished to determine if soluble Dll4 could antagonize Notch activation. Extracellular domain of human Dll4 fused either to AP, Fc or His tag were expressed in mammalian cells, purified and determined to bind Notch 1-Fc (FIG. 16A) and Notch4-Fc (data not shown) but not Notch3-Fc (FIG. 16A) or Fc alone (data not shown). Notch activation is dependent on the expression of Dll4 in the cellular context. To test that the soluble forms of Dll4 do not induce Notch activation, we introduced various Dll4 constructs in endothelial cells and examined the induction of downstream Notch responsive genes (Hey1, Hey2, Hes1, and Hes2) induction by RT-PCR. Representative data for the absence of Notch activation is shown by the lack of Hes2 induction by Dll4-Fc or Dll4-His (FIG. 16B). Hes2 is downstream of Notch and induced by full length Dll4 when presented in the cellular context (FIG. 16C). We next determined if sDll4 can inhibit the activity of cellular Dll4 in inducing Notch signaling. To this end full length-Dll4 (Dll4-FL) was introduced into choK cells and co-cultured with HUVEC cells expressing target Notch1 and Notch 4. Dll4-FL induces Notch regulated genes, Hey1, Hey2, Hes1 and Hes2 (FIG. 16C) in human endothelial cells using human gene specific primer pairs. In identical experiments, addition of human sDll4-Fc and sDll4-His blocked Dll4-FL induced activation of both Hey1, Hey2, Hes1 and Hes2 (FIG. 16C). Thus soluble Dll4 functions as an antagonist of Dll4-Notch signaling. Quantitation of gene expression showed that Dll4-Fc inhibited Hey1, Hey2, Hes 1 and Hes2 to 69, 26, 29 and 46% of control, while sDll4-His reduced their expression to 48.3, 10 and 28% respectively.

Example 6 sDll4 Induces Vascularization of Matrigel Plugs In Vivo

To further demonstrate that sDll4 can directly inhibit angiogenesis in vivo, we performed a murine Matrigel plug experiment. Matrigel was supplemented with VEGF, sDll4-Fc, sDll4-His or various combinations, and injected into the ventral abdominal subcutaneous tissue of Balb/C nu/nu mice. Matrigel plugs without growth factors had virtually no vascularization after 6 days (FIG. 17A), while VEGF recruited endothelial cells and formed various stages of vascular structures including those with open lumen containing red blood cells throughout the plug. sDll4 in the context of VEGF showed a marked increase in vascular structures (FIG. 17) which appeared like thin strings, and mostly lacked lumen. Similarly, sDll4 alone, in the absence of VEGF was also capable of inducing angiogenesis. Immuno-chemical examination with PECAM further demonstrates the contrast between VEGF induced large vessel filled with red blood cells and sDll4 induced vessels which express PECAM but lack lumen and lack perfusion defined by the presence of red blood cells (FIG. 17B). Hemoglobin was also quantitated specifically by the Drabkin method using a Drabkin reagent kit. and fold change was compared with control measurement represented as 1. Median hemoglobin levels were thus were 1, 9.7, and 2.5, and 3 in control, VEGF, Dll4-Fc, and Dll4-His groups. There was a near four fold decrease in hemoglobin concentration in sDll4 containing Matrigel plugs, compared to VEGF alone.

Example 7 sDll4 Inhibits the Growth of Human Tumors in Athymic Mice

Tumor vessels have distinctive gene expression profile over resting vessels. Dll4 is one of the genes induced in tumor vessels in certain human and murine tumors (FIG. 15C). Dll4 induction may be a generalized feature of tumor vessels, one which could be beneficial for tumor growth. Dll4 expression is seen predominantly in the tumor vasculature. To determine the effect of sDll4 on tumor cells, tumor cell viability in vitro with various concentrations of sDll4 was tested (HT29, MCF-7, SCC-15, B16, PC3 and KS-SLK cell lines), and no effect was observed (data not shown). Given the ability of Dll4 to profoundly affect angiogenesis in vivo, and the observed sDll4 alteration of the vascular response, we speculated that sDll4 may modulate tumor growth in vivo. We therefore examined the activity of sDll4 in vivo in tumor xenograft models. HT29 (human colon carcinoma cell line) and KS-SLK (human Kaposi's sarcoma cell line) cells were premixed with Matrigel-containing vehicle or sDll4 and implanted subcutaneously. Compared to control tumors, xenografts supplemented with sDll4 exhibited a significantly reduced tumor growth over two weeks (FIG. 18A). Similar results were obtained in KS-SLK. Median tumor volume of control tumors at 2 weeks was 585 mm3 while that of tumors in Matrigel containing sDll4-His was 267 mm3 respectively.

Figure 18:
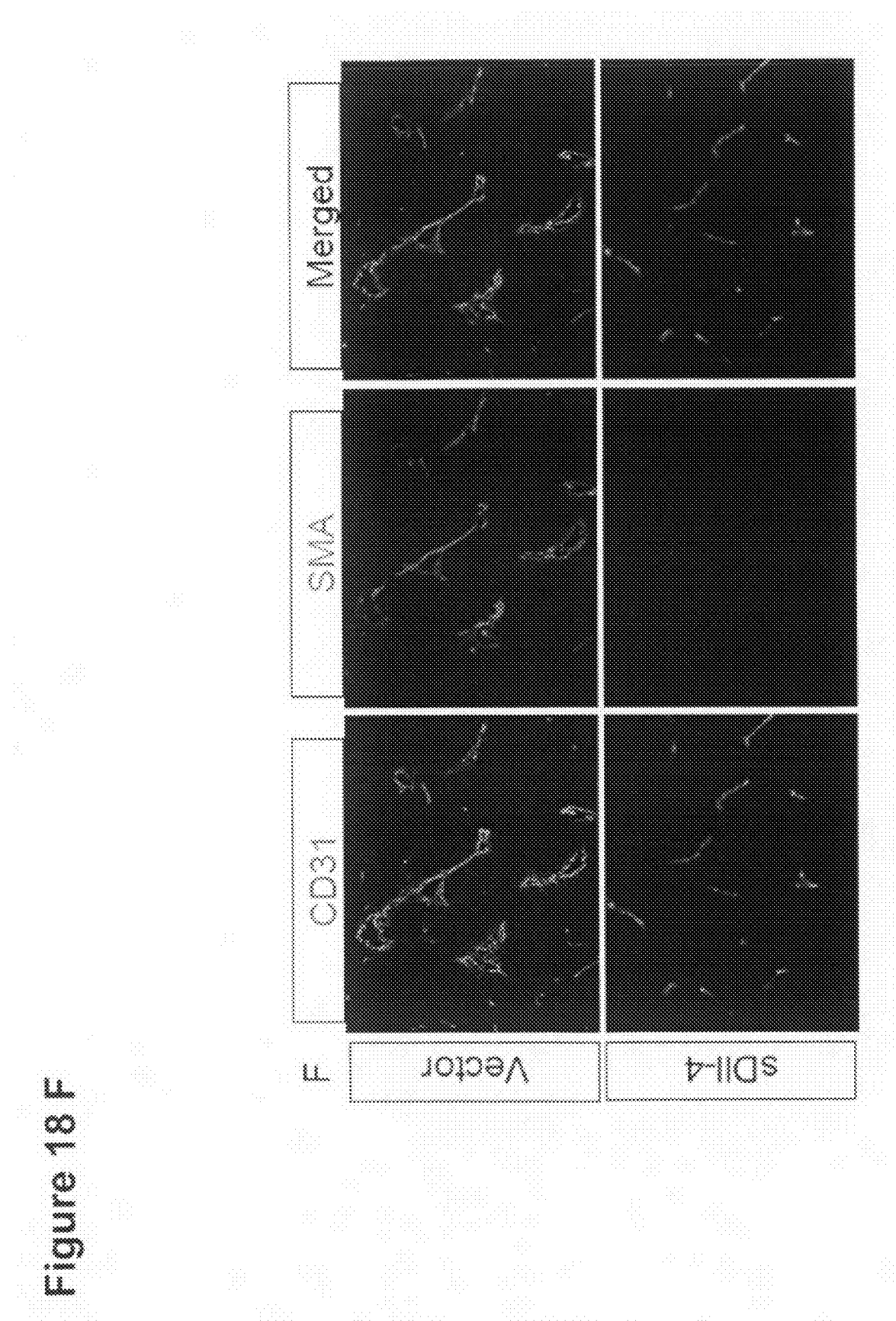
FIG. 18. sDll4 inhibits the tumor growth in a murine tumor xenograft model: (A) Mice (n=6/group) were given implants with 1×10$^6$ HT29 cells in a Matrigel preparation with PBS or sDll4-Fc or sDll4-His (5 ug/ml) and tumor volumes measured after 2 weeks, tumors were harvested and analyzed. Tumor volumes were significantly smaller in the sDll4 arm (FIG. 6A). The experiment was repeated twice. (B) In assessing the effect of endogenous expression of sDll4, HT29 were transfected with expression vector with Dll4-FL, sDll4-Fc, sDll4-His, or vector alone. Co-expression of truncated CD4 was done to allow sorting of the transfected cells. Equal number of the transfected cells were implanted in mice (n=6/group). Tumor volumes were assessed (FIG. 6B). Tumor volumes were significantly smaller in the sDll4 groups. (C) Microvasculature was assessed by PECAM immuno-staining and the blood vessel volume was quantitated as described in method section. (D). Hypoxy probe was infused prior to tumor harvest, tumor sections were then probed with MAb and fluorescent labeled secondary antibody as described in methods. Hypoxic areas were quantitated using ImageJ as described in methods. All values are expressed as mean±SEM. *P<0.01 by Student t test. Photomicrographs were taken using a Nikon Coolpix 5000 camera and a Nikon Eclipse E400 microscope with a 10× eyepiece. Magnification was 20×/0.5 NA objectives. (E). Vascular perfusion was determined by injecting fluorescent labeled lectin 10-15 min prior to sacrificing mice and harvesting tumors. Lectin was localized to perfused areas while blood vessels were delineated with PECAM staining. Lectin and PECAM co-localized in control group, while sDll4 group showed marked deficiency of perfusion. (F). Localization of α-SMA in tumor vessel. Control group showed co-localization of α-SMA and PECAM, while sDll4 group had paucity of α-SMA positive cells in the microvessels.
Figure 19:
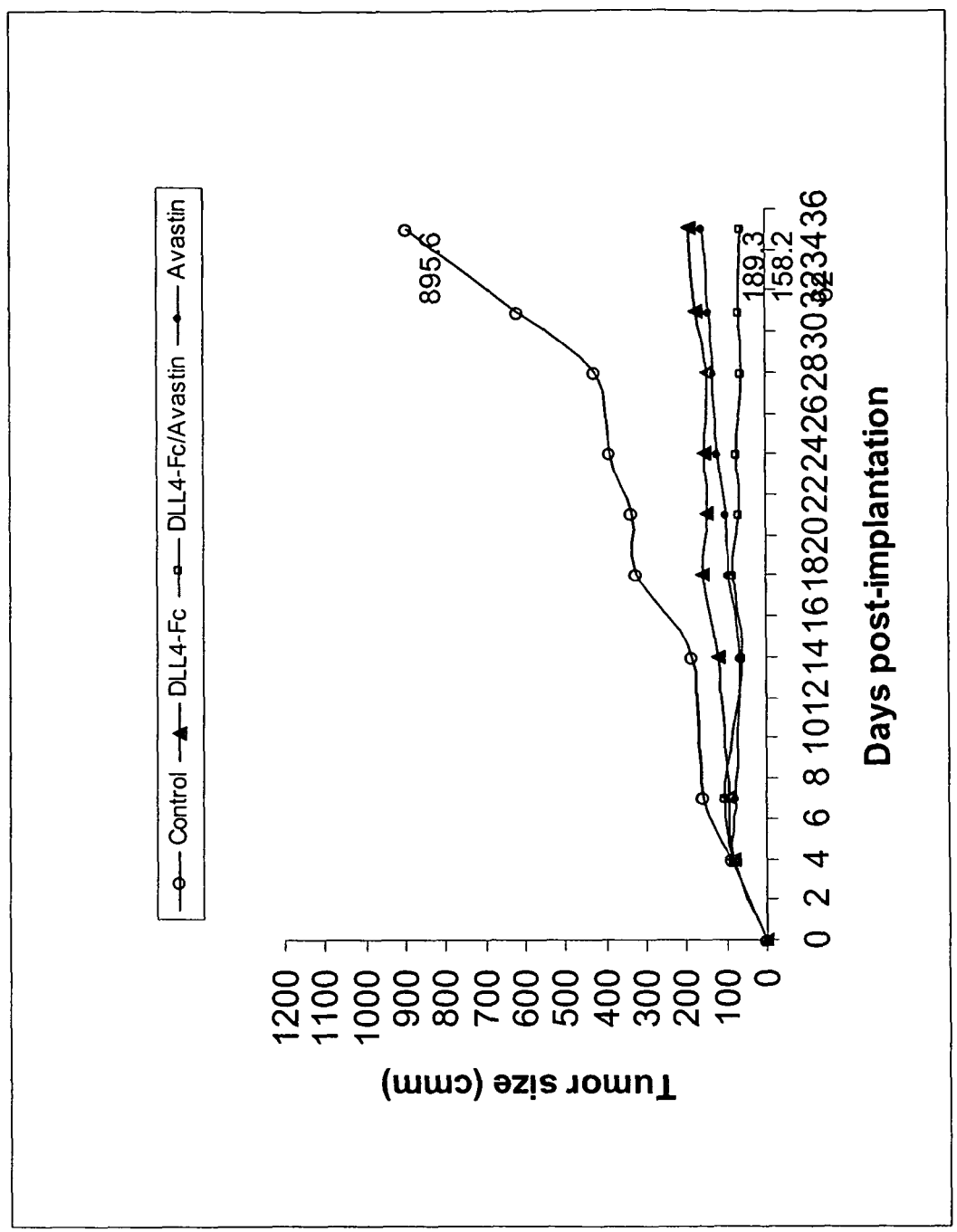
FIG. 19. Soluble Dll4 inhibits tumor growth in vivo in a murine zenograft model. Dll4-E6 (residues 1-422 of SEQ ID NO: 1) which lacks EGF-like domains 7 and 8 was administered intraperitoneally starting at day 5 post implantation at 5 mg/kg, three times a week. VEGF-stimulated sprouting in human arterial endothelial cells (HUAEC) at high concentrations. The combined effect of Dll4-E6 with a VEGF neutralizing antibody (Avastin) was also examined. Avastin was also administered intraperitoneally starting at day 5 post implantation at 10 mg/kg, three times a week.

We next studied the effect of sDll4 when produced by tumor cells. HT29 and KS-SLK cells were transfected with expression vectors to produce Dll4-FL, sDll4-Fc, sDll4-His and expression of each protein was confirmed in Western blot assays (data not shown). Co-expression of truncated CD4 allowed sorting of transfected cells to over 90% purity. Equal numbers of cells ($1\times10^6$ per injection site) were implanted in athymic mice (6-8 tumors per group) and tumor volume was measured for two weeks. Tumor volume was similar in vector alone and Dll4-FL, while sDll4-Fc and sDll4-His had markedly reduced tumor volume (over 70% reduction with sDll4-His) (FIG. 18B). Harvested tumors harvested at the time were examined for vascular density using PECAM immuno-staining. Tumors expressing Dll4-FL or vector alone showed highly structured vessels (FIG. 18C). In contrast sDll4 expressing tumors showed marked changes in the vessel architecture. There were many more branching points in sDll4 expressing tumor vasculature compared to vector alone or Dll4-FL (FIG. 18). Similar results were obtained in KS-SLK tumor xenografts. Remarkably the vessels appeared thin and often lacking apparent lumen. These characteristics were reminiscent of blood vessel branching in Dll4$^{+/-}$ mice, and in Matrigel plugs impregnated with sDll4. Consistent with poorly forming thin vessel lacking lumen, we examined the areas of hypoxia. Analysis of hypoxia focused on viable tumor regions only. There were large and wide areas of hypoxia in sDll4-Fc and sDll4-His. Quantitation of these areas showed marked increase in hypoxic regions of sDll4 expressing tumors compared to both Dll4-FL and vector expressing tumors (FIG. 18D). Tumor perfusion was also measured using fluorescent labeled lectin which binds to the luminal surface of the blood vessels. There was very limited perfusion in the sDll4 expressing tumors as compared to Dll4-FL and vector transfected cells (FIG. 18E). In addition we determined the presence of pericytes on newly forming tumor vessels by localizing α-SMA expression. Tumor vessels in wild type mice showed normal pericyte coverage whereas tumor vessels in Dll4$^{+/-}$ mice present a dramatic reduction of pericyte coverage as determined by the number of α-SMA positive cells lining the endothelial cells. sDll4 similarly reduced the number of pericytes in tumor vessels in athymic mice bearing human tumors.

Materials and Methods

The materials and methods used in examples 4-7 are set forth below:

Analysis of Dll4 germ-line mutant mice in embryos and adults: Dll4 knock out mice were generated in CD1 background and described previously[16]. Dll4$^{-/-}$ and most Dll4$^{+/-}$ mouse embryos have a lethal phenotype. The vasculature of Dll4$^{+/-}$ embryos was visualized with platelet endothelial cell adhesion molecule (PECAM) and alpha smooth muscle actin (α-SMA) staining. Dll4$^{+/-}$ mice that survived to adulthood were studied for alterations in the vasculature. Dll4$^{+/-}$ CD1 male mice and wild type mice (6-8 weeks old) were transplanted with 5×106 tumor cells (S180 mouse sarcoma cell line). Tumors were harvested after 2 weeks for analysis. Dll4 expression was studied in Dll4$^{+/-}$ mice in the tumor tissue and adjacent normal tissue by the use of a LacZ reporter included in the targeting vector. Whole-mount embryo immunohistochemistry (PECAM antibody was from Pharmingen) and lacZ staining were carried out by standard techniques[18].

RT-PCR analysis: First-strand cDNA was synthesized from total RNA using a SuperScript Preamplification System kit (GIBCOBRL) and used (0.1 µg) for PCR with specific primers for Dll4, GAPDH, β-actin, Hey1, Hey2, Hes1, Hes2 (primer pairs used in this study are available on request), PCR products were visualized by ethidium bromide staining.

Antibodies and other reagents: Anti-PECAM (M20) from Santa Cruz Biotechnology (Santa Cruz, Calif.), anti-α-SMA (Dako, Carpinteria, Calif.), IgG-Fc fragment and antihuman Fc from Jackson Laboratories (Bar Harbor, Me.), Notch1-Fc and Notch3-Fc from R&D (R&D systems), Hypoxyprobe-1 from Chemicon (Chemicon International, Temecula, Calif.), Rhodamine labeled *Ricinus Communis* Agglutinin I (RCA) from Vector labs (Vector labs, Burlingame, CAsi), and alkaline phosphatase substrate PNPP was purchased from Sigma (Sigma Chemicals, St. Louis, Mo.).

Cell culture: Normal human umbilical vein endothelial cells (HUVECs) and human umbilical arterial endothelial cells (HUAECs) were obtained from Cambrex (Walkersville, Md.) and maintained in EGM2-supplemented medium (Invitrogen). For all experiments, HUVECs and HUAECs were used at passages 4 or below and collected from a confluent dish. ChoK cell line was obtained from American Type Culture Collection (Manassas, Va.) and cultured under recommended conditions.

Dll4 constructs: Full length human Dll4 gene was cloned by PCR amplification from human cDNA (Clonetech) made from fetal lung tissues. Both full length (amino acid residues 1-685) and C-terminally His-tagged extracellular domain (amino acid residues 1-486) proteins were expressed from pcDNA3.1 expression vector (Invitrogen). Fc fusion protein was expressed from pCXFc vector (Invitrogen). AP fusion protein was expressed from pAPtag-2 vector (GeneHunter Corp.). All proteins were transiently expressed in ChoK cells (ATCC) using Lipofectamine 2000 (Invitrogen). His-tagged and Fc-fusion Dll4 proteins were purified through Nickel-NTA column and Protein A-Sepharose column[19].

Notch receptor binding and activation pathway: Five μg/ml Notch1-Fc and Notch3-Fc were coated overnight at 4° C. in PBS on 96-well plates. Dll4-AP was diluted in PBS and 0.1% Tween-20 (PBST), 50 μl of each dilution was incubated with Notch-Fc and blocked with 5% milk in PBS for one hour. Wells were washed three times with PBST, developed with PNPP and read at OD405. Typically, human umbilical vein endothelial cells (HUVECs) were grown in 100-mm dishes until 80% confluence and were co-cultured with choK cells transiently expressing full length Dll4 (1:1 ration) or choK cells transfected with vector alone. Co-cultures were treated with either rDll4-His or rDll4-Fc for a period of 24 hr, cells were harvested and total RNA was isolated for further analysis[20].

Cell sorting: For sorting transfected cells, the MACSelect 4.1 transfected cell selection kit was used as per manufacturer's instructions. In brief, cells were cotransfected with expression vector containing the plasmid of interest and pMACS 4.1 plasmid. After 36 hr, cells were harvested with 5 mM EDTA and incubated with MACSelect 4 Microbeads for 15 min at 4° C. The cell suspension was then passed via an MS+ column in a magnetic field. After 3 washes, the column was removed from the field and selected cells eluted in culture medium. Selection efficiency was confirmed by FACS analysis of sorted cells with fluorescent Dll4 monoclonal antibody (data not shown).

EC tube formation assay: Matrigel (250 μL; BD Biosciences, Palo Alto, Calif.) was placed in each well of an ice-cold 24-well plate. The plate was allowed to sit at room temperature for 15 minutes, and 37° C. for 30 minutes for Matrigel to polymerize. HUVECs in EGM2 medium were plated at a concentration of $1\times10^4$ cells/well with test material at various concentrations in triplicates. After 6-hour and 24-hour incubations, pictures were taken for each concentration using a Bioquant Image Analysis system (Bioquant, Nashville, Tenn.). Length of cords formed and number of junctions were compared among various groups using ImageJ software (NIH, Bethesda, Md.). Experiments were repeated twice[19].

Vessel sprouting: Endothelial cell spheroids were generated by suspending equal number of endothelial cells (1000 cells/well) in culture medium containing 0.25% (w/v) carboxymethylcellulose and seeded in nonadherent round-bottom 96-well plates. Endothelial cells were suspended to form a single spheroid per well. Spheroids were embedded into collagen gels and cultured for at least 24 h. Sprouting was recorded digitally (ocular grid at 100× magnification) using the digital imaging DP-Soft (Olympus) analyzing at least 10 spheroids per experimental group and experiment. Sprouting was also quantitated by measuring the length of the sprouts by ImageJ[19].

Murine Matrigel plug angiogenesis assay: In vivo angiogenesis was assayed using the Matrigel plug assay. Matrigel rapidly forms a solid gel at body temperature, trapping the factors to allow slow release and prolonged exposure to surrounding tissues. Matrigel (8.13 mg/mL, 0.5 mL) in liquid form at 4° C. was mixed with vehicle alone (PBS containing 0.25% BSA) or VEGF, or sDll4, or VEGF and sDll4 together. Matrigel (0.5 mL) was injected into the abdominal subcutaneous tissue of female Balb/C nu/nu mice (6 weeks old, 5 mice per group) along the peritoneal midline. On day 6, mice were humanely killed and plugs were recovered weighed, and divided for hemoglobin measurement and immuno-histochemical analysis. Vascular identity of the infiltrating cells was established with PECAM immuno-staining. The experiment was repeated three times. The vascularized area in each section was calculated using ImageJ. Hemoglobin in one-half of the Matrigel plug was measured using the Drabkin method (Drabkin reagent kit 525; Sigma, St. Louis, Mo.) using the manufacturer's recommended protocol. Immunohistochemistry and immunofluorescence: Sections (5 μm) of formalin-fixed paraffin-embedded tissues were processed using standard methods[16,19]. Sections were incubated with primary antibody overnight at 4° C. and appropriate secondary antibody for 1 hour at room temperature. Antibody binding was localized with ABC staining kit form Vector Laboratories (Burlingame, Calif.) according to the manufacturer's instructions and peroxidase activity detected using DAB substrate solution (Vector Laboratories). Routine negative controls were exclusion of primary and secondary antibody and substitution of normal IgG isotype for primary antibody. The positive staining area was estimated using ImageJ and analyzed by Student t test. Fluorescent immunostaining was performed in a similar fashion to detect the expression level of EC-specific markers including PECAM. Appropriate fluorescein-conjugated secondary antibodies (Sigma-Aldrich, St Louis, Mo.) were used and nuclei were counterstained with 4',6-diamidino-2-phenylindole dihydrochloride hydrate (DAPI). Slides were mounted with Vectashield antifade mounting solution (Vector Laboratories) and images obtained using an Olympus AX70 fluorescence microscope and Spot v2.2.2 (Diagnostic Instruments, Sterling Heights, Mich.) digital imaging system.

Murine tumor xenografts: Tumor cells ($1.5\times10^6$) HT29 (human colon cancer cell line) or KS-IMM (human Kaposi's sarcoma cancer cell line) were implanted subcutaneously in flanks of male athymic BalbC nu/nu mice (6-8 weeks old, 6 mice/group and repeated twice). For assessing local effects of sDll4, tumor cells were mixed with Matrigel (1:1 vol/vol; BD Biosciences) with or without 5 μg/ml of sDll4. Tumor volume was measured on day 14 estimated as $0.52\times a \times b^2$, where a and b are the largest and smallest lengths of the palpable tumor. The Student t test was used to compare tumor volumes, with $P<0.05$ being considered significant. Animals were humanely killed and tumor and adjacent normal tissues were harvested. Harvested tissues were divided to either fixed in formalin or frozen in OCT for analysis. Distribution and intensity of hypoxia was studied using hypoxyprobe-1 (HP1-100, Chemicon) infused intraperitoneally at a dose of 60 mg/kg one hour prior to the tumor harvest and localized using recommended protocol. Vessel perfusion was studied using rhodamine labeled *Ricinus Communis* Agglutinin 1 (Vector Labs) infused 10-15 minutes prior to the tumor harvest and analyzed using the manufacturer recommended protocol. All procedures were approved by our Institutional Animal Care and Use Committees and performed in accordance with the Animal Welfare Act regulations.

REFERENCES

Adams, R. H., Wilkinson, G. A., Weiss, C., Diella, F., Gale, N. W., Deutsch, U., Risau, W. and Klein, R. (1999). *Genes Dev* 13, 295-306.

Artavanis-Tsakonas, S., Rand, M. D. and Lake, R. J. (1999). *Science* 284, 770-6.

Duarte, A., Hirashima, M., Benedito, R., Trindade, A., Diniz, P., Bekman, E., Costa, L., Henrique, D., Rossant, J. (2004) *Genes Dev* 18, 2474-8.

Fischer, A., Schumacher, N., Maier, M., Sendtner, M. and Gessler, M. (2004). *Genes Dev* 18, 901-11.

Gale, N. W., Baluk, P., Pan, L., Kwan, M., Holash, J., DeChiara, T. M., McDonald, D. M. and Yancopoulos, G. D. (2001). *Dev Biol* 230, 151-60.

Iso, T., Hamamori, Y. and Kedes, L. (2003) *Arterioscler Thromb Vasc Biol* 23, 543-53.

Krebs, L. T., Xue, Y., Norton, C. R., Shutter, J. R., Maguire, M., Sundberg, J. P., Gallahan, D., Closson, V., Kitajewski, J., Callahan, R. et al. (2000) *Genes Dev* 14, 1343-52.

Lawson, N. D., Vogel, A. M. and Weinstein, B. M. (2002) *Dev Cell* 3, 127-36.

Nagy, A. and Rossant, J. (2000). In *Gene targeting: a practical approach*, (ed. A. L. Joyner), pp. 177-206. New York: Oxford University Press.

Mumm, J. S. and Kopan, R. (2000) *Dev Biol* 228, 151-65.

Sakai, K. and Miyazaki, J. (1997) *Biochem Biophys Res Commun* 237, 318-24.

Shutter, J. R., Scully, S., Fan, W., Richards, W. G., Kitajewski, J., Deblandre, G. A., Kintner, C. R. and Stark, K. L. (2000) *Genes Dev* 14, 1313-8.

Uyttendaele, H., Marazzi, G., Wu, G., Yan, Q., Sassoon, D. and Kitajewski, J. (1996) *Development* 122, 2251-9.

Yoneya et al. J. Biochem. Vol. 129, pp. 27-34 (2001)

Li et al. Genomics. 1998 Jul. 1; 51(1):45-58.

Lobe et al., Dev Biol. 1999 Apr. 15; 208(2):281-92.

Risau W. Mechanisms of angiogenesis. Nature. 1997; 386: 671-674.

Rossant J and Hirashima M. Vascular development and patterning: making the right choices. Curr Opin Genet Dev. 2003; 13:408-412.

Folkman J. Fundamental concepts of the angiogenic process. Curr Mol. Med. 2003; 3:643-651.

Carmeliet P. Angiogenesis in life, disease and medicine. Nature. 2005; 438:932-936.

Ferrara N, Carver-Moore K, Chen H, et al. Heterozygous embryonic lethality induced by targeted inactivation of the VEGF gene. Nature. 1996; 380:439-442.

Bray S J. Notch signalling: a simple pathway becomes complex. Nat Rev Mol Cell Biol. 2006; 7:678-689.

Iso T, Hamamori Y, Kedes L. Notch signaling in vascular development. Arterioscler Thromb Vasc Biol. 2003; 23:543-553.

Hainaud P, Contreres J O, Villemain A, et al. The Role of the Vascular Endothelial Growth Factor-Delta-like 4 Ligand/Notch4-Ephrin B2 Cascade in Tumor Vessel Remodeling and Endothelial Cell Functions. Cancer Res. 2006; 66:8501-8510.

Krebs L T, Xue Y, Norton C R, et al. Notch signaling is essential for vascular morphogenesis in mice. Genes Dev. 2000; 14:1343-1352.

Uyttendaele H, Marazzi G, Wu G, Yan Q, Sassoon D, Kitajewski J. Notch4/int-3, a mammary proto-oncogene, is an endothelial cell-specific mammalian Notch gene. Development. 1996; 122:2251-2259.

Shutter J R, Scully S, Fan W, et al. Dll4, a novel Notch ligand expressed in arterial endothelium. Genes Dev. 2000; 14:1313-1318.

Wang H U, Chen Z F, Anderson D J. Molecular distinction and angiogenic interaction between embryonic arteries and veins revealed by ephrin-B2 and its receptor Eph-B4. Cell. 1998; 93:741-753.

Gerety S S, Wang H U, Chen Z F, Anderson D J. Symmetrical mutant phenotypes of the receptor EphB4 and its specific transmembrane ligand ephrin-B2 in cardiovascular development. Mol Cell. 1999; 4:403-414.

Lawson N D, Vogel A M, Weinstein B M. sonic hedgehog and vascular endothelial growth factor act upstream of the Notch pathway during arterial endothelial differentiation. Dev Cell. 2002; 3:127-136.

Fischer A, Schumacher N, Maier M, Sendtner M, Gessler M. The Notch target genes Hey1 and Hey2 are required for embryonic vascular development. Genes Dev. 2004; 18:901-911.

Duarte A, Hirashima M, Benedito R, et al. Dosage-sensitive requirement for mouse Dll4 in artery development. Genes Dev. 2004; 18:2474-2478.

Krebs L T, Shutter J R, Tanigaki K, Honjo T, Stark K L, Gridley T. Haploinsufficient lethality and formation of arteriovenous malformations in Notch pathway mutants. Genes Dev. 2004; 18:2469-2473.

Hogan B, Beddington R, Constantini F, and Lacy E. *Manipulating the mouse embryo*. Cold Spring Harbor, N.Y.: Laboratory Press; 1994.

Kertesz N, Krasnoperov V, Reddy R, et al. The soluble extracellular domain of EphB4 (sEphB4) antagonizes EphB4-EphrinB2 interaction, modulates angiogenesis, and inhibits tumor growth. Blood. 2006; 107:2330-2338.

Xia G, Kumar S R, Hawes D, et al. Expression and significance of vascular endothelial growth factor receptor 2 in bladder cancer. J Urol. 2006; 175:1245-1252.

Carmeliet P, Ferreira V, Breier G, et al. Abnormal blood vessel development and lethality in embryos lacking a single VEGF allele. Nature. 1996; 380:435-439.

Shweiki D, Itin A, Soffer D, Keshet E. Vascular endothelial growth factor induced by hypoxia may mediate hypoxia-initiated angiogenesis. Nature. 1992; 359:843-845.

Mailhos C, Modlich U, Lewis J, Harris A, Bicknell R, Ish-Horowicz D. Delta4, an endothelial specific notch ligand expressed at sites of physiological and tumor angiogenesis. Differentiation. 2001; 69:135-144.

Diez H, Fischer A, Winkler A, et al. Hypoxia-mediated activation of Dll4-Notch-Hey2 signaling in endothelial progenitor cells and adoption of arterial cell fate. Exp Cell Res. 2006.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations

We claim:

1. An isolated monoclonal antibody or antigen binding portion thereof, wherein the antibody or the antigen binding portion thereof has an amino acid sequence comprising SEQ ID NO: 4 and SEQ ID NO: 5.

2. An isolated monoclonal antibody or antigen binding portion thereof, wherein the antibody or the antigen binding portion thereof has an amino acid sequence comprising SEQ ID NO: 6 and SEQ ID NO: 7.

3. The isolated monoclonal antibody of claim 1, wherein the antibody or antigen binding portion thereof binds to an epitope in the extracellular portion of DLL4 situated within a domain selected from MNNL, DSL, and one or more EGF repeats.

4. The isolated monoclonal antibody of claim 1, wherein the antibody or antigen binding portion thereof is a humanized antibody.

5. The isolated monoclonal antibody of claim 2, wherein the antibody or antigen binding portion thereof binds to an epitope in the extracellular portion of DLL4 situated within a domain selected from MNNL, DSL, and one or more EGF repeats.

6. The isolated monoclonal antibody of claim 2, wherein the antibody or antigen binding portion thereof is a humanized antibody.

* * * * *